(12) United States Patent
Augeri et al.

(10) Patent No.: US 8,093,246 B2
(45) Date of Patent: Jan. 10, 2012

(54) O-LINKED PYRIMIDIN-4-AMINE-BASED COMPOUNDS, COMPOSITIONS COMPRISING THEM, AND METHODS OF THEIR USE TO TREAT CANCER

(75) Inventors: David J. Augeri, Princeton, NJ (US); Marianne Carlsen, Yardley, PA (US); Kenneth G. Carson, Princeton, NJ (US); Qinghong Fu, Plainsboro, NJ (US); Jason P. Healy, Flemington, NJ (US); Alexander Heim-Riether, Newtown, CT (US); Theodore C. Jessop, Lawrenceville, NJ (US); Philip E. Keyes, Flemington, NJ (US); Min Shen, Pennington, NJ (US); James E. Tarver, Morrisville, PA (US); Jerry A. Taylor, Trenton, NJ (US); Xiaolian Xu, Princeton, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 1001 days.

(21) Appl. No.: 11/954,433

(22) Filed: Dec. 12, 2007

(65) Prior Publication Data

US 2008/0146571 A1    Jun. 19, 2008

Related U.S. Application Data

(60) Provisional application No. 60/874,882, filed on Dec. 14, 2006.

(51) Int. Cl.
C07D 403/14 (2006.01)
A61K 31/506 (2006.01)

(52) U.S. Cl. .......... 514/235.8; 514/241; 514/252.18; 514/257; 514/263.21; 514/274; 544/122; 544/194; 544/250; 544/277; 544/296; 544/317

(58) Field of Classification Search .......... 544/122, 544/194, 250, 277, 296, 317; 514/235.8, 514/241, 252.18, 257, 263.21, 274
See application file for complete search history.

(56) References Cited

U.S. PATENT DOCUMENTS

| | | | |
|---|---|---|---|
| 5,492,915 A | 2/1996 | Dereu | |
| 5,530,129 A | 6/1996 | Gallenkamp | |
| 6,737,427 B2 | 5/2004 | Jones | |
| 6,750,219 B1 | 6/2004 | Ajito | |
| 6,787,562 B2 | 9/2004 | Breault | |
| 6,906,067 B2 | 6/2005 | Moriarty | |
| 6,995,144 B2 | 2/2006 | Ozaki | |
| 7,015,227 B2 | 3/2006 | Darrow | |
| 2002/0165218 A1 | 11/2002 | Halbrook | |
| 2003/0171218 A1* | 9/2003 | Bojack et al. | 504/221 |
| 2005/0009834 A1 | 1/2005 | Ito | |
| 2005/0101630 A1 | 5/2005 | Boyle | |
| 2005/0107399 A1 | 5/2005 | Boman | |
| 2005/0159446 A1 | 7/2005 | Chew | |
| 2006/0111326 A1 | 5/2006 | Almansa | |
| 2006/0122209 A1 | 6/2006 | Zhang | |
| 2006/0160851 A1 | 7/2006 | Ebdrup | |
| 2006/0178381 A1 | 8/2006 | Jolidon | |
| 2006/0217372 A1 | 9/2006 | Blanco-Pillado | |
| 2007/0116784 A1 | 5/2007 | Ward | |

FOREIGN PATENT DOCUMENTS

| | | |
|---|---|---|
| JP | 2005194250 | 7/2005 |
| WO | WO 9633972 | 10/1996 |
| WO | WO 0147897 | 7/2001 |
| WO | WO 2004/074278 * | 9/2004 |
| WO | WO 2004074278 | 9/2004 |
| WO | WO 2006032138 | 3/2006 |
| WO | WO 2006038594 | 4/2006 |
| WO | WO 2006045828 | 5/2006 |
| WO | WO 2006108487 | 10/2006 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, pp. 1-7, Aug. 2002.*
Simone, Oncology: Introduction, Cecil Textbook of Medicine, 20th Edition, vol. 1, pp. 1004-1010, 1996.*
Gura et al., Systems for Identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
International Search Report for International Application No. PCT/US2007/087332, dated Jun. 30, 2008.

* cited by examiner

*Primary Examiner* — Deepak Rao
(74) *Attorney, Agent, or Firm* — Max Bachrach

(57) ABSTRACT

O-linked pyrimidin-4-amine-based compounds, pharmaceutical compositions comprising them, and methods of their use are described. Particular compounds of the invention are of formula I:

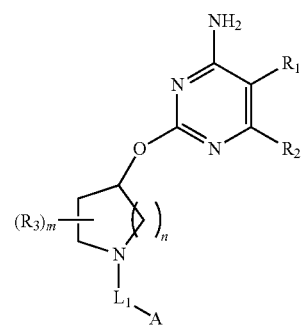

18 Claims, 2 Drawing Sheets

O-LINKED PYRIMIDIN-4-AMINE-BASED COMPOUNDS, COMPOSITIONS COMPRISING THEM, AND METHODS OF THEIR USE TO TREAT CANCER

This application claims priority to U.S. provisional application No. 60/874,882, filed Dec. 14, 2006, the entirety of which is incorporated herein by reference.

1. FIELD OF THE INVENTION

This invention relates to O-linked pyrimidin-4-amine-based compounds, pharmaceutical compositions comprising them, and methods of their use to treat, manage and prevent cancer.

2. BACKGROUND OF THE INVENTION

Deoxycytidine kinase is an enzyme involved in deoxynucleoside salvage, supplying precursors for DNA synthesis. Csapó, Z. et al., *Acta Biochimica Polonica* 48(1):251-256, 251 (2001). The enzyme is able to phosphorylate three of the four deoxynucleosides, and also phosphorylates a variety of antineoplastic and antiviral nucleoside analogues. Id.; Chottiner, E. G., et al, *Proc. Natl. Acad. Sci. USA* 88:1531-1535, 1531 (1991). For example, the enzyme reportedly activates cytosineb-D-arabinofuranoside (AraC), fludarabine and cladribine, the chemotherapeutic agents gemcytabine and troxacitabine, and the antivirals 3TC and ddC, which are used in the treatment of HIV infection. Sabini, E. et al., *Nature Stuct. Biol.* 10(7):513-519, 513 (2003).

Although deoxycytidine kinase activates some anti-cancer drugs, reports suggest that at least one anti-cancer drug may act, at least in part, by inhibiting the enzyme. See, e.g., International Application WO04/103374. In this regard, a link between neoplastic transformation and increased deoxycytidine kinase levels in solid cancer tissues has been reported. See Arnér, E. S. J. and Eriksson, S., *Pharmac. Ther.* 67(2): 155-186, 165 (1995). Some deoxycytidine kinase inhibitors have been reported. See, e.g., Krenitsky, T. A. et al., *J. Biol. Chem.* 251(13):4055-4061 (1976); Ward, A. D. and Baker, B. R., *J. Med. Chem.* 20(1):88-92 (1976).

3. SUMMARY OF THE INVENTION

This invention encompasses O-linked pyrimidin-4-amine-based compounds, pharmaceutical compositions comprising them, and methods of their use.

Embodiments of the invention encompasses compounds of formulae I, II and III:

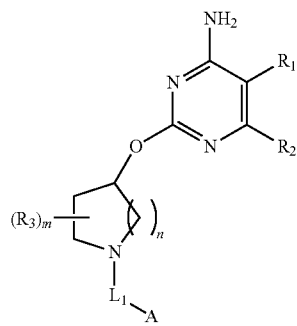

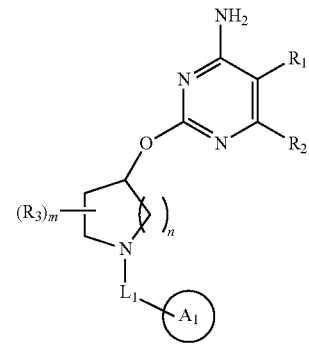

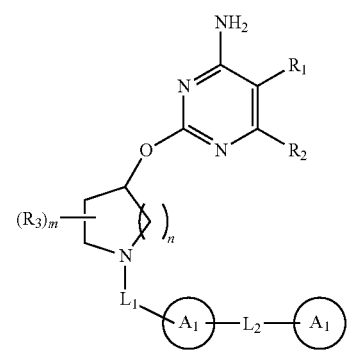

and pharmaceutically acceptable salts and solvates thereof, the various substituents of which are defined here. Particular compounds are potent deoxycytidine kinase inhibitors.

The invention encompasses pharmaceutical formulations and single unit dosage forms comprising compounds disclosed here.

The invention also encompasses methods of inhibiting deoxycytidine kinase, and methods of treating, managing and preventing diseases and disorders, such as cancer.

4. BRIEF DESCRIPTION OF THE FIGURES

FIG. 1 shows the effect of a compound of the invention alone, and in combination with 4-hydroperoxycyclophosphamide (4-HC), on the growth of mouse B cell lymphoma cells (BCL-1). The effect is shown as a percentage of the control rate of growth (i.e., untreated BCL-1 cells). Here, the concentration of the compound was 1 μM, and the concentration of 4-HC (when used) is shown in the x-axis.

5. DETAILED DESCRIPTION OF THE INVENTION

Figure 1:
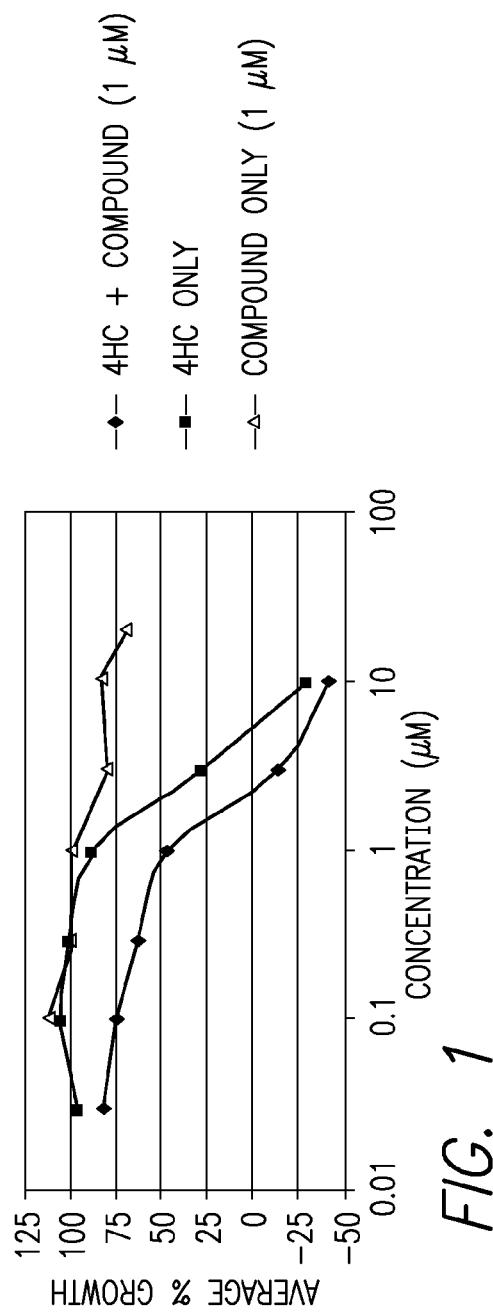

This invention is directed, in part, to O-linked pyrimidin-4-amine-based compounds and compositions comprising them. Particular compounds of the invention inhibit deoxycytidine kinase, and may be useful in the treatment of cancer.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$—CH$_3$, and —O(CH$_2$)$_5$CH$_3$. The term "lower alkoxy" refers to —O-(lower alkyl).

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "dCK_IC$_{50}$" means an IC$_{50}$ for human recombinant deoxycytidine kinase as determined using the filter binding assay described in the Examples, below.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "managing cancer," "managing cancer" and "management of cancer" mean reducing the rate of growth of cancerous cells.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "potent deoxycytidine kinase inhibitor" means a compound that has a dCK_IC$_{50}$ of less than about 1 μM.

Unless otherwise indicated, the terms "prevent cancer," "preventing cancer" and "prevention of cancer" mean inhibiting the growth of cancerous cells.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat cancer," "treating cancer" and "treatment of cancer" mean causing apoptosis of cancerous cells.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

5.2. Compounds of the Invention

This invention encompasses compounds of formula I:

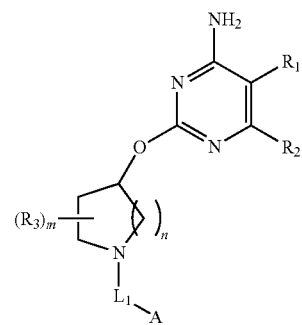

and pharmaceutically acceptable salts and solvates thereof, wherein: L$_1$ is a bond (i.e., the nitrogen is directly bound to A), —C(O)—, —SO$_2$—, or —C(R$_4$)$_2$—; A is optionally substituted alkyl, aryl or heterocycle; R$_1$ is hydrogen, halogen, —OH, —NH$_2$, —NO$_2$, —CN, —C(O)OR$_4$, or optionally substituted alkyl; R$_2$ is hydrogen, halogen, —OH, —NH$_2$, —NO$_2$, —CN, —C(O)OR$_4$, or optionally substituted alkyl; each R$_3$ is independently =O or optionally substituted lower alkyl; each R$_4$ is independently hydrogen or lower alkyl; n is 1-3; and m is 0-3 if n is 1, m is 0-4 if n is 2, or m is 0-5 if n is 3.

Also encompassed are compounds of formula II:

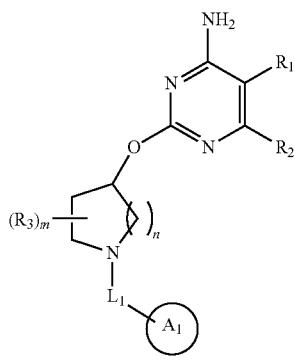

II and pharmaceutically acceptable salts and solvates thereof, wherein: L$_1$ is a bond (i.e., the nitrogen is directly bound to A$_1$), —C(O)—, —SO$_2$—, or —C(R$_4$)$_2$—; A$_1$ is optionally substituted cycloalkyl, aryl or heterocycle; R$_1$ is hydrogen, halogen, —OH, —NH$_2$, —NO$_2$, —CN, —C(O)OR$_4$, or optionally substituted alkyl; R$_2$ is hydrogen, halogen, —OH, —NH$_2$, —NO$_2$, —CN, —C(O)OR$_4$, or optionally substituted alkyl; each R$_3$ is independently =O or optionally substituted lower alkyl; each R$_4$ is independently hydrogen or lower alkyl; n is 1-3; and m is 0-3 if n is 1, m is 0-4 if n is 2, or m is 0-5 if n is 3.

Some compounds of formula II are such that at least one of the following is true: 1) n is not 1; 2) A$_1$ is not optionally substituted phenyl; 2) A$_1$ is not optionally substituted cycloalkyl; 3) A$_2$ is not optionally substituted heterocycle; 4) R$_1$ is not cyano or lower alkyl; 5) R$_2$ is not cyano or lower alkyl; 6) R$_3$ is not oxo; 7) m is 0; and/or 8) when n is 1, L$_1$ is a bond, and A$_1$ is optionally substituted phenyl, R$_3$ is not oxo.

Also encompassed are compounds of formula III:

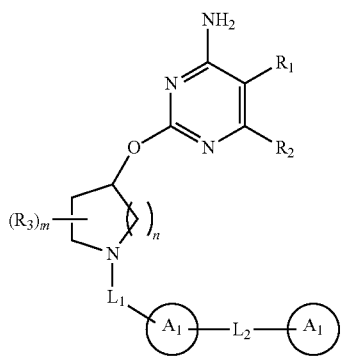

III and pharmaceutically acceptable salts and solvates thereof, wherein: L$_1$ is a bond (i.e., the nitrogen is directly bound to A$_1$), —C(O)—, —SO$_2$—, or —C(R$_4$)$_2$—; L$_2$ is a bond (i.e., A$_1$ is directly bound to A$_2$), —O—, —C(O)—, —SO$_2$—, —C(NOH)—, or —C(R$_5$)$_2$—; A$_1$ is optionally substituted cycloalkyl, aryl or heterocycle; A$_2$ is optionally substituted cycloalkyl, aryl or heterocycle; R$_1$ is hydrogen, halogen, —OH, —NH$_2$, —NO$_2$, —CN, —C(O)OR$_4$, or optionally substituted alkyl; R$_2$ is hydrogen, halogen, —OH, —NH$_2$, —NO$_2$, —CN, —C(O)OR$_4$, or optionally substituted alkyl; each R$_3$ is independently =O or optionally substituted lower alkyl; each R$_4$ is independently hydrogen or lower alkyl; each R$_5$ is independently hydrogen, fluoro, hydroxyl or lower alkyl, provided that when one of R$_5$ is hydroxyl, the other is neither hydroxyl nor fluoro; n is 1-3; and m is 0-3 if n is 1, m is 0-4 if n is 2, or m is 0-5 if n is 3.

Some compounds of formula III are such that at least one of the following is true: 1) n is not 1; 2) A$_1$ is not optionally substituted phenyl; 2) A$_1$ is not optionally substituted cycloalkyl; 3) A$_2$ is not optionally substituted heterocycle; 4) R$_1$ is not cyano or lower alkyl; 5) R$_2$ is not cyano or lower alkyl; 6) R$_3$ is not oxo; 7) m is 0; 8) when n is 1, L$_1$ is a bond, and A$_1$ is optionally substituted phenyl, R$_3$ is not oxo; 9) L$_2$ is not —C(O)—; and/or 10) when n is 2, R$_1$ is methyl, R$_2$ is hydrogen, A$_1$ is pyridyl, and L$_2$ is —C(O)—, A$_2$ is not pyrrolidine.

Some compounds of the invention are of the formula:

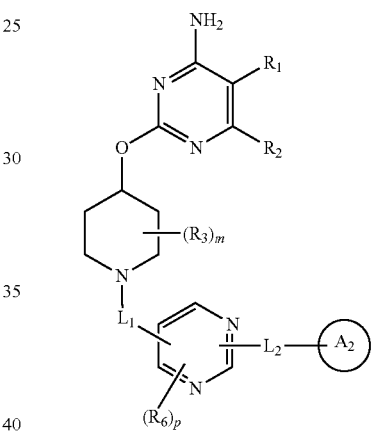

wherein: each R$_6$ is halogen, —OH, —NH$_2$, —NO$_2$, —CN, or optionally substituted alkyl; and p is 0-2.

Some are of the formula:

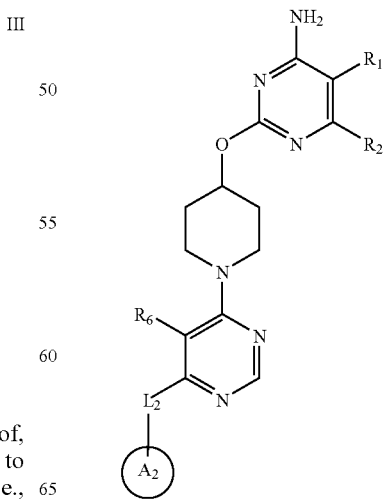

Others are of the formula:

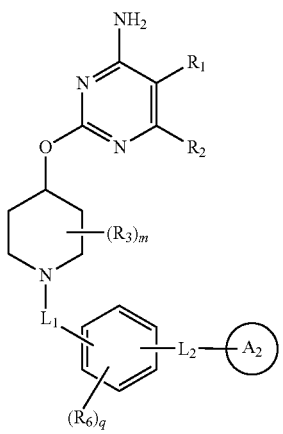

wherein: each R6 is halogen, —OH, —NH$_2$, —NO$_2$, —CN, or optionally substituted alkyl; and q is 0-4.

Some compounds are of the formula:

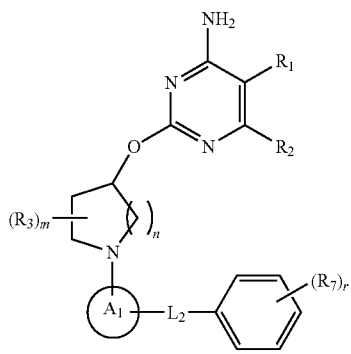

wherein: each R$_7$ is halogen, —OR$_8$, —NH$_2$, —NO$_2$, —C(O)N(R$_8$)$_2$, —CN, or optionally substituted alkyl, aryl or heterocycle; each R$_8$ is hydrogen or optionally substituted alkyl; and r is 0-5.

In some compounds encompassed by the various formulae disclosed herein, as applicable (i.e., the formulae having the particular variable discussed), L$_1$ is a bond. In others, L$_1$ is —C(O)— or —SO$_2$—. In others, L$_1$ is —C(R$_4$)$_2$— and, for example, at least one R$_4$ is hydrogen.

In some compounds, L$_2$ is a bond. In others, L$_2$ is —O—. In others, L$_2$ is —C(O)— or —C(NOH)—. In others, L$_2$ is —C(R$_5$)$_2$— and, for example, each R$_5$ is hydrogen or one R$_5$ is not hydrogen.

In some compounds, L$_1$ is a bond and L$_2$ is —O—.

In some compounds, A$_1$ is optionally substituted aryl (e.g., monocyclic aryl). In some, A$_1$ is optionally substituted phenyl or naphthyl. In others, A$_1$ is optionally substituted heterocycle (e.g., monocyclic heterocycle). In some, the heterocycle is aromatic; in others, it is not. In some, the heterocycle is optionally substituted imidazole, pyridine, pyrimidine, purine, triazine, or thiazole. In some, A$_1$ is optionally substituted with one or more of: alkyl (e.g., lower alkyl), alkoxy (e.g., lower alkoxy), amino, cyano, halogen, or hydroxy.

In some compounds, A$_2$ is optionally substituted aryl (e.g., monocyclic aryl). In some, the aryl is optionally substituted phenyl or naphthyl. In others, A$_2$ is optionally substituted heterocycle (e.g., monocyclic heterocycle). In some, the heterocycle is aromatic; in others, it is not. In some, the heterocycle is optionally substituted pyridine, quinoline, thiophene, indole, pyrazole, piperidine, morpholine, or pyrrolidine. In some, A$_2$ is optionally substituted with one or more of: alkyl (e.g., lower alkyl), alkoxy (e.g., lower alkoxy), amide, amino, cyano, halogen, hydroxy, sulfonamide or sulfone. In some, A$_2$ is substituted with an optionally substituted heterocycle (e.g., a non-aromatic heterocycle).

In some compounds, R$_1$ is hydrogen or halogen. In others, R$_1$ is —OH, —NH$_2$ or optionally substituted lower alkyl. In others, R$_1$ is —NO$_2$ or —CN.

In some compounds, R$_2$ is hydrogen or halogen. In others, R$_2$ is —OH, —NH$_2$ or optionally substituted lower alkyl. In others, R$_2$ is —NO$_2$ or —CN.

In some compounds, R$_1$ is halogen and R$_2$ is hydrogen.

In some compounds, R$_3$ is hydrogen.

In some compounds, m is 0.

In some compounds, n is 1. In others, n is 2. In others, n is 3.

Compounds of the invention may contain one or more stereocenters, and can exist as mixtures of enantiomers or diastereomers. This invention encompasses stereomerically pure forms of such compounds, as well as mixtures of those forms. Stereoisomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, 1N, 1972).

Preferred compounds are potent deoxycytidine kinase inhibitors. For example, particular compounds have a dCK_IC$_{50}$ of less than about 1000, 500, 250, 100, 50, 10, 5, 2.5 or 1 nM.

Particular compounds inhibit thymidine kinase with an IC$_{50}$ of greater than about 1, 2.5, 5 or 10 µM, as determined using the assay described in the Examples below.

Particular compounds inhibit uridine kinase with an IC$_{50}$ of greater than about 1, 2.5, 5 or 10 µM, as determined using the assay described in the Examples below.

5.3. Methods of Treatment

This invention encompasses a method of reducing (e.g., inhibiting) the activity of deoxycytidine kinase, which comprises contacting deoxycytidine kinase with a compound of the invention (i.e., a compound disclosed herein). In one embodiment, the deoxycytidine kinase is in vitro. In another, the deoxycytidine kinase is in vivo.

Also encompassed is a method of treating, managing or preventing cancer in a patient, which comprises inhibiting deoxycytidine kinase activity in the patient. A particular patient is undergoing chemotherapy.

One embodiment of the invention encompasses a method of treating, managing or preventing cancer in a patient, which comprises administering to the patient a therapeutically or prophylactically effective amount of a potent deoxycytidine kinase inhibitor. Particular potent deoxycytidine kinase inhibitors are disclosed herein. In one method, the potent deoxycytidine kinase inhibitor is administered adjunctively with another chemotherapeutic agent (e.g., cyclophosphamide or a combination comprising it, such as CHOP).

Cancers include solid cancers (e.g., colon carcinomas, brain tumors, head and neck tumors, malignant melanomas and soft tissue sarcomas), leukemia, and lymphoma.

Another embodiment of the invention encompasses a method of improving the effectiveness of a chemotherapeutic agent in a patient undergoing chemotherapy with the chemotherapeutic agent, which comprises inhibiting deoxycytidine kinase activity in the patient. Examples of chemotherapeutic agents include cyclophosphamide.

In each of these various methods, the amount, route of administration and dosing schedule of a compound will depend upon factors such as the specific indication to be treated, prevented, or managed, and the age, sex and condition of the patient. The roles played by such factors are well known in the art, suitable doses and dosing regimens can be determined by the skilled artisan.

5.4. Pharmaceutical Compositions

This invention encompasses pharmaceutical compositions and dosage forms comprising compounds of the invention as their active ingredients. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

6. EXAMPLES

The preparation of some compounds of the invention is described below. Methods used to determine biological activities of compounds are also described.

6.1. Chromatographic Conditions

Some of the following examples describe high performance liquid chromatography (HPLC) results. The HPLC conditions used to obtain those results are summarized in Table 1:

TABLE 1

| Mthd | Column | Solvent A | Solvent B | Time | Grad | Flow | Obs |
|---|---|---|---|---|---|---|---|
| A | Sunfire C18 5 u 4.6 × 50 mm | 10 mM NH$_4$OAc | CH$_3$CN | 2 | 10-90 | 3.5 | 220 |
| B | Sunfire C18 5 u 4.6 × 50 mm | 0.1% TFA in water | 0.1% TFA in MeOH | 2 | 10-90 | 3.5 | 220 |
| C | Sunfire C18 5 u 4.6 × 50 mm | 0.1% TFA in water | 0.1% TFA in MeOH | 2 | 10-90 | 4 | 220 |
| D | ShimPack VP-ODS 4.6 × 50 mm | 10 mM NH$_4$OAc | CH$_3$CN | 4 | 0-100 | 3 | 220 |
| E | ShimPack VP-ODS 4.6 × 50 mm | 0.1% TFA in water | 0.1% TFA in MeOH | 4 | 10-90 | 3 | 220 |
| F | Sunfire C18 5 u 4.6 × 50 mm | water | 0.1% TFA in MeOH | 6 | 30-80 | 3.5 | 220 |
| G | Sunfire C18 5 u 4.6 × 50 mm | water | 0.1% TFA in MeOH | 3 | 10-90 | 3.5 | 220 |
| H | Sunfire C18 5 u 4.6 × 50 mm | water | 0.1% TFA in MeOH | 2 | 10-90 | 3.5 | 220 |
| I | Sunfire C18 5 u 4.6 × 50 mm | water | 0.1% TFA in MeOH | 3 | 10-75 | 3.5 | 220 |
| J | Luna Phenylhexyl 5 u 4.6 × 50 mm | 10 mM NH$_4$OAc | CH$_3$CN | 8 | 10-90 | 2 | 220 |
| K | Sunfire C18 5 u 4.6 × 50 mm | 90:10 H$_2$O/MeOH with 0.1% TFA | 10:90 H$_2$O/MeOH with 0.1% TFA | 2 | 0-100 | 3.5 | 220 |
| L | ShimPack VP-ODS 4.6 × 50 mm | 10 mM NH$_4$OAc | CH$_3$CN | 4 | 10-90 | 3 | 220 |

TABLE 1-continued

| Mthd | Column | Solvent A | Solvent B | Time | Grad | Flow | Obs |
|---|---|---|---|---|---|---|---|
| M | Sunfire C18 5 u 4.6 × 50 mm | 10 mM NH$_4$OAc | CH$_3$CN | 2 | 10-90 | 3 | 220 |
| N | Luna Phenylhexyl 5 u 4.6 × 50 mm | 10 mM NH$_4$OAc | CH$_3$CN | 3 | 10-90 | 3 | 220 |
| O | Sunfire C18 5 u 4.6 × 50 mm | 10 mM NH$_4$OAc | CH$_3$CN | 3 | 0-100 | 3.5 | 220 |
| P | Sunfire C18 3.5 u 4.6 × 50 mm | 10 mM NH$_4$OAc | CH$_3$CN | 2.8 | 10-95 | 4.5 | 220 |
| Q | ShimPack VP-ODS 4.6 × 50 mm | 10 mM NH$_4$OAc | CH$_3$CN | 8 | 10-90 | 3 | 220 |
| R | Sunfire C18 5 u 4.6 × 50 mm | 10 mM NH$_4$OAc | CH$_3$CN | 4 | 10-90 | 3.5 | 220 |
| S | Luna Phenylhexyl 5 u 4.6 × 50 mm | 10 mM NH$_4$OAc | CH$_3$CN | 3 | 5-100 | 3 | 220 |
| T | Luna Phenylhexyl 5 u 4.6 × 50 mm | 10 mM NH$_4$OAc | CH$_3$CN | 8 | 5-100 | 3 | 220 |
| U | Sunfire C18 5 u 4.6 × 50 mm | 10 mM NH$_4$OAc | CH$_3$CN | 3 | 5-100 | 3.5 | 220 |
| V | Sunfire C18 5 u 4.6 × 50 mm | 10 mM NH$_4$OAc | CH$_3$CN | 2 | 5-100 | 3.5 | 220 |
| W | Sunfire C18 5 u 4.6 × 50 mm | 10 mM NH$_4$OAc | CH$_3$CN | 3 | 20-90 | 3.5 | 220 |
| X | Sunfire C18 5 u 4.6 × 50 mm | 10 mM NH$_4$OAc | CH$_3$CN | 3 | 5-100 | 3.5 | 220 |
| Y | Sunfire C18 5 u 4.6 × 50 mm | 10 mM NH$_4$OAc | CH$_3$CN | 3 | 10-90 | 3.5 | 220 |
| Z | Sunfire C18 5 u 4.6 × 50 mm | 10 mM NH$_4$OAc | CH$_3$CN | 3 | 5-90 | 3.5 | 220 |
| AA | Sunfire C18 5 u 4.6 × 50 mm | 90:10 H$_2$O/MeOH with 0.1% TFA | 10:90 H$_2$O/MeOH with 0.1% TFA | 3 | 5-100 | 3.5 | 220 | wherein: Mthd is the method; Flow is the flow rate in ml/min; Time is the gradient duration in minutes; Grad is the solvent gradient (percent B); and Obs is the observation wavelength in nm.

6.2. General Method A

Preparation of 5-fluoro-2-(piperidin-4-yloxy)pyrimidin-4-amine (4)

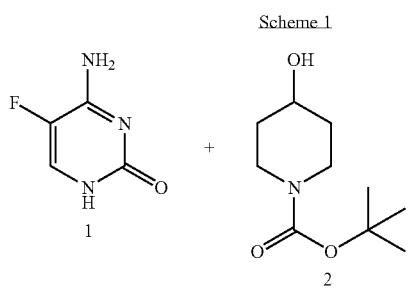

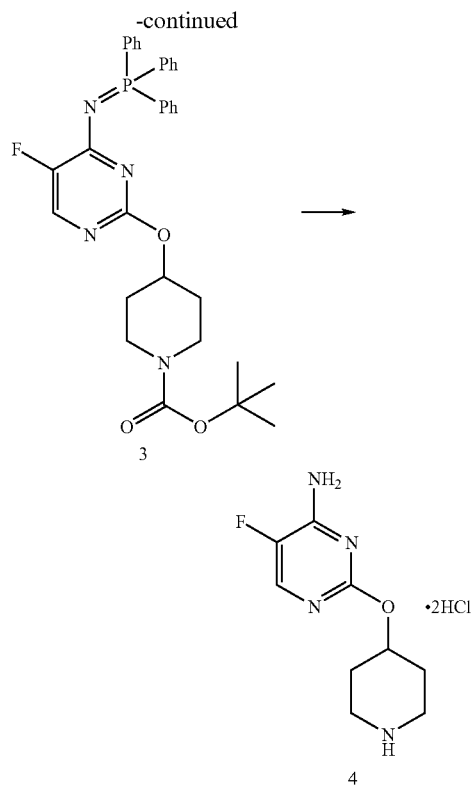

A general synthetic approach referred to herein as General Method A was used to prepare the captioned compound.

In this exemplification, a 500 mL round bottom flask fitted with stirbar was charged with 1 (13.00 g 100 mmol), 2 (10.0 g, 49.7 mmol), triphenylphosphine (19.6 g, 74.6 mmol) and anhydrous THF (1 L). To this mixture was added, via syringe, diethyl diazene-1,2-dicarboxylate (DEAD; 13.0 g, 74.6 mmol). The reaction mixture was stirred at ambient temperature for 18 h under $N_2$ atmosphere. Precipitate was filtered off and filtrate preabsorbed onto silica gel and passed through a plug of silica gel, eluting with EtOAc Hexanes 1:4. Recovered 25 g crude 3 which was taken on for deprotection.

To a 1 L round bottom flask charged with 25 g of 3 was added 200 ml EtOH and 50 mL conc. HCl. The reaction was stirred at ambient temperature for 18 h. Evaporated in vacuo and the residue partitioned between 1:1 EtOAc:$Et_2O$ and water. Organics were extracted 3 times with water and combined aqueous layers were evaporated in vacuo and dried to afford a white solid (8.3 g, 59% yield).

Using this procedure 3-pyrrolidinol and azepan-4-ol react with 2 to form common intermediate 5-fluoro-2-(pyrrolidin-3-yloxy)pyrimidin-4-amine and 5-Fluoro-2-(-(azepan-4-yloxy)pyrimidin-4-amine respectively.

6.3. General Method B

Preparation of 5-fluoro-2-(piperidin-4-yloxy)pyrimidin-4-amine (4)

A general synthetic approach referred to herein as General Method B was used to prepare the captioned compound.

In this exemplification, to a 250 mL 3-neck round bottom flask was charged 5 (7.38 g, 50 mmol), 2 (20.13 g, 2.0 equiv), NaO-t-Bu (9.61 g, 2.0 equiv) and diglyme (100 mL) and the mixture was heated at 120° C. for 18 h. The mixture was then cooled to 50° C. and $H_2O$ (100 mL) was added. The mixture was extracted with EtOAc (200 mL) and washed with a mixture of $H_2O$ (50 mL) and brine (50 mL) twice. The organic layer was dried over $MgSO_4$ and concentrated under vacuum. The residue was then purified by silica gel column chromatography using hexanes:EtOAc (2:1) to give the title compound 6 as a white solid (9.05 g, 58% yield).

Removal of the Boc group was accomplished as described in General Method A.

Scheme 2 can also be employed when the 4-Hydroxy-piperidine has already been N-capped.

6.4. General Method C

Preparations of 5-fluoro-2-(1-(5-fluoro-6-(4-methoxyphenoxy)-pyrimidin-4-yl)piperidin-4-yloxy)pyrimidin-4-amine (10) and 2-(6-(4-(4-amino-5-fluoropyrimidin-2-yloxy)piperidin-1-yl)pyrimidin-4-yloxy)benzonitrile (14) (Schemes 3 & 4)

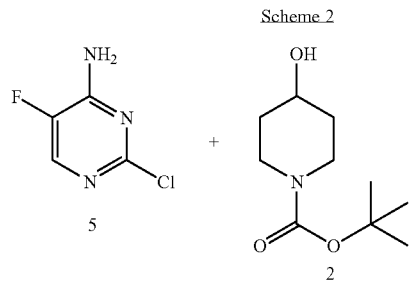

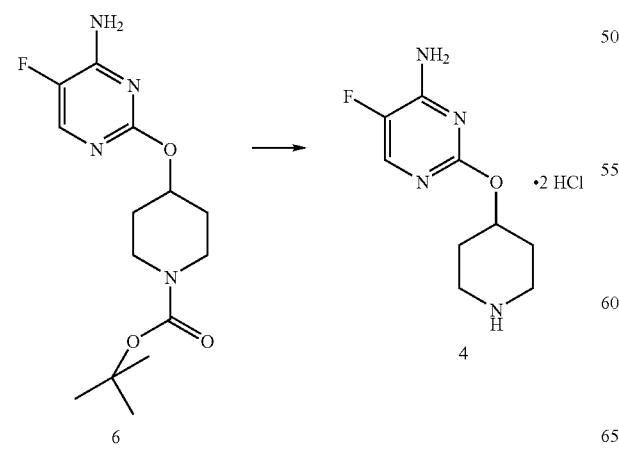

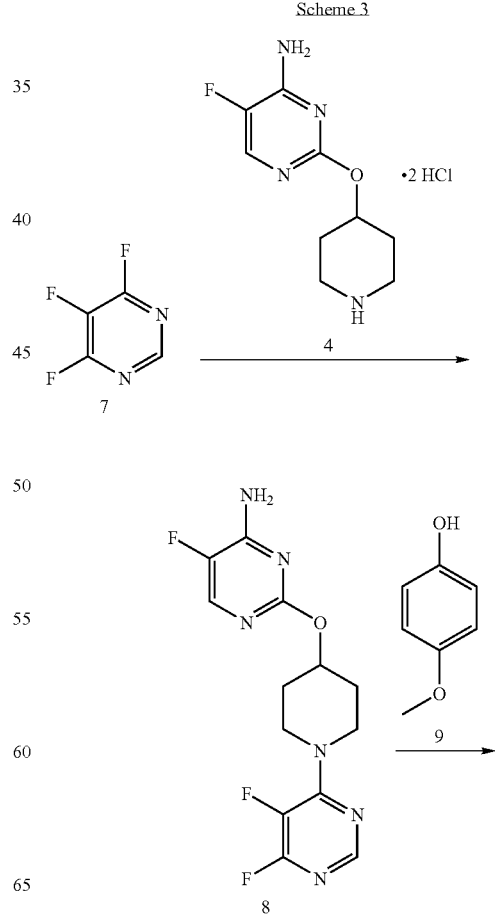

-continued

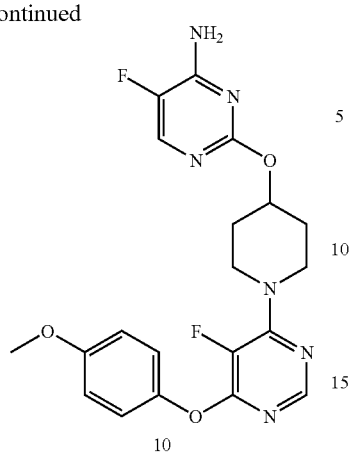

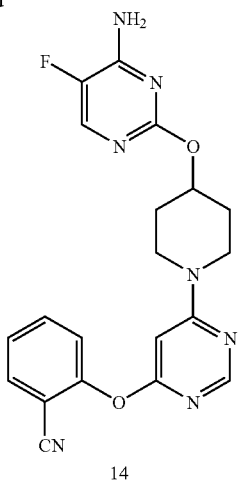

A general synthetic approach referred to herein as General Method C was used to prepare the captioned compound.

In this exemplification, to a 50 mL round bottom flask fitted with a stirbar and charged with 7 (280 mg, 2.1 mmol) in n-BuOH cooled to 0° C. was added N,N-diisopropylethylamine (DIEA) (1 mL, 6.3 mmol) and 4. The reaction was stirred at 0° C. for 1 hr. The reaction mixture was allowed to warm to room temperature and evaporated in vacuo and purified on a plug of SiO$_2$. A white solid 8 was recovered (640 mg, 83% yield) which was taken on without further purification.

Crude 8 (100 mg, 0.31 mmol) was added to a microwave vial along with 2 mL of anhydrous DMF, 9 (76 mg, 0.31 mmol) and NaH (25 mg, 062 mmol). The mixture was heated in the microwave for 10 min at 160° C. (75 W). The crude reaction mixture was evaporated in vacuo and the residue treated with MeOH and water. The solids were filtered off, washed with water and dried to afford product 10 (47 mg, 35% yield).

This procedure is a two-step, one pot process. A microwave vial was charged with 11 (500 mg, 3.36 mmol), 12 (400 mg, 3.36 mmol) and K$_2$CO$_3$ (464 mg, 3.36 mmol) in DMF (5 mL) and was heated to 100° C. for 5 minutes in the microwave. The aryl ether 13 was generated as a stable intermediate and was carried on without further isolation and purification. An aliquot (3 mL, 2.01 mmol) of the reaction mixture was syringed over to a new microwave vial to which was added DIEA (1 mL, 5.74 mmol) and 4 (630 mg, 2.22 mmol) and the reaction was heated to 200° C. for 10 minutes under microwave irradiation. The reaction mixture was evaporated in vacuo and the residue was dissolved in MeOH and water was added until the solution became cloudy. After sitting over night, the solid was filtered off, dissolved in hot MeOH and warm water was added until cloudy. Let sit overnight and filtered off white solid 14 (154 mg, 19% yield).

In a similar fashion other nucleophiles (alcohols, anilines, etc) and bases can be used.

Intermediates similar to 8, 10, 13 and 14 were synthesized as outlined above and served as starting materials for other methods.

6.5. General Method D

Preparation of 4-amino-1-(1-(2,3-dichlorophenylsulfonyl)piperidin-4-yl)-5-fluoropyridin-2(1H)-one (16)

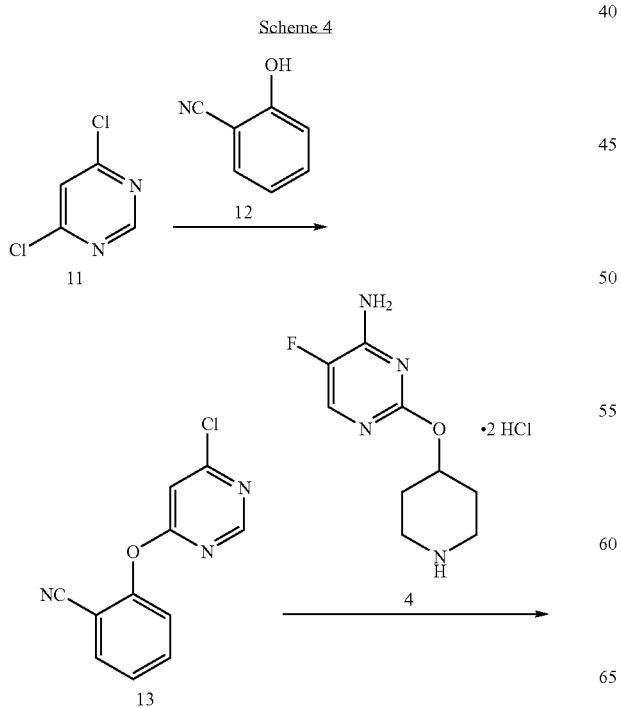

Scheme 4

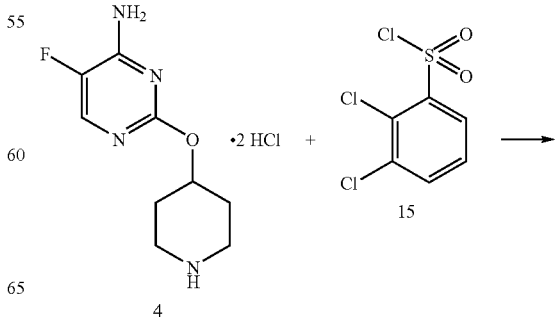

Scheme 5

-continued

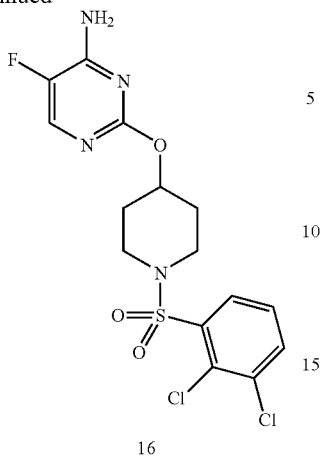

16

A general synthetic approach referred to herein as General Method D was used to prepare the captioned compound.

In this exemplification, compound 4 (60 mg, 0.21 mmol) and DIEA (0.1 mL, 0.63 mmol) were mixed in DCM (2 mL). Compound 15 (62 mg, 0.25 mmol, 1.2 eq) was then added. The mixture was stirred at room temperature for 1 hour. The product was isolated by evaporation in vacuo followed by purification using reverse phase HPLC (aqueous ammonium acetate/acetonitrile). Isolated product 16 as a white solid (32 mg, 36% yield).

6.6. General Method E

Preparation of (4-(4-amino-5-fluoropyrimidin-2-yloxy)piperidin-1-yl)(2-(4-methoxyphenoxy)phenyl)methanone (18)

Scheme 6

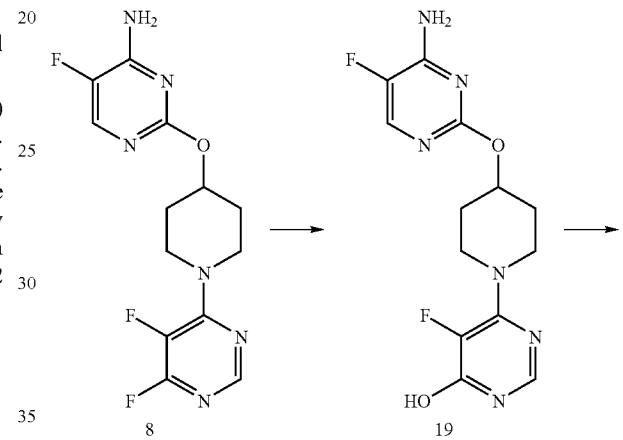

A general synthetic approach referred to herein as General Method E was used to prepare the captioned compound.

In this exemplification, compound 17 (100 mg, 0.25 mmol), 9 (47.12 mg, 0.38 mmol), Tetrakis(acetonitrile)copper(I) hexafluorophosphate (4.7 mg, 0.013 mmol), and $Cs_2CO_3$ (163 mg, 0.50 mmol) were mixed in 1,4-dioxane (1 mL). The reaction mixture was heated under microwave irradiation at 180° C. for 10 minutes. The reaction mixture was purified by preparative HPLC (aqueous ammonium acetate/acetonitrile). Isolated 18 as a white solid (1.5 mg, 1% yield).

6.7. General Method F

Preparation of 2-(1-(6-chloro-5-fluoropyrimidin-4-yl)piperidin-4-yloxy)-5-fluoropyrimidin-4-amine (20)

Scheme 7

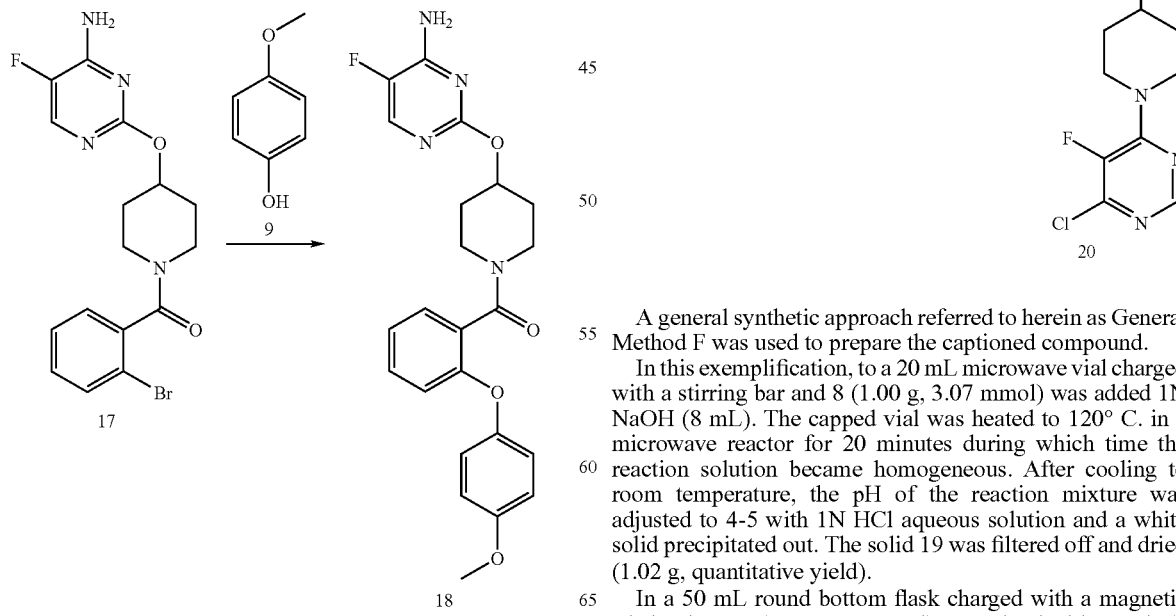

A general synthetic approach referred to herein as General Method F was used to prepare the captioned compound.

In this exemplification, to a 20 mL microwave vial charged with a stirring bar and 8 (1.00 g, 3.07 mmol) was added 1N NaOH (8 mL). The capped vial was heated to 120° C. in a microwave reactor for 20 minutes during which time the reaction solution became homogeneous. After cooling to room temperature, the pH of the reaction mixture was adjusted to 4-5 with 1N HCl aqueous solution and a white solid precipitated out. The solid 19 was filtered off and dried (1.02 g, quantitative yield).

In a 50 mL round bottom flask charged with a magnetic stirring bar, 19 (0.324 g, 1 mmol) was mixed with $POCl_3$ (2 mL). The mixture was heated to 110° C. and refluxed for 2 hours. After cooling down, POCl$_3$ was removed in vacuo, and the residue was dissolved in EtOAc (50 mL) and 5% NaHCO$_3$ (20 mL). After shaking and separation, the organic phase was dried over Na$_2$SO$_4$. Removal of the solvent gave a yellow solid as product 20 (0.284 g, 83% yield).

6.8. General Method G (6-(4-(4-amino-5-fluoropyrimidin-2-yloxy)piperidin-1-yl)pyrimidin-4-yl)(5-chloroindolin-1-yl)methanone (25)

Scheme 8

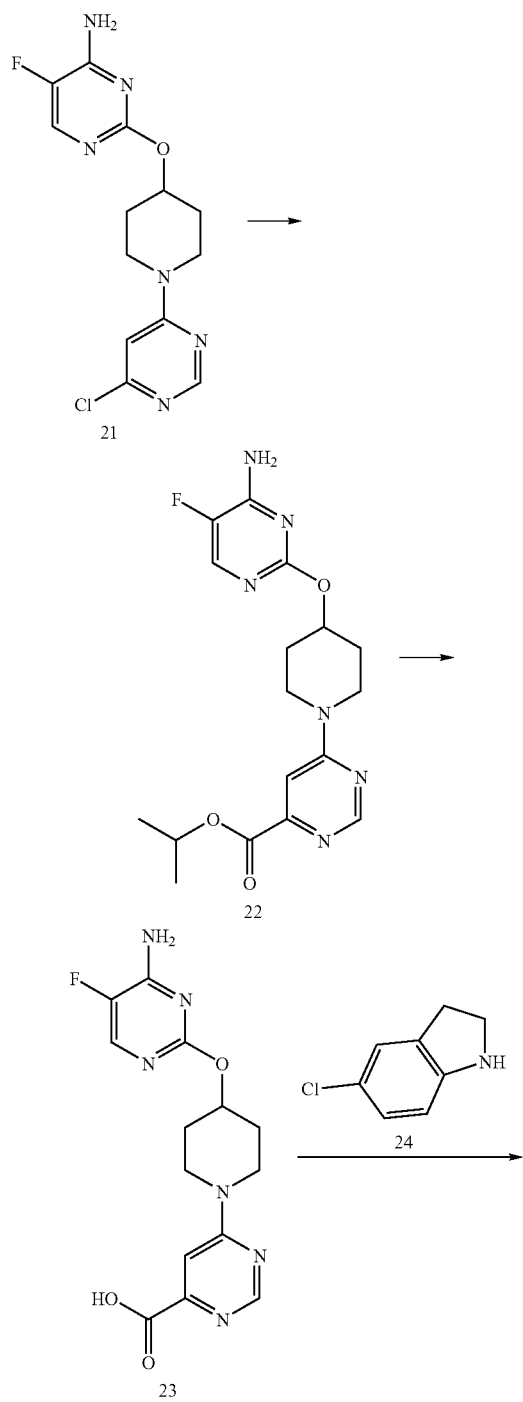

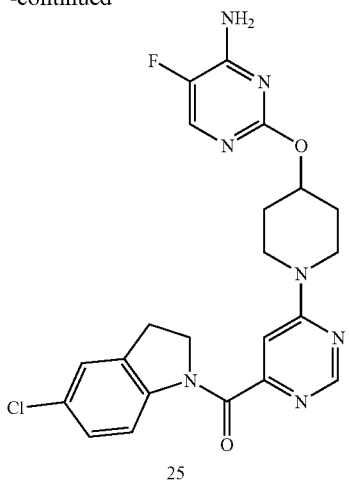

A general synthetic approach referred to herein as General Method G was used to prepare the captioned compound.

In this exemplification, to a pre-dried Schlenk flask charged with a magnetic stirring bar and 21 (1.0 g, 3.09 mmol) and K$_2$CO$_3$ (0.64 g, 4.63 mmol) was added a solution of iso-propanol (30 mL, anhydrous) and DMF (6 mL, anhydrous). After degassing for 10 minutes by flowing N$_2$ through the solution, Pd(OAc)$_2$ (0.070 g, 0.31 mmol) and DPPP (0.140 g, 0.34 mmol) were added. After vacuum evacuation of the flask and flushing with CO (3 times), CO (1 atm) was applied to reaction. Reaction mixture was heated to 80° C. and for 18 h. After cooling to room temperature, the solvent was removed in vacuo. The residue was transferred to a separatory funnel using DCM and water. After extraction and separation, the aqueous layer was washed with 50 mL of DCM. The organic layers were combined and solvent removed. The residue was purified by silica gel column (4:96 MeOH:DCM). Removal of the solvent in vacuo gave a white solid product 22. (0.992 g, 85% yield).

In a 100 mL round bottom flask charged with a stirring bar, 22 (0.99 g, 2.63 mmol) was stirred in THF (10 mL) and water (10 mL). 3M NaOH (3 mL, 9 mmol) was added. The reaction mixture was heated to 50° C. and stirred for 2 hours. After cooling to room temperature the reaction mixture was adjusted to pH 5. Most of solvent was removed in vacuo and a precipitate formed. The precipitate was filtered off and washed twice with a small amount of water. Drying of the white solid under high vacuum gave 23 (0.796 g, 91% yield).

In a 40 mL vial with a magnetic stirring bar, 23 (0.083 g, 0.246 mmol) was mixed with 24 (74 mg, 0.492 mmol) and triethylamine (0.050 g, 0.492 mmol) in DMF (10 mL). 2-(1H-7-Azabenzotriazol-1-yl)-1,1,3,3-tetramethyl uronium hexafluorophosphate methanaminium (HATU) (0.140 g, 0.369 mmol) was then added and the reaction was stirred at room temperature for 2 hours. Then solvent was removed in vacuo. The residue was dissolved in DCM and washed with water. The organic phase was concentrated in vacuo and the residue was purified by silica gel chromatography (0 to 10% MeOH in DCM) to give a white solid 25 (64 mg, 56% yield).

6.9. General Method H

Preparation of (4-(4-amino-5-fluoropyrimidin-2-yloxy)piperidin-1-yl)(biphenyl-4-yl)methanone (27)

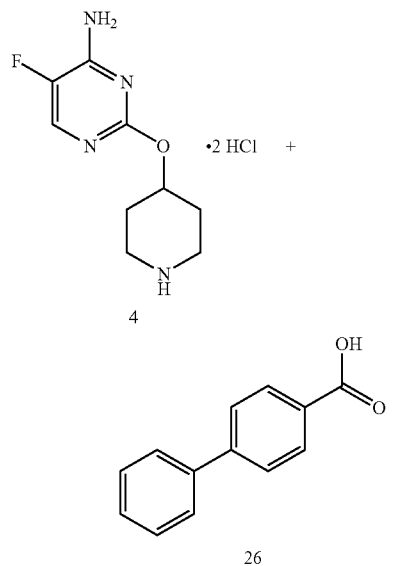

Scheme 9

A general synthetic approach referred to herein as General Method H was used to prepare the captioned compound.

In this exemplification, to a suspension of 26 (198 mg, 1.0 mmol) in anhydrous DCM (10 mL) was added oxalyl chloride (185 uL, 2.12 mmol) and the reaction was stirred at room temperature until complete conversion to acid chloride was observed. The reaction was evaporated in vacuo and azeotroped with toluene. The residue was dissolved in acetonitrile and added slowly to a suspension of 4 (225.0 mg, 1.06 mmol) in acetonitrile (10 mL) and sat. NaHCO$_3$ (5 mL), then stirred vigorously for 18 h. Evaporated in vacuo and partitioned between DCM and 0.5 N NaOH. The organic layer was washed with water and brine, dried with Na$_2$SO$_4$ and evaporated in vacuo. Purified by preparative HPLC (aqueous ammonium acetate/acetonitrile). Recovered a white solid 27 (21 mg, 5.5% yield).

6.10. General Method I

Preparation of 1-(4-(4-amino-5-fluoropyrimidin-2-yloxy)piperidin-1-yl)-2-(naphthalen-2-ylamino)ethanone (29)

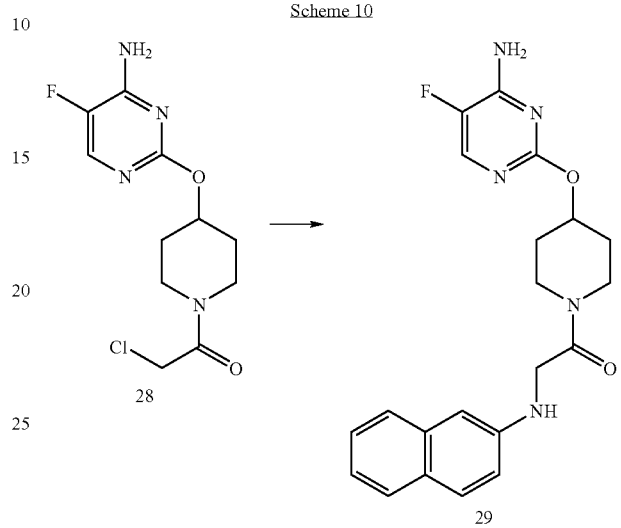

Scheme 10

A general synthetic approach referred to herein as General Method I was used to prepare the captioned compound.

In this exemplification, compound of 28 was synthesized using General Method H. Compound 29 was synthesized using an appropriate amine and General Method D.

6.11. General Method J

Preparation of 5-fluoro-2-(1-(3-(4-methoxyphenoxy)propyl)piperidin-4-yloxy)pyrimidin-4-amine (30)

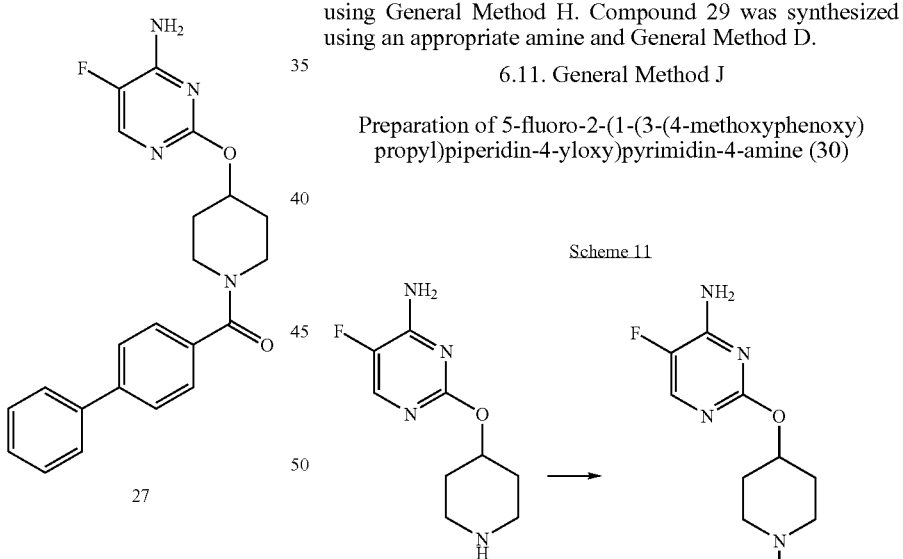

Scheme 11

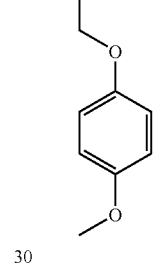

A general synthetic approach referred to herein as General Method J was used to prepare the captioned compound.

In this exemplification, compound 30 was synthesized using General Method C and the appropriate alkyl halide.

6.12. General Method K

Preparation of (6-(4-(4-amino-5-fluoropyrimidin-2-yloxy)piperidin-1-yl)pyrimidin-4-yl)(4-methoxyphenyl)methanone (34)

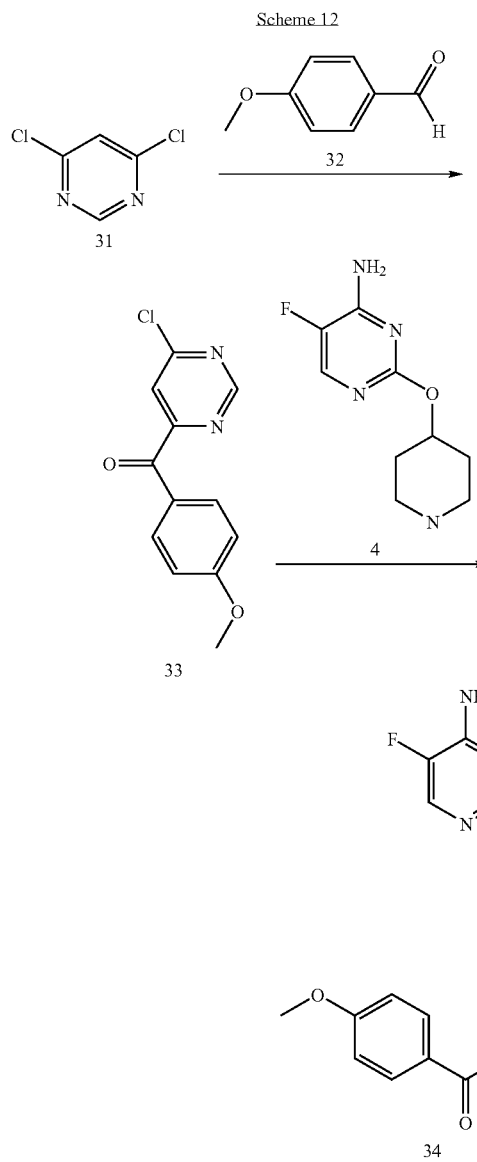

A general synthetic approach referred to herein as General Method K was used to prepare the captioned compound.

In this exemplification, compound 31 (338 mg, 2.27 mmol), 32 (273 uL, 2.25 mmol), 1-butyl-3-methylimidazolium tetrafluoroborate (150 mg, 0.66 mmol) and THF (20 ml) were mixed well at RT in a round bottom flask, NaH (60% in mineral oil, 117 mg, 2.92 mmol) was then added. The resulting solution was stirred at RT for 0.5 hour. The reaction was loaded onto SiO$_2$ and purified by column chromatography (0 to 1% MeOH in DCM). Recovered 33 as a solid (40 mg, 7% yield).

Compound 33 (40 mg 0.16 mmol), 4 (60 mg, 0.21 mmol), excess DIEA and DMF (2 mL) were combined and mixed well in a 2 mL microwave vial and heated in the microwave at 180° C. for 10 minutes. Product was isolated by evaporation in vacuo followed by purification on preparative HPLC (aqueous ammonium acetate/acetonitrile). Isolated 34 as a white solid (29 mg, 42% yield).

6.13. General Method L

Preparation of 2-(1-(6-(difluoro(4-methoxyphenyl)methyl)pyrimidin-4-yl)piperidin-4-yloxy)-5-fluoropyrimidin-4-amine (35)

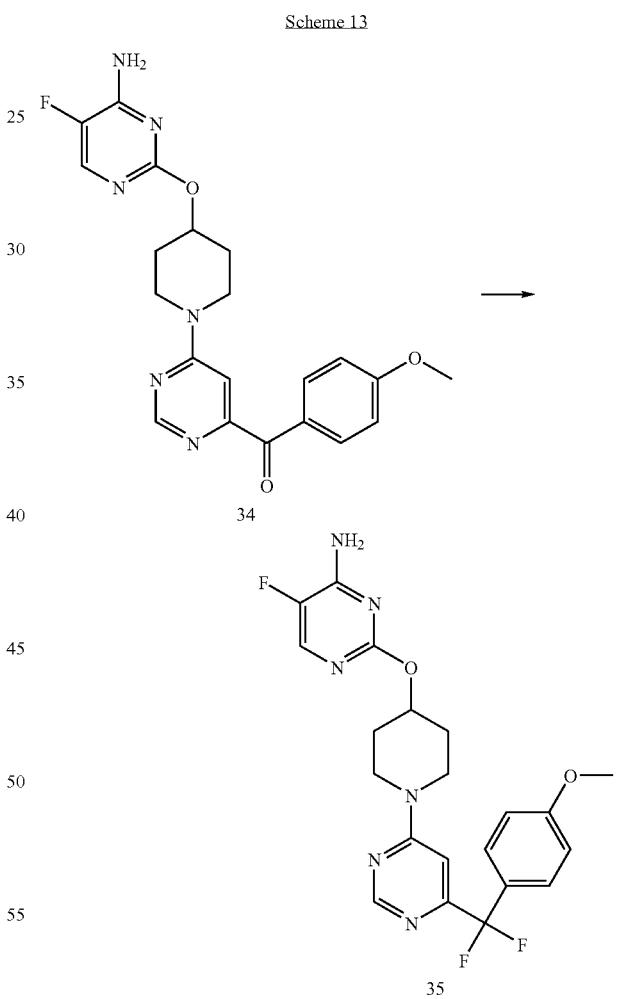

A general synthetic approach referred to herein as General Method L was used to prepare the captioned compound.

In this exemplification, compound 34 (20 mg, 0.094 mmol) was dissolved in DCM (2 mL), (Diethylamino)sulfur trifluoride (148 uL 0.113 mmol) was added. The reaction mixture was refluxed for 3 hrs and then filtered through silica gel, washing with 8% MeOH/DCM. Concentrated by evaporation in vacuo and purified by reverse phase HPLC (aqueous ammonium acetate/acetonitrile) to give 35 as a white solid (4.76 mg, 10% yield).

6.14. General Method M

Preparation of (6-(4-(4-amino-5-fluoropyrimidin-2-yloxy)piperidin-1-yl)pyrimidin-4-yl)(4-methoxyphenyl)methanol (36)

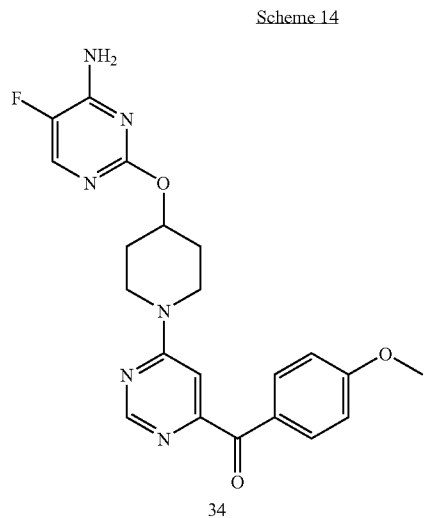

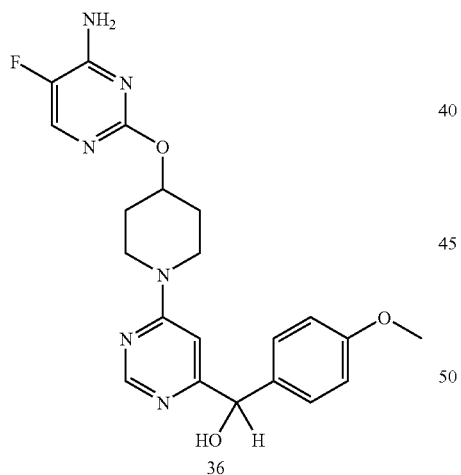

A general synthetic approach referred to herein as General Method M was used to prepare the captioned compound.

In this exemplification, compound 34 (16 mg, 0.038 mmol) was dissolved in 1 mL MeOH, NaBH₄ (1.7 mg, 0.045 mmol) was added and the reaction was stirred at room temperature for 0.5 hour. The reaction mixture was treated with a small amount of H₂O, then purified by reverse phase HPLC (aqueous ammonium acetate/acetonitrile). Recovered 36 as a white solid (6.8 mg, 42% yield).

6.15. General Method N

Preparation of (E)-(6-(4-(4-amino-5-fluoropyrimidin-2-yloxy)piperidin-1-yl)pyrimidin-4-yl)(4-methoxyphenyl)methanone oxime (37)

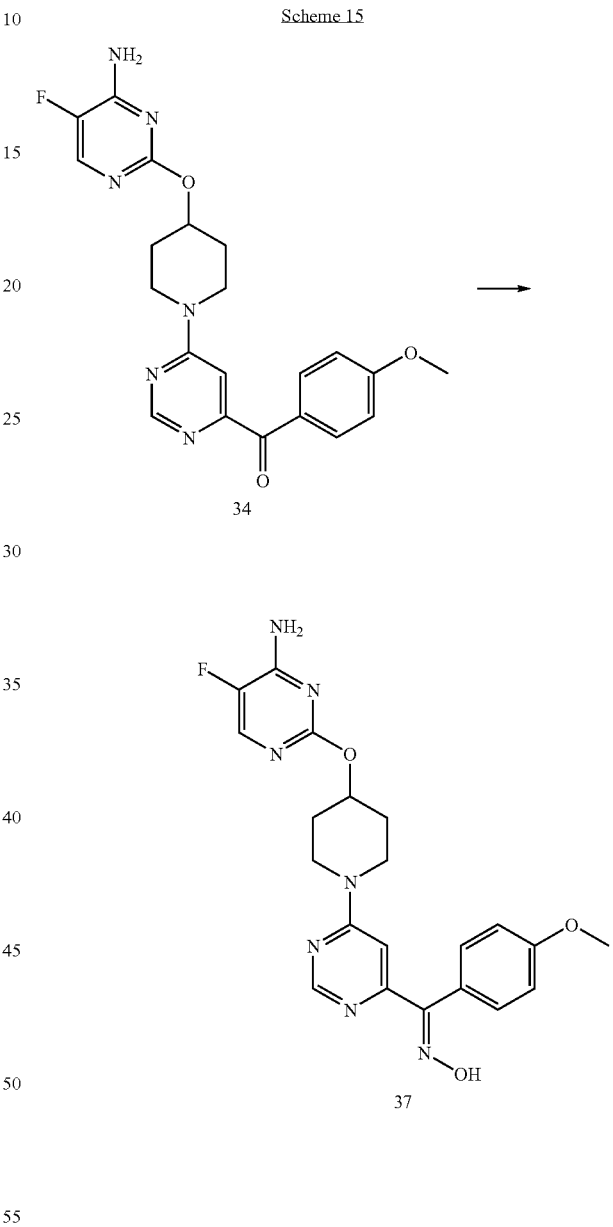

A general synthetic approach referred to herein as General Method N was used to prepare the captioned compound.

In this exemplification, compound 34 (115 mg 0.27 mmol), hydroxylamine hydrochloride (37 mg, 0.54 mmol), NaOAc (2.0 uL, 21 wt % in EtOH, 0.54 mmol, 2 eq) were combined in 1:1 EtOH/THF (4 ml) and stirred at 50° C. for 0.5 hour. The reaction mixture was concentrated in vacuo and purified on SiO₂ (4 to 5% MeOH in DCM). Treatment with MeOH (6 ml) precipitated the product, which was filtered and washed with MeOH. Isolated a white solid 37 (19 mg, 16% yield).

6.16. General Method O

Preparation of 2-(2-(6-(4-(4-amino-5-fluoropyrimidin-2-yloxy)piperidin-1-yl)pyrimidin-4-yloxy)phenyl)propan-2-ol (39)

6.17. General Method P

Preparation of 5-fluoro-2-(1-(6-(2-(1-methyl-1H-pyrazol-4-yl)phenoxy)pyrimidin-4-yl)piperidin-4-yloxy)pyrimidin-4-amine (41)

Scheme 16

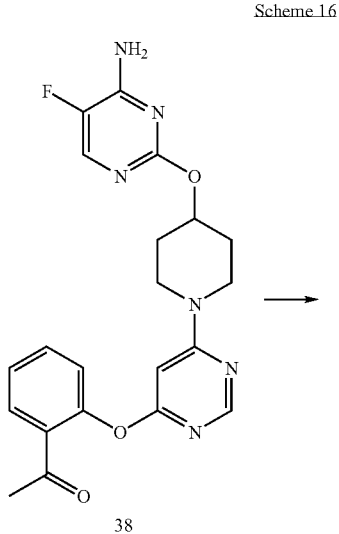

Scheme 17

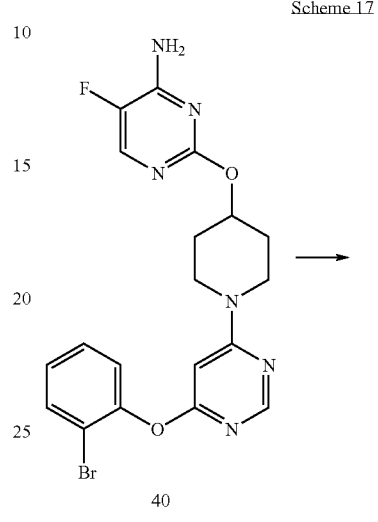

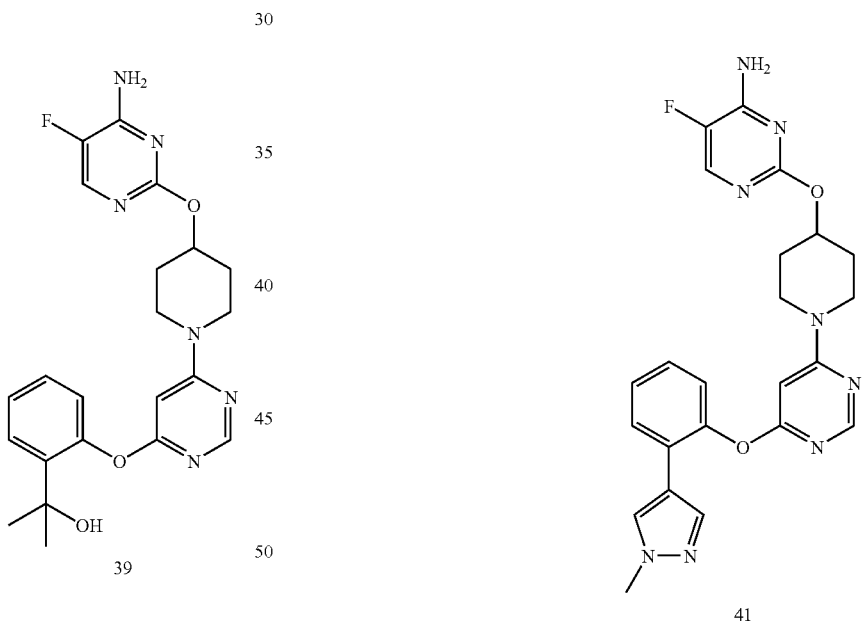

A general synthetic approach referred to herein as General Method O was used to prepare the captioned compound.

In this exemplification, to a cooled (ice bath) solution of ketone 38 (848 mg, 2 mmol) in THF (20 mL) was added methyl magnesium bromide solution in ether (2.5 mL, 3 M, 7.5 mmol). The reaction was warmed to RT slowly over 1 h then stirred at RT for 3 hours before quenching with saturated ammonium chloride. The product was extracted into ethyl acetate, dried over sodium sulfate and concentrated to a yellow foam. The crude foam was purified by reverse phase HPLC (aqueous ammonium acetate/acetonitrile) to give a white solid 39 (36 mg, 4% yield).

A general synthetic approach referred to herein as General Method P was used to prepare the captioned compound.

In this exemplification, to a solution of 40 (42 mg, 0.09 mmol) in ethanol (4 mL) was added 1-methyl-pyrazoleboronic ester (37 mg, 0.18 mmol) followed by 2 N sodium carbonate (0.4 mL, 0.4 mmol) and Pd(dppf)Cl$_2$·CH$_2$Cl$_2$ (8 mg, 0.01 mmol). The reaction was sealed and heated under microwave irradiation at 100° C. for 10 min. The reaction was filtered and purified by reverse phase HPLC (aqueous ammonium acetate/acetonitrile) to yield a white solid 41 (20 mg, 48% yield).

6.18. General Method Q

Preparation of 5-Fluoro-2-[1-(5-oxa-2,4-diaza-dibenz[a,d]-cyclohepten-1-yl)-piperidin-4-yloxy]-pyrimidin-4-ylamine (43)

Scheme 18

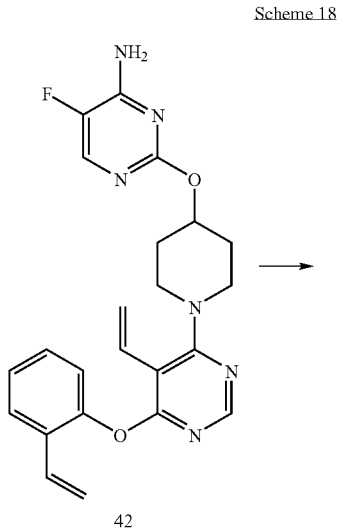

6.19. General Method R

Preparation of 2-(1-(5-amino-6-(4-methoxyphenoxy)pyrimidin-4-yl)piperidin-4-yloxy)-5-fluoropyrimidin-4-amine (45)

Scheme 19

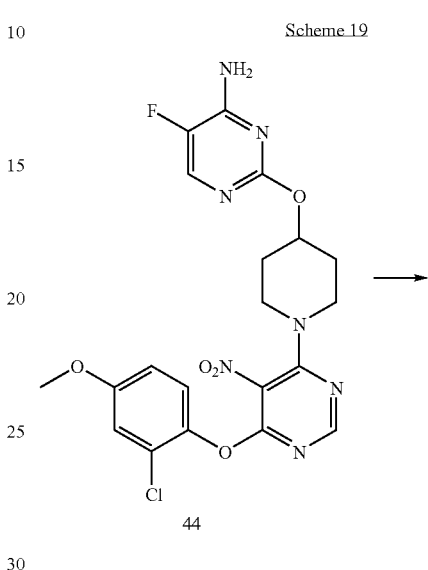

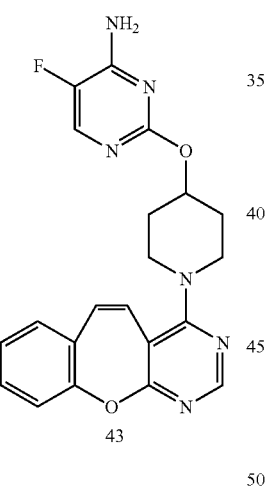

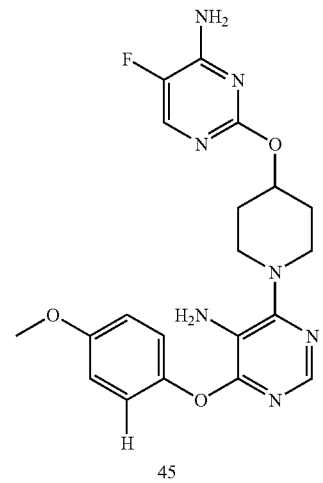

A general synthetic approach referred to herein as General Method Q was used to prepare the captioned compound.

In this exemplification, a solution of 42 (0.064 g, 0.147 mmol) in trifluorotoluene (3 mL) and 1,2-dichloroethane (3 mL) was treated with (1,3-Bis-(2,4,6-trimethylphenyl)-2-imidazolidinylidene)dichloro(phenylmethylene)(tricyclohexylphosphine)ruthenium (0.001 g, 0.001 mmol). The mixture was heated under microwave irradiation at 160° C. for 20 minutes. The mixture was concentrated in vacuo, loaded on silica gel, and chromatographed (10 g $SiO_2$, 4:6 hexane/ethyl acetate to ethyl acetate), followed by reverse phase HPLC (aqueous ammonium acetate/acetonitrile) to afford 43 as a white solid (0.002 g, 3% yield).

A general synthetic approach referred to herein as General Method R was used to prepare the captioned compound.

In this exemplification, compound 44 (180 mg, 0.37 mmol) was sealed in a Parr vessel with 10% Pd—C (20 mg) and ethanol (5 mL) and stirred under a hydrogen atmosphere of 10 psi for 30 minutes. The reaction mixture was filtered and purified by reverse phase HPLC($CH_3CN$, 0.1% formic acid in $H_2O$) to give 45 (4 mg, 2.5% yield).

6.20. General Method S

Preparation of 2-(1-(2-benzyl-2H-tetrazol-5-yl)piperidin-4-yloxy)-5-fluoropyrimidin-4-amine (48)

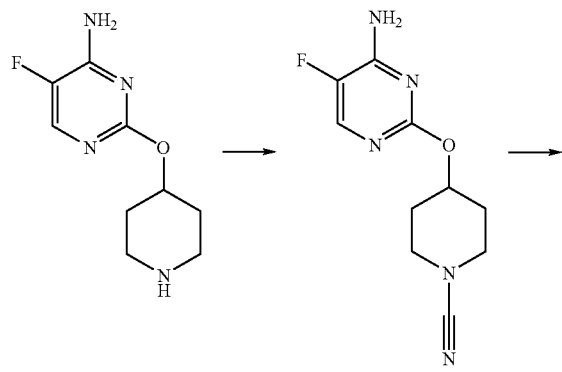

A general synthetic approach referred to herein as General Method S was used to prepare the captioned compound.

In this exemplification, compound 4 (500 mg, 1.8 mmol) and potassium carbonate (975 mg, 7.1 mmol) were stirred in DMF (10 mL) while cyanogen bromide (187 mg, 1.8 mmol) in DMF (1.5 mL) was added. After 1 hour, water (100 mL) was added and a pale yellow solid formed. The solid was collected by filtration to afford the cyanamide 46 (237 mg, 56% yield).

Compound 46 (225 mg, 0.95 mmol) was suspended in 1:1 water/iso-propanol (6 mL). Sodium azide (124 mg, 1.9 mmol) and zinc bromide (427 mg, 1.9 mmol) were added. The mixture was heated to reflux, capped, vented, and then heated at 140° C. under microwave irradiation for 30 min. The reaction was acidified with 1 M HCl and purified on reverse phase HPLC (0.1% TFA in water; 0.1% TFA in MeOH) to afford the desired tetrazole 47 (253 mg, 96% yield).

The tetrazole 47 (50 mg, 0.18 mmol) obtained above was dissolved in ethanol (8 mL), water (3 mL) and 1M NaOH (196 uL, 0.196 mmol). 2-(bromomethyl)-benzonitrile (35 mg, 0.18 mmol) was added and the reaction heated to reflux. After 18 hours another portion of 1M NaOH (196 uL, 0.196 mmol) and 2-(bromomethyl)-benzonitrile (35 mg, 0.18 mmol) was added. After another 24 hours, the product was purified by reverse phase HPLC (0.1% formic acid in water; 0.1% formic acid in MeOH) to afford the desired product 48 (10 mg, 14% yield).

6.21. General Method T

Preparation of 2-(1-(6-(4-(2-(dimethylamino)ethoxy)$_p$henoxy)pyrimidin-4-yl)piperidin-4-yloxy)-5-fluoropyrimidin-4-amine (50)

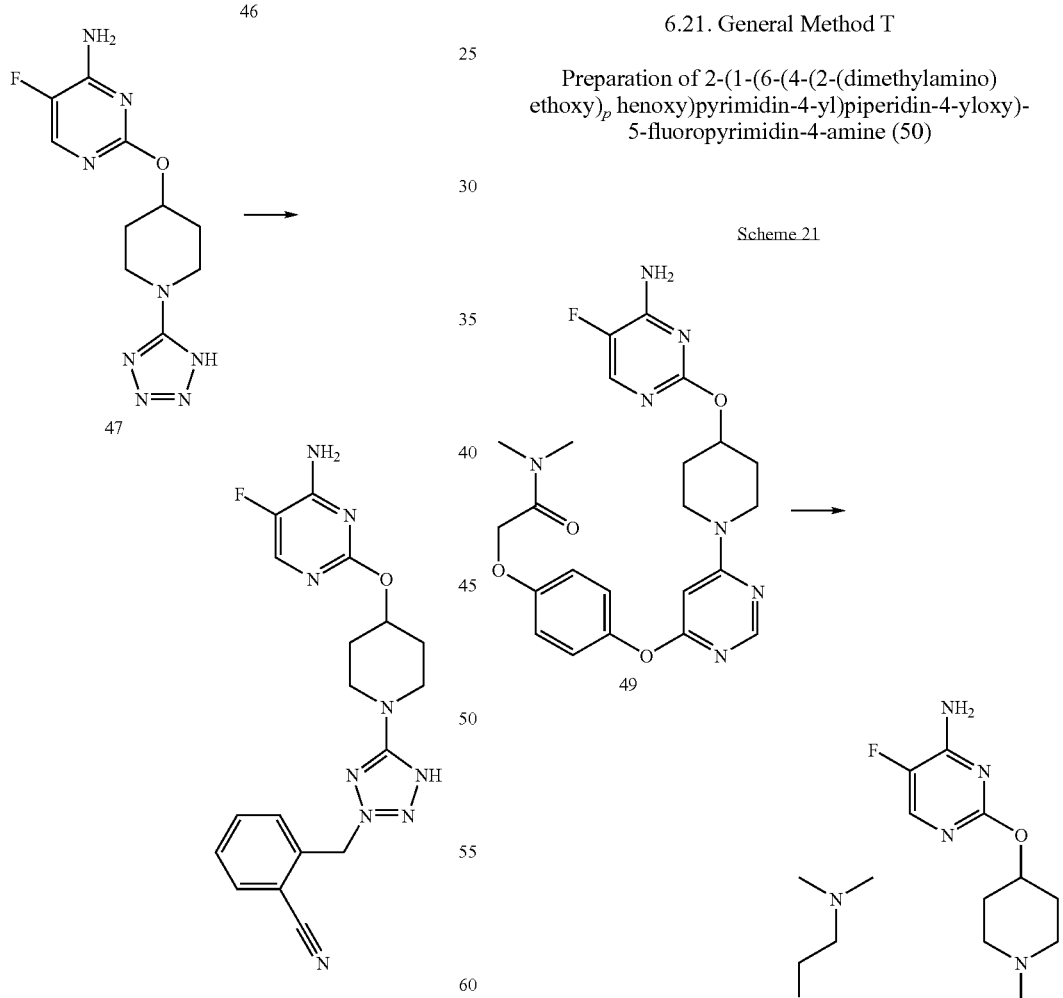

A general synthetic approach referred to herein as General Method T was used to prepare the captioned compound.

In this exemplification, in a pre-dried 25 mL round bottom flask charged with a magnetic stirring bar, amide 49 (0.050 g, 0.1 mol) was dissolved in 3 mL of THF. Lithium aluminum hydride (1M solution in THF, 0.2 mL, 0.2 mmol) was added to the reaction which was stirred at room temperature for half an hour. Upon completion, the reaction was quenched by consecutive additions of water (7 μL), 3 N NaOH (7 μL) and water (21 μL). The reaction mixture was allowed to stir for 10 minutes. The precipitate was filtered the filtrate was concentrated. The crude residue purified by preparative HPLC (acetonitrile/aqueous ammonium acetate) to give product 50 (10 mg, 22% yield).

6.22. General Method U

Preparation of 5-fluoro-2-(1-(6-phenylpyrimidin-4-yl)piperidin-4-yloxy)pyrimidin-4-amine (51)

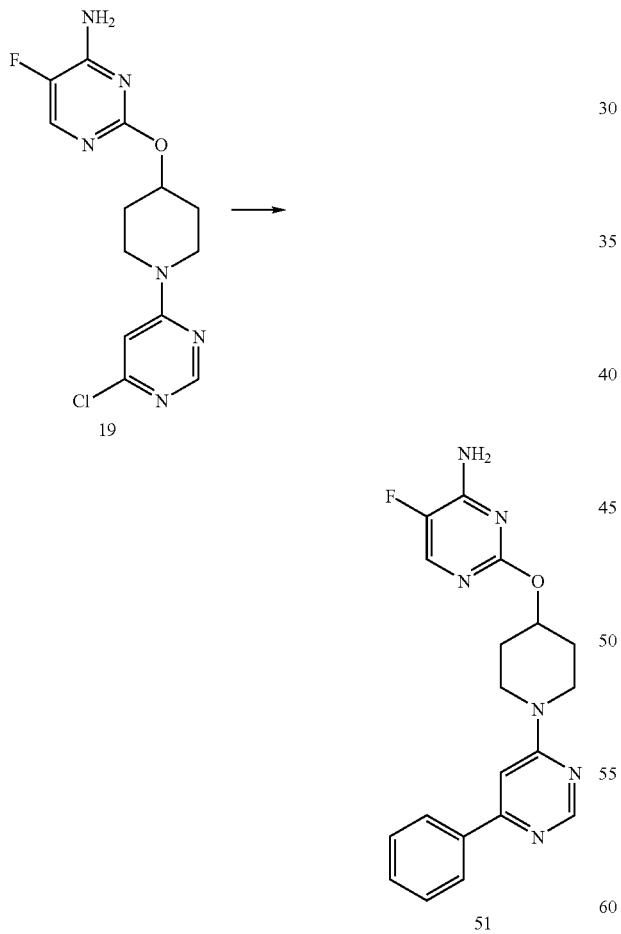

6.23. General Method V

Preparation of (4-(4-amino-5-fluoropyrimidin-2-yloxy)piperidin-1-yl)(5-(benzo[b]thiophen-2-yl)-2-fluorophenyl)methanone (53)

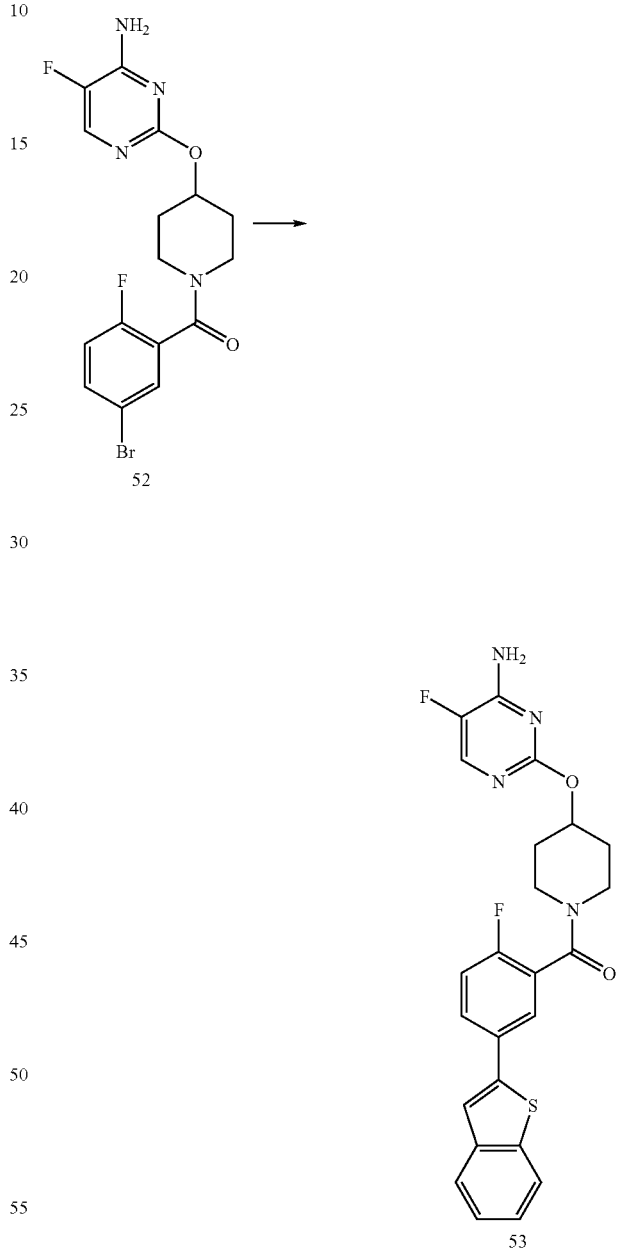

A general synthetic approach referred to herein as General Method U was used to prepare the captioned compound.

In this exemplification, compound 51 was synthesized using General Method P.

A general synthetic approach referred to herein as General Method V was used to prepare the captioned compound.

In this exemplification, compound 53 was synthesized using General Methods H and P.

6.24. General Method W

Preparation of N-(6-(4-(4-amino-5-fluoropyrimidin-2-yloxy)piperidin-1-yl)pyrimidin-4-yl)benzamide (56)

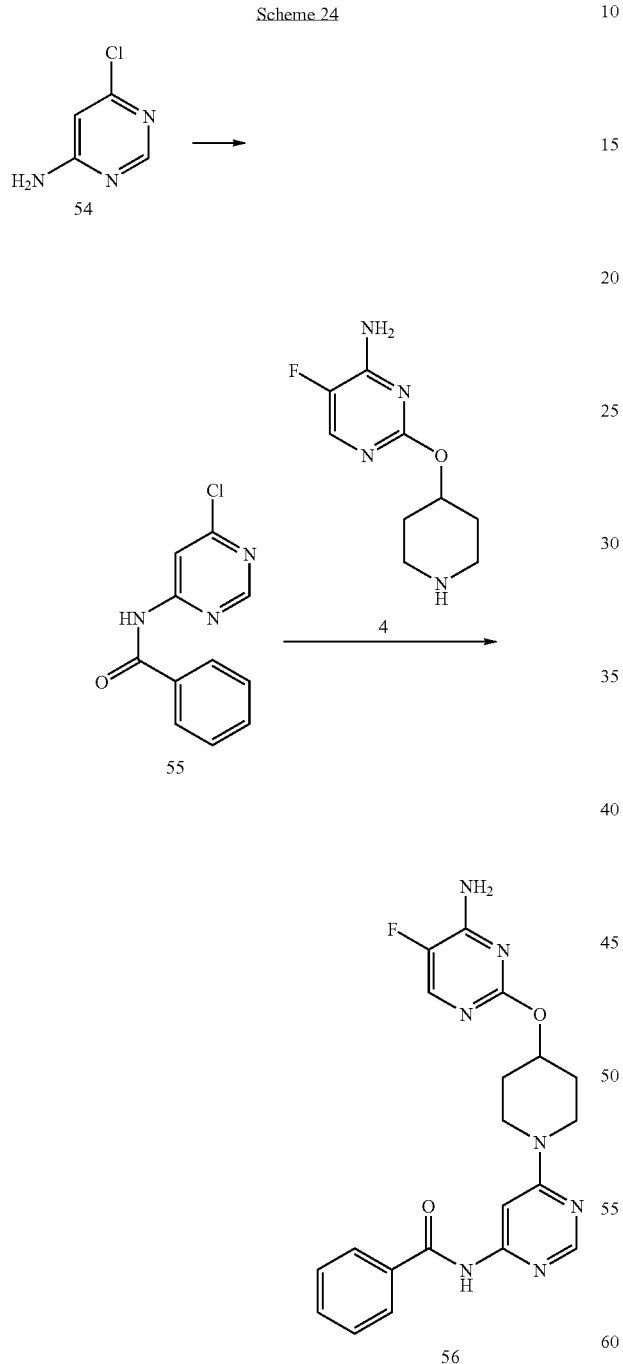

Scheme 24

A general synthetic approach referred to herein as General Method W was used to prepare the captioned compound.

In this exemplification, compound 56 was synthesized using General Method H followed by General Method C.

6.25. General Method X

Preparation of 2-(1-(6-(4-((cyclopropylamino)methyl)-2-methoxyphenoxy)-5-fluoropyrimidin-4-yl)piperidin-4-yloxy)-5-fluoropyrimidin-4-amine (58)

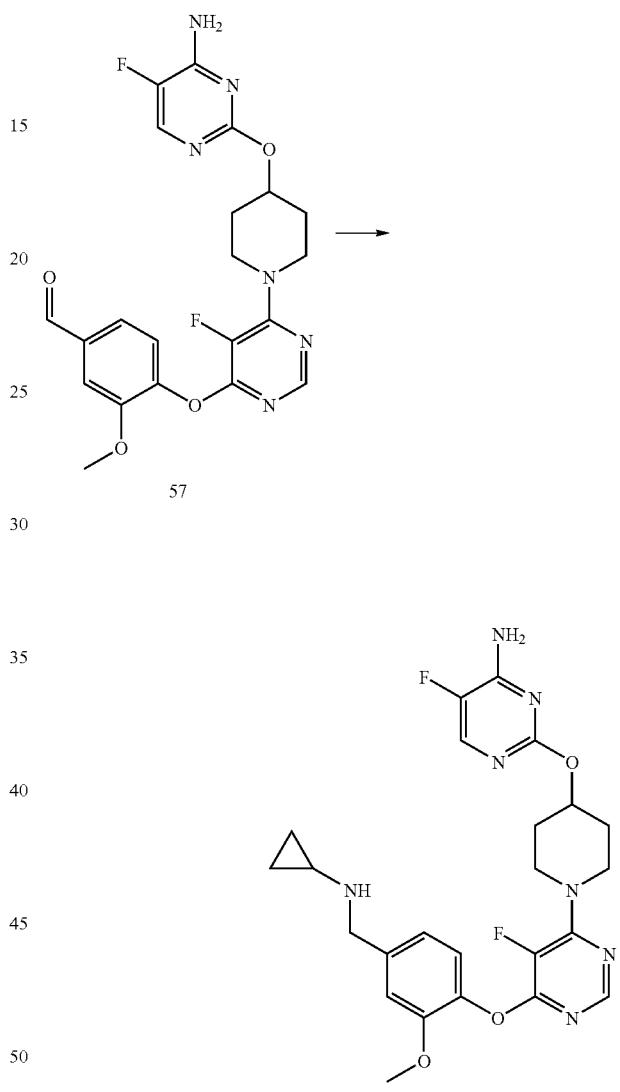

Scheme 25

A general synthetic approach referred to herein as General Method X was used to prepare the captioned compound.

In this exemplification, aldehyde 57 (50 mg, 0.11 mmol), sodium triacetoxyborohydride (116 mg, 0.55 mmol) and cyclopropylamine (32 mg, 0.55 mmol) were stirred in acetonitrile (3 mL) for 18 hours at room temperature. The reaction mixture was filtered and purified by reverse phase HPLC (CH$_3$CN, 0.1% Formic Acid in H$_2$O) to give product 58 (25 mg, 46% yield)

6.26. General Method Y

Preparation of 3-(6-(4-(4-amino-5-fluoropyrimidin-2-yloxy)piperidin-1-yl)-5-fluoropyrimidin-4-yloxy)-5-methoxybenzonitrile (60)

Scheme 26

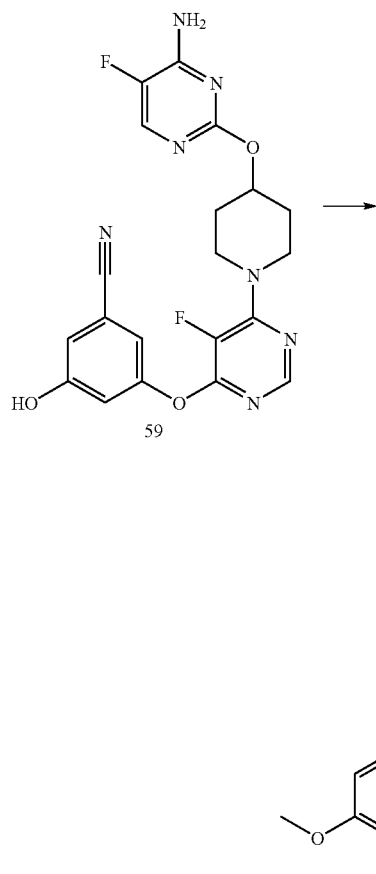

A general synthetic approach referred to herein as General Method Y was used to prepare the captioned compound.

In this exemplification, the phenol 59 (25 mg, 0.06 mmol) was stirred in acetone (3 mL) with potassium carbonate (39 mg, 0.28 mmol). A few drops of methyl iodide (excess) were added to the reaction mixture which was left to stir for 1 hour at room temperature. The mixture was concentrated and purified by HPLC(CH$_3$CN, 0.1% formic acid in H$_2$O) to give the final product 60 (14 mg, 51% yield).

6.27. General Method Z

Preparation of 2-(1-(6-(difluoro(2-fluoro-4-methoxyphenyl)methyl)pyrimidin-4-yl)piperidin-4-yloxy)-5-fluoropyrimidin-4-amine (63)

Scheme 27

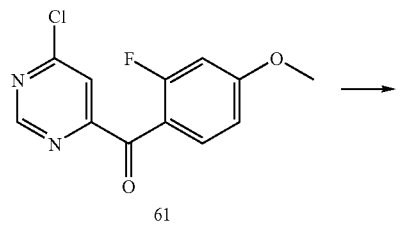

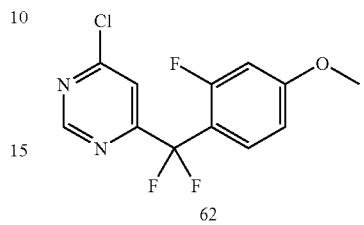

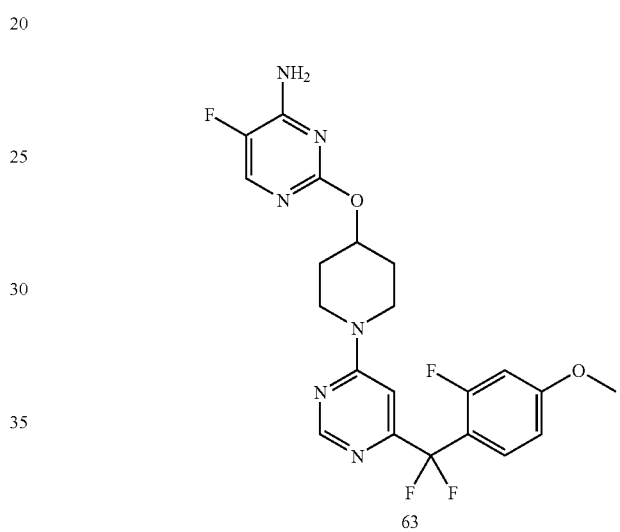

A general synthetic approach referred to herein as General Method Z was used to prepare the captioned compound.

In this exemplification, compound 61 (100 mg 0.38 mmol) was dissolved in DCM and (diethylamino)sulfur trifluoride (148 uL, 0.113 mmol) was added. The reaction mixture was refluxed for 8 hrs. Additional (diethylamino)sulfur trifluoride (148 uL, 0.113 mmol) was added and reflux resumed for 18 hours. Removed solvent in vacuo and crude product 62 (200 mg) was used without further purification in the following step.

Half of the above crude reaction mixture was mixed with 4 (40 mg, 0.14 mmol), DIEA (80 uL) in DMF (1 mL) and heated under microwave irradiation at 180° C. for 10 minutes. This reaction was repeated using the remaining amount of the crude 62. The two reaction mixtures were combined and diluted with EtOAc, washed with H$_2$O three times. Organic solvent was removed in vacuo, the residue was purified by preparative HPLC with neutral mobile phase (aqueous ammonium acetate/acetonitrile). Isolated 63 as a light brown solid (40 mg, 31% yield).

6.28. General Method AA

Preparation of 3-(6-(4-(4-amino-5-fluoropyrimidin-2-yloxy)piperidin-1-yl)-5-fluoropyrimidine-4-carbonyl)benzonitrile (65)

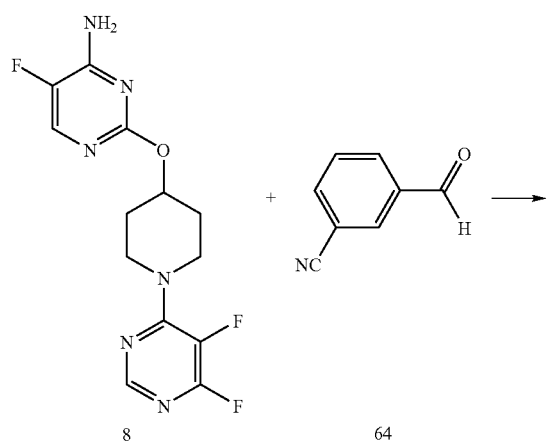

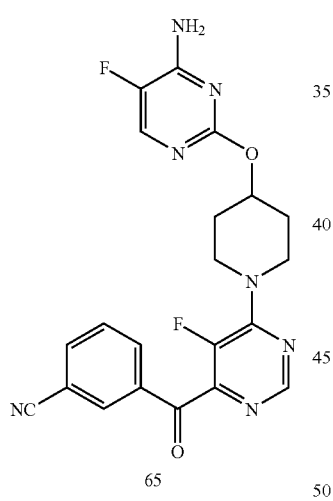

A general synthetic approach referred to herein as General Method AA was used to prepare the captioned compound.

In this exemplification, compound 8 200 mg 0.61 mmol), 64 (80 mg, 0.61 mmol), 1-butyl-3-methylimidazolium tetrafluoroborate (27 uL, 0.12 mmol) and THF (3 mL) were mixed in a microwave reaction vial, NaH (60% in mineral oil; 24 mg 0.61 mmol) was then added. The reaction mixture was heated in the microwave at 170° C. for 10 minutes. The desired product was purified by reverse phase HPLC (aqueous ammonium acetate/acetonitrile). Recovered 65 as a white solid (41 mg, 15% yield).

6.29. General Method BB

Preparation of 2-(1-(6-(3,5-difluorobenzyl)pyrimidin-4-yl)piperidin-4-yloxy)-5-fluoropyrimidin-4-amine (67)

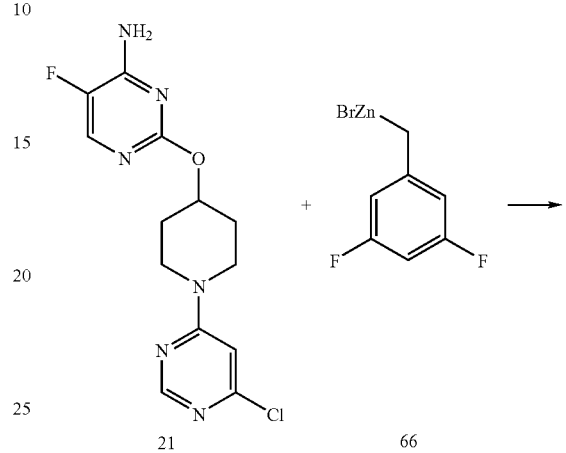

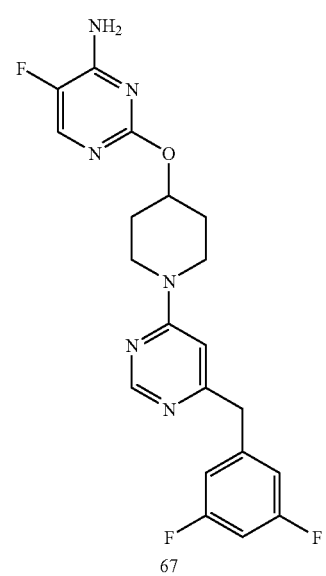

A general synthetic approach referred to herein as General Method BB was used to prepare the captioned compound.

In this exemplification, compound 21 (contained about 20% DIEA.HCl salt, 60 mg, about 0.15 mmol), (3,5-difluorobenzyl)zinc(II) bromide in THF (2 ml, 0.5 M, 1 mmol), and [1,1'-Bis(diphenylphosphino)ferrocene]dichloropalladium (II) complex with $CH_2Cl_2$ (20 mg) were mixed well and heated at 120° C. for 20 minutes. Purified by SiO₂ (2-5% MeOH in DCM). Recovered 67 as a white solid (15 mg, 24% yield).

6.30. General Method CC

Preparation of 4-[4-(4-Amino-5-fluoro-pyrimidin-2-yloxy)-piperidin-1-yl]-6-(4-methoxy-phenoxy)-pyrimidine-5-carbonitrile (69)

Scheme 30

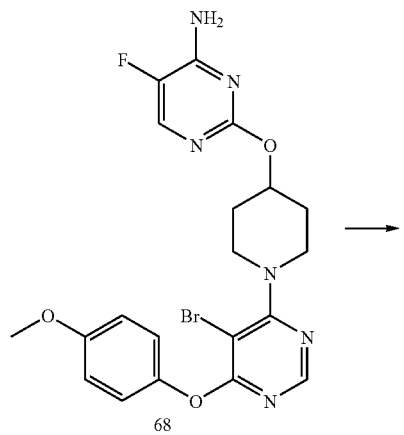

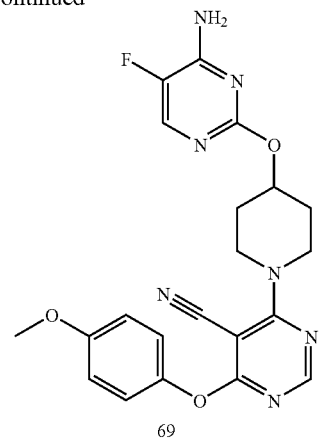

A general synthetic approach referred to herein as General Method CC was used to prepare the captioned compound.

In this exemplification, to a microwave vial charged with 68 (100 mg, 0.20 mmol) and zinc cyanide (24 mg, 0.20 mmol) was added Pd(PPh₃)₄ (7 mg, 0.006 mmol) in DMF (1 mL). The vial was flushed with nitrogen, sealed and heated at 220° C. for 20 min, after which time additional zinc cyanide (50 mg, 0.42 mmol) and Pd(PPh₃)₄ (15 mg, 0.013 mmol) were added. The vial was again flushed with nitrogen, sealed and heated at 220° C. for 20 min. The resulting suspension was filtered, concentrated to dryness and redissolved in CH₂Cl₂ and MeOH. The solution was passed through a plug of silica, concentrated to dryness and purified by reverse phase HPLC (aqueous ammonium acetate/acetonitrile) to afford 69 (13 mg, 0.030 mmol, 15% yield).

6.31. Additional Compounds

Additional compounds of the invention are listed below in Table 2, along with information concerning the general methods (Mthd) used for their preparation, the measured masses of the compounds (M+1), HPLC information [method (retention time in minutes)], and, in some cases, a reference to NMR information provided in Table 3.

TABLE 2

| Compound | Mthd | M + 1 | HPLC | NMR |
| --- | --- | --- | --- | --- |
| 4-Amino-2-{1-[6-(5-cyano-2-methoxy-phenoxy)-5-fluoro-pyrimidin-4-yl]-piperidin-4-yloxy}-pyrimidine-5-carbonitrile | B | 461.5 | Y (2.27) | 1 |
| 2-{1-[6-(3,5-Difluoro-benzyl)-pyrimidin-4-yl]-piperidin-4-yloxy}-5-fluoro-pyrimidin-4-ylamine | BB | 417.1 | A (1.70) | — |
| 2-[1-(6-Benzyl-pyrimidin-4-yl)-piperidin-4-yloxy]-5-fluoro-pyrimidin-4-ylamine | BB | 381.2 | A (1.59) | 2 |
| 2-{1-[6-(2-Ethyl-phenoxy)-pyrimidin-4-yl]-piperidin-4-yloxy}-5-fluoro-pyrimidin-4-ylamine | C | 411.1 | B (1.91) | — |
| 2-{1-[6-(3-Ethyl-biphenyl-4-yloxy)-pyrimidin-4-yl]-piperidin-4-yloxy}-5-fluoro-pyrimidin-4-ylamine | C | 487.1 | B (2.09) | — |
| 2-{1-[6-(2-Ethyl-4-fluoro-phenoxy)-pyrimidin-4-yl]-piperidin-4-yloxy}-5-fluoro-pyrimidin-4-ylamine | C | 429.1 | B (1.86) | — |
| 5-Fluoro-2-{1-[6-(4-methoxy-phenoxy)-pyrimidin-4-yl]-piperidin-4-yloxy}-pyrimidin-4-ylamine | C | 413.0 | B (1.52) | — |
| 2-{1-[6-(3-Ethyl-phenoxy)-pyrimidin-4-yl]-piperidin-4-yloxy}-5-fluoro-pyrimidin-4-ylamine | C | 411.2 | B (1.80) | — |

TABLE 2-continued

| Compound | Mthd | M + 1 | HPLC | NMR |
|---|---|---|---|---|
| 2-{1-[6-(3-Chloro-phenoxy)-pyrimidin-4-yl]-piperidin-4-yloxy}-5-fluoro-pyrimidin-4-ylamine | C | 417.0 | B (3.07) | 3 |
| 2-{1-[6-(4-Ethyl-phenoxy)-pyrimidin-4-yl]-piperidin-4-yloxy}-5-fluoro-pyrimidin-4-ylamine | C | 411.1 | B (3.07) | — |
| 2-{1-[6-(2-Ethyl-cyclohexyloxy)-pyrimidin-4-yl]-piperidin-4-yloxy}-5-fluoro-pyrimidin-4-ylamine | C | 417.0 | D (3.00/3.13) | — |
| 5-Fluoro-2-[1-(6-p-tolyloxy-pyrimidin-4-yl)-piperidin-4-yloxy]-pyrimidin-4-ylamine | C | 397.0 | B (1.65) | — |
| 2-{1-[6-(2-Chloro-phenoxy)-pyrimidin-4-yl]-piperidin-4-yloxy}-5-fluoro-pyrimidin-4-ylamine | C | 417.0 | M (1.72) | — |
| 2-{1-[6-(4-Chloro-phenoxy)-pyrimidin-4-yl]-piperidin-4-yloxy}-5-fluoro-pyrimidin-4-ylamine | C | 417.0 | M (1.79) | — |
| 5-Fluoro-2-{1-[6-(3-methoxy-phenoxy)-pyrimidin-4-yl-piperidin-4-yloxy}-pyrimidin-4-ylamine | C | 413.0 | M (1.61) | — |
| 2-{1-[6-(2-Ethoxy-phenoxy)-pyrimidin-4-yl]-piperidin-4-yloxy}-5-fluoro-pyrimidin-4-ylamine | C | 427.0 | B (1.89) | — |
| 2-{1-[6-(4-Chloro-2-methyl-phenoxy)-pyrimidin-4-yl-piperidin-4-yloxy}-5-fluoro-pyrimidin-4-ylamine | C | 431.2 | M (1.61) | — |
| 5-Fluoro-2-{1-[6-(4-trifluoromethoxy-phenoxy)-pyrimidin-4-yl-piperidin-4-yloxy}-pyrimidin-4-ylamine | C | 467.2 | B (1.98) | — |
| 5-Fluoro-2-[1-(6-o-tolyloxy-pyrimidin-4-yl)-piperidin-4-yloxy]-pyrimidin-4-ylamine | C | 397.2 | B (1.57) | — |
| 5-Fluoro-2-{1-[6-(2-fluoro-phenoxy)-pyrimidin-4-yl-piperidin-4-yloxy}-pyrimidin-4-ylamine | C | 401.1 | R (2.61) | — |
| 2-{6-[4-(4-Amino-5-fluoro-pyrimidin-2-yloxy)-piperidin-1-yl]-pyrimidin-4-yloxy}-benzonitrile | C | 408.0 | S (2.18) | — |
| 2-{1-[6-(2-Chloro-4-fluoro-phenoxy)-pyrimidin-4-yl-piperidin-4-yloxy}-5-fluoro-pyrimidin-4-ylamine | C | 435.0 | M (1.79) | — |
| 5-Fluoro-2-{1-[6-(2-methoxy-phenoxy)-pyrimidin-4-yl-piperidin-4-yloxy}-pyrimidin-4-ylamine | C | 413.2 | A (1.46) | 4 |
| 5-Fluoro-2-{1-[6-(2-isopropoxy-phenoxy)-pyrimidin-4-yl-piperidin-4-yloxy}-pyrimidin-4-ylamine | C | 441.2 | B (1.68) | — |
| 5-Fluoro-2-[1-(6-phenoxy-pyrimidin-4-yl)-piperidin-4-yloxy]-pyrimidin-4-ylamine | C | 383.2 | C (2.67) | — |
| 2-{1-[6-(2,4-Difluoro-phenoxy)-pyrimidin-4-yl]-piperidin-4-yloxy}-5-fluoro-pyrimidin-4-ylamine | C | 419.2 | M (1.62) | — |
| 5-Fluoro-2-{1-[6-(2,4,6-trifluoro-phenoxy)-pyrimidin-4-yl-piperidin-4-yloxy}-pyrimidin-4-ylamine | C | 436.8 | M (1.71) | — |
| 2-{1-[4-(2-Chloro-4-fluoro-phenoxy)-pyrimidin-2-yl]-piperidin-4-yloxy}-5-fluoro-pyrimidin-4-ylamine | C | 434.8 | M (1.88) | — |
| 2-{6-[4-(4-Amino-5-fluoro-pyrimidin-2-yloxy)-piperidin-1-yl]-2-methyl-pyrimidin-4-yloxy}-benzonitrile | C | 422.2 | M (1.60) | — |
| 2-{1-[6-(2-Chloro-4-methoxy-phenoxy)-pyrimidin-4-yl-piperidin-4-yloxy}-5-fluoro-pyrimidin-4-ylamine | C | 447.2 | M (1.67) | 5 |
| 2-{6-[4-(4-Amino-5-fluoro-pyrimidin-2-yloxy)-piperidin-1-yl]-5-methyl-pyrimidin-4-yloxy}-benzonitrile | C | 422.1 | B (1.66) | — |
| 5-Fluoro-2-[1-(9H-purin-6-yl)-piperidin-4-yloxy]-pyrimidin-4-ylamine | C | 331.1 | C (0.80) | — |
| 5-Fluoro-2-{1-[6-(4-methoxy-phenylamino)-pyrimidin-4-yl-piperidin-4-yloxy}-pyrimidin-4-ylamine | C | 412.0 | A (1.52) | 6 |
| 2-{1-[6-(Biphenyl-2-yloxy)-pyrimidin-4-yl]-piperidin-4-yloxy}-5-fluoro-pyrimidin-4-ylamine | C | 459.2 | Y (5.79) | — |
| 4-{6-[4-(4-Amino-5-fluoro-pyrimidin-2-yloxy)-piperidin-1-yl]-pyrimidin-4-yloxy}-3-methoxy-benzonitrile | C | 438.2 | C (1.50) | — |
| 2-{1-[6-(2,4-Difluoro-phenylamino)-pyrimidin-4-yl]-piperidin-4-yloxy}-5-fluoro-pyrimidin-4-ylamine | C | 418.0 | A (1.54) | — |

TABLE 2-continued

| Compound | Mthd | M + 1 | HPLC | NMR |
|---|---|---|---|---|
| 2-{6-[4-(4-Amino-5-fluoro-pyrimidin-2-yloxy)-piperidin-1-yl]-5-bromo-pyrimidin-4-yloxy}-benzonitrile | C | 488.0 | C (1.73) | — |
| 2-[1-(5-Bromo-6-methoxy-pyrimidin-4-yl)-piperidin-4-yloxy]-5-fluoro-pyrimidin-4-ylamine | C | 400.9 | C (1.56) | — |
| 2-{1-[2,6-Bis-(4-methoxy-phenoxy)-pyrimidin-4-yl]-piperidin-4-yloxy}-5-fluoro-pyrimidin-4-ylamine | C | 536.1 | A (2.03) | 7 |
| 5-Fluoro-2-(1-{6-[(4-methoxy-phenyl)-methyl-amino]-pyrimidin-4-yl}-piperidin-4-yloxy)-pyrimidin-4-ylamine | C | 425.9 | A (1.71) | 8 |
| 2-{1-[4-Chloro-6-(4-methoxy-phenoxy)-[1,3,5]triazin-2-yl]-piperidin-4-yloxy}-5-fluoro-pyrimidin-4-ylamine | C | 447.8 | A (1.95) | — |
| 5-Fluoro-2-{1-[6-(2-methoxy-phenylamino)-pyrimidin-4-yl]-piperidin-4-yloxy}-pyrimidin-4-ylamine | C | 412.0 | A (1.70) | — |
| 5-Fluoro-2-[4'-(4-methoxy-phenoxy)-3,4,5,6-tetrahydro-2H-[1,2']bipyridinyl-4-yloxy]-pyrimidin-4-ylamine | C | 412.0 | C (1.49) | — |
| 3-{6-[4-(4-Amino-5-fluoro-pyrimidin-2-yloxy)-piperidin-1-yl]-pyrimidin-4-yloxy}-benzonitrile | C | 408.0 | C (1.70) | 9 |
| 4-{6-[4-(4-Amino-5-fluoro-pyrimidin-2-yloxy)-piperidin-1-yl]-pyrimidin-4-yloxy}-benzonitrile | C | 408.0 | C (1.75) | — |
| 5-Fluoro-2-{1-[6-(pyridin-2-yloxy)-pyrimidin-4-yl]-piperidin-4-yloxy}-pyrimidin-4-ylamine | C | 384.0 | S (1.35) | — |
| 5-Fluoro-2-{1-[6-(pyridin-3-yloxy)-pyrimidin-4-yl]-piperidin-4-yloxy}-pyrimidin-4-ylamine | C | 384.0 | S (1.56) | — |
| 5-Fluoro-2-{1-[6-(1H-indol-6-yloxy)-pyrimidin-4-yl]-piperidin-4-yloxy}-pyrimidin-4-ylamine | C | 422.0 | S (1.91) | — |
| 2-{1-[6-(3-Bromo-phenoxy)-pyrimidin-4-yl]-piperidin-4-yloxy}-5-fluoro-pyrimidin-4-ylamine | C | 462.8 | S (2.47) | — |
| 5-Fluoro-2-{1-[6-(3-phenoxy-phenoxy)-pyrimidin-4-yl]-piperidin-4-yloxy}-pyrimidin-4-ylamine | C | 475.0 | S (2.59) | — |
| 4-{6-[4-(4-Amino-5-fluoro-pyrimidin-2-yloxy)-piperidin-1-yl]-pyrimidin-4-yloxy}-benzamide | C | 426.1 | U (1.75) | 10 |
| 4-{6-[4-(4-Amino-5-fluoro-pyrimidin-2-yloxy)-piperidin-1-yl]-pyrimidin-4-yloxy}-benzoic acid methyl ester | C | 441.0 | U (2.02) | — |
| 5-Fluoro-2-{1-[6-(quinolin-8-yloxy)-pyrimidin-4-yl]-piperidin-4-yloxy}-pyrimidin-4-ylamine | C | 434.0 | U (1.76) | — |
| 5-Fluoro-2-{1-[6-(1H-indol-4-yloxy)-pyrimidin-4-yl]-piperidin-4-yloxy}-pyrimidin-4-ylamine | C | 422.0 | U (1.84) | — |
| 2-{6-[4-(4-Amino-5-fluoro-pyrimidin-2-yloxy)-piperidin-1-yl]-pyrimidin-4-yloxy}-5-methoxy-benzonitrile | C | 438.2 | L (2.75) | — |
| 2-{1-[6-(4-Ethoxy-phenoxy)-pyrimidin-4-yl]-piperidin-4-yloxy}-5-fluoro-pyrimidin-4-ylamine | C | 427.1 | C (2.05) | 11 |
| 2-{6-[4-(4-Amino-5-fluoro-pyrimidin-2-yloxy)-piperidin-1-yl]-5-fluoro-pyrimidin-4-yloxy}-benzonitrile | C | 426.0 | C (2.07) | — |
| 2-{1-[4-Chloro-6-(2-methoxy-phenoxy)-pyrimidin-2-yl]-piperidin-4-yloxy}-5-fluoro-pyrimidin-4-ylamine | C | 446.9 | P (1.81) | — |
| 5-Fluoro-2-{1-[4-(4-methoxy-phenoxy)-[1,3,5]triazin-2-yl]-piperidin-4-yloxy}-pyrimidin-4-ylamine | C | 414.0 | A (1.67) | 12 |
| 4-(4-(4-amino-5-fluoropyrimidin-2-yloxy)piperidin-1-yl)-6-(2-methoxyphenoxy)pyrimidin-2-amine | C | 428.2 | V (1.56) | 13 |
| 4-(4-(4-amino-5-fluoropyrimidin-2-yloxy)piperidin-1-yl)-6-(2-methoxyphenoxy)-N,N-dimethylpyrimidin-2-amine | C | 456.2 | V (1.96) | 14 |
| 5-Fluoro-2-{1-[4-methoxy-6-(4-methoxy-phenoxy)-[1,3,5]triazin-2-yl]-piperidin-4-yloxy}-pyrimidin-4-ylamine | C | 444.0 | A (1.83) | — |
| 5-Fluoro-2-{1-[6-((R)-indan-1-yloxy)-pyrimidin-4-yl]-piperidin-4-yloxy}-pyrimidin-4-ylamine | C | 423.0 | L (3.22) | — |
| 2-{1-[6-(2,2-Dimethyl-2,3-dihydro-benzofuran-7-yloxy)-pyrimidin-4-yl]-piperidin-4-yloxy}-5-fluoro-pyrimidin-4-ylamine | C | 453.0 | L (2.95) | 15 |
| 2-{1-[6-(5-Chloro-pyridin-3-yloxy)-pyrimidin-4-yl]-piperidin-4-yloxy}-5-fluoro-pyrimidin-4-ylamine | C | 418.0 | S (2.14) | 16 |

TABLE 2-continued

| Compound | Mthd | M + 1 | HPLC | NMR |
|---|---|---|---|---|
| 2-{1-[6-(3-Amino-phenoxy)-pyrimidin-4-yl]-piperidin-4-yloxy}-5-fluoro-pyrimidin-4-ylamine | C | 398.0 | S (1.93) | — |
| 5-Fluoro-2-{1-[6-(2-piperidin-1-yl-phenoxy)-pyrimidin-4-yl]-piperidin-4-yloxy}-pyrimidin-4-ylamine | C | 466.0 | V (2.28) | — |
| 5-Fluoro-2-{1-[6-(2-morpholin-4-yl-phenoxy)-pyrimidin-4-yl]-piperidin-4-yloxy}-pyrimidin-4-ylamine | C | 468.0 | V (1.78) | 17 |
| 2-(1-Benzo[4,5]furo[3,2-d]pyrimidin-4-yl-piperidin-4-yloxy)-5-fluoro-pyrimidin-4-ylamine | C | 381.0 | B (1.46) | — |
| 5-Fluoro-2-{1-[6-(1H-indol-7-yloxy)-pyrimidin-4-yl]-piperidin-4-yloxy}-pyrimidin-4-ylamine | C | 422.0 | L (2.71) | — |
| 2-{1-[6-(1-Chloro-isoquinolin-4-yloxy)-pyrimidin-4-yl]-piperidin-4-yloxy}-5-fluoro-pyrimidin-4-ylamine | C | 468.0 | S (2.39) | — |
| 2-(1-{6-[1-(1-Chloro-isoquinolin-4-yloxy)-isoquinolin-4-yloxy]-pyrimidin-4-yl}-piperidin-4-yloxy)-5-fluoro-pyrimidin-4-ylamine | C | 611.0 | S (2.82) | — |
| 5-Fluoro-2-{1-[6-(1H-indol-5-yloxy)-pyrimidin-4-yl]-piperidin-4-yloxy}-pyrimidin-4-ylamine | C | 422.0 | L (2.48) | — |
| 5-Fluoro-2-{1-[6-(3-methoxy-naphthalen-2-yloxy)-pyrimidin-4-yl]-piperidin-4-yloxy}-pyrimidin-4-ylamine | C | 463.0 | L (3.10) | — |
| 5-Fluoro-2-{1-[6-(2-methyl-quinolin-8-yloxy)-pyrimidin-4-yl]-piperidin-4-yloxy}-pyrimidin-4-ylamine | C | 448.0 | L (2.53) | — |
| [4-[4-(4-Amino-5-fluoro-pyrimidin-2-yloxy)-piperidin-1-yl]-6-(4-methoxy-phenoxy)-[1,3,5]triazin-2-yl]-methyl-amine | C | 443.0 | Y (2.18) | — |
| 5-Fluoro-2-{1-[6-(3-fluoro-phenoxy)-pyrimidin-4-yl]-piperidin-4-yloxy}-pyrimidin-4-ylamine | C | 401.0 | S (2.25) | 18 |
| 5-Fluoro-2-{1-[6-(3-trifluoromethyl-phenoxy)-pyrimidin-4-yl]-piperidin-4-yloxy}-pyrimidin-4-ylamine | C | 451.0 | S (2.43) | — |
| 5-Fluoro-2-{1-[6-(2-fluoro-6-methoxy-phenoxy)-pyrimidin-4-yl]-piperidin-4-yloxy}-pyrimidin-4-ylamine | C | 431.1 | B (1.74) | — |
| 5-Fluoro-2-{1-[6-(2-methoxy-4-methyl-phenoxy)-pyrimidin-4-yl]-piperidin-4-yloxy}-pyrimidin-4-ylamine | C | 427.1 | B (1.78) | — |
| 2-{1-[6-(2,6-Dimethoxy-phenoxy)-pyrimidin-4-yl]-piperidin-4-yloxy}-5-fluoro-pyrimidin-4-ylamine | C | 443.1 | A (1.62) | — |
| 2-{1-[6-(2,3-Dimethoxy-phenoxy)-pyrimidin-4-yl]-piperidin-4-yloxy}-5-fluoro-pyrimidin-4-ylamine | C | 443.0 | A (1.67) | — |
| 6-{6-[4-(4-Amino-5-fluoro-pyrimidin-2-yloxy)-piperidin-1-yl]-pyrimidin-4-yloxy}-naphthalene-2-carbonitrile | C | 458.0 | L (3.02) | — |
| 5-Fluoro-2-{1-[6-(2-methyl-benzothiazol-5-yloxy)-pyrimidin-4-yl]-piperidin-4-yloxy}-pyrimidin-4-ylamine | C | 454.2 | L (2.61) | — |
| 5-Fluoro-2-{1-[6-(2-methyl-quinolin-6-yloxy)-pyrimidin-4-yl]-piperidin-4-yloxy}-pyrimidin-4-ylamine | C | 448.0 | L (2.53) | — |
| 2-{1-[4-Chloro-6-(2-methoxy-phenoxy)-[1,3,5]triazin-2-yl]-piperidin-4-yloxy}-5-fluoro-pyrimidin-4-ylamine | C | 448.2 | A (1.96) | 19 |
| 5-Fluoro-2-{1-[2-methoxy-6-(4-methoxy-phenoxy)-pyrimidin-4-yl]-piperidin-4-yloxy}-pyrimidin-4-ylamine | C | 443.2 | A (1.76) | — |
| 5-Fluoro-2-{1-[6-(2-pyrrol-1-yl-phenoxy)-pyrimidin-4-yl]-piperidin-4-yloxy}-pyrimidin-4-ylamine | C | 448.0 | V (2.34) | — |
| 5-Fluoro-2-{1-[6-(7-methoxy-naphthalen-2-yloxy)-pyrimidin-4-yl]-piperidin-4-yloxy}-pyrimidin-4-ylamine | C | 462.9 | L (3.12) | — |
| 8-{6-[4-(4-Amino-5-fluoro-pyrimidin-2-yloxy)-piperidin-1-yl]-pyrimidin-4-yloxy}-quinolin-2-ylamine | C | 449.0 | L (2.27) | — |
| 5-Fluoro-2-{1-[6-(6-methoxy-naphthalen-2-yloxy)-pyrimidin-4-yl]-piperidin-4-yloxy}-pyrimidin-4-ylamine | C | 462.9 | L (3.09) | — |
| 2-{1-[5-Bromo-6-(2-bromo-phenoxy)-pyrimidin-4-yl]-piperidin-4-yloxy}-5-fluoro-pyrimidin-4-ylamine | C | 541.0 | A (2.02) | 20 |

TABLE 2-continued

| Compound | Mthd | M + 1 | HPLC | NMR |
|---|---|---|---|---|
| 2-{1-[6-(Benzo[1,3]dioxol-5-yloxy)-pyrimidin-4-yl]-piperidin-4-yloxy}-5-fluoro-pyrimidin-4-ylamine | C | 427.0 | U (2.04) | — |
| 4-[4-(4-Amino-5-fluoro-pyrimidin-2-yloxy)-piperidin-1-yl]-6-(2-methoxy-phenoxy)-[1,3,5]triazin-2-ylamine | C | 429.0 | A (1.53) | — |
| 5-Fluoro-2-{1-[6-(1,2,3,4-tetrahydro-naphthalen-1-yloxy)-pyrimidin-4-yl]-piperidin-4-yloxy}-pyrimidin-4-ylamine | C | 437.0 | E (3.31) | — |
| 5-Fluoro-2-{1-[6-(quinolin-6-yloxy)-pyrimidin-4-yl]-piperidin-4-yloxy}-pyrimidin-4-ylamine | C | 433.9 | E (2.42) | — |
| 5-Fluoro-2-{1-[2-fluoro-6-(4-methoxy-phenoxy)-pyrimidin-4-yl]-piperidin-4-yloxy}-pyrimidin-4-ylamine | C | 431.1 | A (1.89) | — |
| 5-Fluoro-2-{1-[6-fluoro-2-(4-methoxy-phenoxy)-pyrimidin-4-yl]-piperidin-4-yloxy}-pyrimidin-4-ylamine | C | 431.1 | A (1.92) | 21 |
| 5-Fluoro-2-{1-[5-fluoro-6-(4-methoxy-phenoxy)-pyrimidin-4-yl]-piperidin-4-yloxy}-pyrimidin-4-ylamine | C | 431.1 | A (1.92) | — |
| 2-{1-[6-(3,4-Dimethoxy-phenoxy)-pyrimidin-4-yl]-piperidin-4-yloxy}-5-fluoro-pyrimidin-4-ylamine | C | 443.1 | A (1.57) | — |
| 2-{1-[3-(4-Chloro-pyrimidin-2-yloxy)-4-methoxy-phenyl]-piperidin-4-yloxy}-5-fluoro-pyrimidin-4-ylamine | C | 446.9 | U (2.34) | — |
| 2-{1-[2-Chloro-6-(2-methoxy-phenoxy)-pyrimidin-4-yl]-piperidin-4-yloxy}-5-fluoro-pyrimidin-4-ylamine | C | 446.9 | U (2.42) | — |
| 5-Fluoro-2-{1-[6-(2-methoxy-phenoxy)-2-phenyl-pyrimidin-4-yl]-piperidin-4-yloxy}-pyrimidin-4-ylamine | C | 489.0 | X (2.72) | — |
| 4-(4-(4-amino-5-fluoropyrimidin-2-yloxy)piperidin-1-yl)-6-(2-morpholinophenoxy)pyrimidin-2-amine | C | 483.0 | U (1.78) | — |
| 5-Fluoro-2-{1-[6-(4-methoxy-cyclohexyloxy)-pyrimidin-4-yl]-piperidin-4-yloxy}-pyrimidin-4-ylamine | C | 419.0 | J (4.19) | — |
| 5-Fluoro-2-{1-[6-(pyridin-4-yloxy)-pyrimidin-4-yl]-piperidin-4-yloxy}-pyrimidin-4-ylamine | C | 384.0 | S (1.60) | — |
| 5-Fluoro-2-{1-[6-((1R,2R)-1,7,7-trimethyl-bicyclo[2.2.1]hept-2-yloxy)-pyrimidin-4-yl]-piperidin-4-yloxy}-pyrimidin-4-ylamine | C | 443.0 | L (3.83) | — |
| 2-{1-[6-(2-tert-Butyl-phenoxy)-pyrimidin-4-yl]-piperidin-4-yloxy}-5-fluoro-pyrimidin-4-ylamine | C | 439.6 | A (2.00) | — |
| 5-Fluoro-2-{1-[6-(quinolin-7-yloxy)-pyrimidin-4-yl]-piperidin-4-yloxy}-pyrimidin-4-ylamine | C | 434.1 | N (1.74) | — |
| 1-{6-[4-(4-Amino-5-fluoro-pyrimidin-2-yloxy)-piperidin-1-yl]-pyrimidin-4-yl}-1H-quinolin-4-one | C | 434.0 | S (1.80) | — |
| 5-Fluoro-2-{1-[6-(quinolin-4-yloxy)-pyrimidin-4-yl]-piperidin-4-yloxy}-pyrimidin-4-ylamine | C | 434.0 | S (2.08) | — |
| 5-Fluoro-2-{1-[5-fluoro-6-(pyridin-3-yloxy)-pyrimidin-4-yl]-piperidin-4-yloxy}-pyrimidin-4-ylamine | C | 402.0 | S (2.01) | — |
| 2-{1-[6-(4-Bromo-phenoxy)-pyrimidin-4-yl]-piperidin-4-yloxy}-5-fluoro-pyrimidin-4-ylamine | C | 460.8 and 462.8 | S (2.43) | — |
| 3-{6-[4-(4-Amino-5-fluoro-pyrimidin-2-yloxy)-piperidin-1-yl]-pyrimidin-4-yloxy}-benzofuran-2-carbonitrile | C | 447.9 | L (3.20) | — |
| 5-Fluoro-2-{1-[6-(4-fluoro-phenoxy)-pyrimidin-4-yl]-piperidin-4-yloxy}-pyrimidin-4-ylamine | C | 401.0 | Y (2.18) | — |
| 2-{1-[6-(2-Chloro-5-methoxy-phenoxy)-pyrimidin-4-yl]-piperidin-4-yloxy}-5-fluoro-pyrimidin-4-ylamine | C | 447.5 | U (2.28) | 22 |
| 5-Fluoro-2-{1-[6-(3-morpholin-4-yl-phenoxy)-pyrimidin-4-yl]-piperidin-4-yloxy}-pyrimidin-4-ylamine | C | 468.6 | U (2.00) | — |
| 5-Fluoro-2-{1-[2-fluoro-6-(4-methoxy-phenoxy)-5-methyl-pyrimidin-4-yl]-piperidin-4-yloxy}-pyrimidin-4-ylamine | C | 445.1 | B (2.34) | — |
| 5-Fluoro-2-{1-[6-(2-fluoro-4-methoxy-phenoxy)-pyrimidin-4-yl]-piperidin-4-yloxy}-pyrimidin-4-ylamine | C | 431.5 | B (1.88) | — |

TABLE 2-continued

| Compound | Mthd | M + 1 | HPLC | NMR |
|---|---|---|---|---|
| 5-Fluoro-2-{1-[6-(6,7,8,9-tetrahydro-dibenzofuran-2-yloxy)-pyrimidin-4-yl]-piperidin-4-yloxy}-pyrimidin-4-ylamine | C | 447.0 | Q (5.59) | — |
| 5-Fluoro-2-{1-[6-(4-thiazol-2-yl-phenoxy)-pyrimidin-4-yl]-piperidin-4-yloxy}-pyrimidin-4-ylamine | C | 465.9 | Z (2.16) | — |
| 3-{6-[4-(4-Amino-5-fluoro-pyrimidin-2-yloxy)-piperidin-1-yl]-pyrimidin-4-yloxy}-4-methoxy-benzonitrile | C | 437.9 | Z (2.01) | 23 |
| 2-(1-{6-[4-(2-Amino-thiazol-4-yl)-phenoxy]-pyrimidin-4-yl}-piperidin-4-yloxy)-5-fluoro-pyrimidin-4-ylamine | C | 480.9 | AA (1.92) | — |
| 2-[1-(6-Benzyloxy-pyrimidin-4-yl)-piperidin-4-yloxy]-5-fluoro-pyrimidin-4-ylamine | C | 397.0 | L (2.90) | — |
| 3-{6-[4-(4-Amino-5-fluoro-pyrimidin-2-yloxy)-piperidin-1-yl]-pyrimidin-4-yloxy}-pyridine-2-carbonitrile | C | 408.9 | S (2.07) | — |
| 5-Fluoro-2-{1-[6-(3-piperidin-4-yl-phenoxy)-pyrimidin-4-yl]-piperidin-4-yloxy}-pyrimidin-4-ylamine | C | 466.0 | L (2.16) | — |
| 3-(1-{6-[4-(4-Amino-5-fluoro-pyrimidin-2-yloxy)-piperidin-1-yl]-pyrimidin-4-yl}-piperidin-4-yl)-phenol | C | 466.0 | L (2.59) | — |
| 3-(6-(4-(4-amino-5-fluoropyrimidin-2-yloxy)piperidin-1-yl)pyrimidin-4-yloxy)benzo[b]thiophene-2-carbonitrile | C | 463.9 | Q (4.97) | — |
| 2-(1-(6-amino-2-(4-methoxyphenoxy)pyrimidin-4-yl)piperidin-4-yloxy)-5-fluoropyrimidin-4-amine | C | 428.0 | A (1.61) | — |
| 5-Fluoro-2-[2'-(4-methoxy-phenoxy)-3,4,5,6-tetrahydro-2H-[1,4']bipyridinyl-4-yloxy]-pyrimidin-4-ylamine | C | 412.5 | A (1.44) | 24 |
| 5-Fluoro-2-{1-[6-((1S,2S)-2-morpholin-4-yl-cyclopentyloxy)-pyrimidin-4-yl]-piperidin-4-yloxy}-pyrimidin-4-ylamine | C | 460.0 | L (2.30) | — |
| 5-Fluoro-2-{1-[6-(2-fluoro-benzyloxy)-pyrimidin-4-yl]-piperidin-4-yloxy}-pyrimidin-4-ylamine | C | 414.9 | L (2.78) | — |
| 5-Fluoro-2-{1-[6-(2-methoxy-cyclohexyloxy)-pyrimidin-4-yl]-piperidin-4-yloxy}-pyrimidin-4-ylamine | C | 419.0 | L (2.73) | — |
| 2-{1-[6-(5-Chloro-pyridin-3-yloxy)-5-fluoro-pyrimidin-4-yl]-piperidin-4-yloxy}-5-fluoro-pyrimidin-4-ylamine | C | 435.9 | S (2.33) | — |
| 5-Fluoro-2-[1-(6-piperidin-1-yl-pyrimidin-4-yl)-piperidin-4-yloxy]-pyrimidin-4-ylamine | C | 374.0 | L (2.52) | — |
| 5-Fluoro-2-{1-[6-(2-trifluoromethyl-phenoxy)-pyrimidin-4-yl]-piperidin-4-yloxy}-pyrimidin-4-ylamine | C | 450.9 | S (2.38) | — |
| 2-[3'-(6-Chloro-pyrimidin-4-yloxy)-3,4,5,6-tetrahydro-2H-[1,2']bipyridinyl-4-yloxy]-5-fluoro-pyrimidin-4-ylamine | C | 417.9 | S (2.05) | — |
| 5-Fluoro-2-{1-[6-(2-iodo-pyridin-3-yloxy)-pyrimidin-4-yl]-piperidin-4-yloxy}-pyrimidin-4-ylamine | C | 509.8 | S (2.11) | — |
| 5-Fluoro-2-{1-[6-(quinolin-3-yloxy)-pyrimidin-4-yl]-piperidin-4-yloxy}-pyrimidin-4-ylamine | C | 433.9 | S (2.15) | — |
| 4-{6-[4-(4-Amino-5-fluoro-pyrimidin-2-yloxy)-piperidin-1-yl]-pyrimidin-4-yloxy}-2-fluoro-benzonitrile | C | 425.9 | R (2.61) | — |
| 2-{1-[6-(Benzothiazol-2-yloxy)-pyrimidin-4-yl]-piperidin-4-yloxy}-5-fluoro-pyrimidin-4-ylamine | C | 439.9 | L (2.67) | 25 |
| 3-{6-[4-(4-Amino-5-fluoro-pyrimidin-2-yloxy)-piperidin-1-yl]-5-fluoro-pyrimidin-4-yloxy}-benzonitrile | C | 425.9 | S (2.38) | — |
| 2-{6-[4-(4-Amino-5-fluoro-pyrimidin-2-yloxy)-piperidin-1-yl]-5-fluoro-pyrimidin-4-yloxy}-5-methoxy-benzonitrile | C | 456.1 | A (1.83) | — |
| 2-{1-[6-(2-Chloro-4-methoxy-phenoxy)-5-fluoro-pyrimidin-4-yl]-piperidin-4-yloxy}-5-fluoro-pyrimidin-4-ylamine | C | 464.9 | S (2.53) | — |
| 3-{6-[4-(4-Amino-5-fluoro-pyrimidin-2-yloxy)-piperidin-1-yl]-5-fluoro-pyrimidin-4-yloxy}-4-methoxy-benzonitrile | C | 455.9 | S (2.34) | 26 |
| 5-Fluoro-2-{1-[5-fluoro-6-(2-methoxy-phenoxy)-pyrimidin-4-yl]-piperidin-4-yloxy}-pyrimidin-4-ylamine | C | 431.0 | B (1.99) | — |

TABLE 2-continued

| Compound | Mthd | M + 1 | HPLC | NMR |
|---|---|---|---|---|
| 2-[1-(6-Dimethylamino-pyrimidin-4-yl)-piperidin-4-yloxy]-5-fluoro-pyrimidin-4-ylamine | C | 334.2 | L (2.00) | — |
| 2-((6-(4-(4-amino-5-fluoropyrimidin-2-yloxy)piperidin-1-yl)pyrimidin-4-yloxy)methyl)benzonitrile | C | 422.1 | L (2.80) | 27 |
| 2-{1-[6-(Biphenyl-2-ylmethoxy)-pyrimidin-4-yl]-piperidin-4-yloxy}-5-fluoro-pyrimidin-4-ylamine | C | 473.0 | L (3.52) | — |
| 5-Fluoro-2-{1-[6-(2-methyl-4-trifluoromethyl-2H-pyrazol-3-yloxy)-pyrimidin-4-yl]-piperidin-4-yloxy}-pyrimidin-4-ylamine | C | 454.9 | L (2.91) | — |
| 5-Fluoro-2-{1-[6-(4-phenyl-thiazol-2-yloxy)-pyrimidin-4-yl]-piperidin-4-yloxy}-pyrimidin-4-ylamine | C | 465.9 | L (3.42) | — |
| 5-Fluoro-2-(1-{6-[2-(1H-pyrazol-3-yl)-phenoxy]-pyrimidin-4-yl}-piperidin-4-yloxy)-pyrimidin-4-ylamine | C | 449.0 | V (2.55) | — |
| 2-(1-{6-[4-(4-Amino-5-fluoro-pyrimidin-2-yloxy)-piperidin-1-yl]-pyrimidin-4-yl}-1H-pyrazol-3-yl)-phenol | C | 449.0 | V (1.87) | — |
| 5-Fluoro-2-{1-[6-((1R,2S)-2-phenyl-cyclohexyloxy)-pyrimidin-4-yl]-piperidin-4-yloxy}-pyrimidin-4-ylamine | C | 465.0 | L (3.59) | — |
| 5-Fluoro-2-{1-[6-(2-[1,3,4]oxadiazol-2-yl-phenoxy)-pyrimidin-4-yl]-piperidin-4-yloxy}-pyrimidin-4-ylamine | C | 451.0 | V (1.85) | 28 |
| 5-Fluoro-2-{1-[5-fluoro-6-(4-fluoro-phenoxy)-pyrimidin-4-yl]-piperidin-4-yloxy}-pyrimidin-4-ylamine | C | 418.9 | U (2.39) | 29 |
| 5-Fluoro-2-{1-[6-(4-methoxy-phenoxy)-2,5-dimethyl-pyrimidin-4-yl]-piperidin-4-yloxy}-pyrimidin-4-ylamine | C | 441.0 | A (2.05) | 30 |
| 5-Fluoro-2-{1-[5-fluoro-6-(2-fluoro-phenoxy)-pyrimidin-4-yl]-piperidin-4-yloxy}-pyrimidin-4-ylamine | C | 419.0 | A (1.95) | — |
| 4-{6-[4-(4-Amino-5-fluoro-pyrimidin-2-yloxy)-piperidin-1-yl]-5-fluoro-pyrimidin-4-yloxy}-benzonitrile | C | 425.9 | A (1.84) | — |
| 2-{1-[6-(2,5-Dimethyl-2H-pyrazol-3-yloxy)-pyrimidin-4-yl]-piperidin-4-yloxy}-5-fluoro-pyrimidin-4-ylamine | C | 401.0 | L (2.22) | 31 |
| 5-Fluoro-2-{1-[6-(2-isoxazol-5-yl-phenoxy)-pyrimidin-4-yl]-piperidin-4-yloxy}-pyrimidin-4-ylamine | C | 449.9 | V (1.97) | — |
| 5-Fluoro-2-{1-[5-fluoro-6-(3-fluoro-phenoxy)-pyrimidin-4-yl]-piperidin-4-yloxy}-pyrimidin-4-ylamine | C | 419.0 | S (2.47) | — |
| 2-{1-[6-(3-Chloro-phenoxy)-5-fluoro-pyrimidin-4-yl]-piperidin-4-yloxy}-5-fluoro-pyrimidin-4-ylamine | C | 434.9 | S (2.61) | — |
| 5-Fluoro-2-{1-[5-fluoro-6-(3-methoxy-phenoxy)-pyrimidin-4-yl]-piperidin-4-yloxy}-pyrimidin-4-ylamine | C | 430.9 | S (2.41) | — |
| 2-{1-[6-(Benzothiazol-2-yloxy)-5-fluoro-pyrimidin-4-yl]-piperidin-4-yloxy}-5-fluoro-pyrimidin-4-ylamine | C | 457.9 | L (2.95) | — |
| 5-Fluoro-2-{1-[5-fluoro-6-((1S,2S)-2-morpholin-4-yl-cyclopentyloxy)-pyrimidin-4-yl]-piperidin-4-yloxy}-pyrimidin-4-ylamine | C | 477.9 | L (2.60) | — |
| 5-Fluoro-2-{1-[5-fluoro-6-(2-methyl-benzothiazol-5-yloxy)-pyrimidin-4-yl]-piperidin-4-yloxy}-pyrimidin-4-ylamine | C | 471.9 | L (2.96) | — |
| 5-Fluoro-2-{1-[6-((1R,2S)-2-phenyl-cyclopentyloxy)-pyrimidin-4-yl]-piperidin-4-yloxy}-pyrimidin-4-ylamine | C | 451.0 | L (3.41) | 32 |
| 2-{1-[6-(3,4-Difluoro-phenoxy)-pyrimidin-4-yl]-piperidin-4-yloxy}-5-fluoro-pyrimidin-4-ylamine | C | 418.9 | A (1.85) | — |
| 2-{1-[6-(3-Chloro-4-fluoro-phenoxy)-pyrimidin-4-yl]-piperidin-4-yloxy}-5-fluoro-pyrimidin-4-ylamine | C | 434.9 | R (2.93) | 33 |
| 2-{1-[6-(4-Ethoxy-phenoxy)-5-fluoro-pyrimidin-4-yl]-piperidin-4-yloxy}-5-fluoro-pyrimidin-4-ylamine | C | 444.9 | S (2.50) | — |
| 5-Fluoro-2-{1-[5-fluoro-6-(2-methoxy-4-methyl-phenoxy)-pyrimidin-4-yl]-piperidin-4-yloxy}-pyrimidin-4-ylamine | C | 444.9 | S (2.47) | — |

TABLE 2-continued

| Compound | Mthd | M + 1 | HPLC | NMR |
|---|---|---|---|---|
| 5-Fluoro-2-(1-{5-fluoro-6-[1-(4-methoxy-phenyl)-1H-tetrazol-5-yloxy]-pyrimidin-4-yl}-piperidin-4-yloxy)-pyrimidin-4-ylamine | C | 499.0 | U (2.27) | — |
| 2-{1-[6-(2-Cyclohexyl-phenoxy)-pyrimidin-4-yl]-piperidin-4-yloxy}-5-fluoro-pyrimidin-4-ylamine | C | 465.1 | V (2.81) | — |
| 2-{1-[6-(2,3-Dihydro-indol-1-yl)-pyrimidin-4-yl]-piperidin-4-yloxy}-5-fluoro-pyrimidin-4-ylamine | C | 408.0 | V (2.37) | 34 |
| 5-Fluoro-2-{1-[6-(5-methoxy-1H-benzoimidazol-2-yloxy)-pyrimidin-4-yl]-piperidin-4-yloxy}-pyrimidin-4-ylamine | C | 453.0 | L (2.49) | — |
| 3-{6-[4-(4-Amino-5-fluoro-pyrimidin-2-yloxy)-piperidin-1-yl]-5-fluoro-pyrimidin-4-yloxy}-isoxazole-5-carboxylic acid | C | 435.9 | L (1.66) | — |
| 5-Fluoro-2-{1-[5-fluoro-6-(1H-indol-2-yloxy)-pyrimidin-4-yl]-piperidin-4-yloxy}-pyrimidin-4-ylamine | C | 439.9 | L (2.91) | — |
| 5-Fluoro-2-{1-[6-(isoquinolin-6-yloxy)-pyrimidin-4-yl]-piperidin-4-yloxy}-pyrimidin-4-ylamine | C | 433.9 | L (2.47) | — |
| 1-(3-{6-[4-(4-Amino-5-fluoro-pyrimidin-2-yloxy)-piperidin-1-yl]-5-fluoro-pyrimidin-4-yloxy}-indol-1-yl)-ethanone | C | 481.9 | L (3.13) | — |
| 5-fluoro-2-(1-(5-fluoro-6-(6-(trifluoromethyl)pyridin-3-yloxy)pyrimidin-4-yl)piperidin-4-yloxy)pyrimidin-4-amine | C | 469.9 | S (2.46) | — |
| 2-{6-[4-(4-Amino-5-fluoro-pyrimidin-2-yloxy)-piperidin-1-yl]-5-fluoro-pyrimidin-4-yloxy}-6-fluoro-benzonitrile | C | 443.9 | S (2.41) | — |
| 2-{1-[6-(2-Cyclopentyl-phenoxy)-pyrimidin-4-yl]-piperidin-4-yloxy}-5-fluoro-pyrimidin-4-ylamine | C | 451.0 | V (2.62) | — |
| 4-{6-[4-(4-Amino-5-fluoro-pyrimidin-2-yloxy)-piperidin-1-yl]-5-fluoro-pyrimidin-4-yloxy}-benzamide | C | 444.0 | V (1.76) | — |
| 2-{1-[6-(2-Chloro-phenoxy)-5-fluoro-pyrimidin-4-yl]-piperidin-4-yloxy}-5-fluoro-pyrimidin-4-ylamine | C | 434.9 | V (2.48) | — |
| 2-{1-[6-(2-Ethoxy-phenoxy)-5-fluoro-pyrimidin-4-yl]-piperidin-4-yloxy}-5-fluoro-pyrimidin-4-ylamine | C | 444.9 | V (2.41) | — |
| 4-{6-[4-(4-Amino-5-fluoro-pyrimidin-2-yloxy)-piperidin-1-yl]-5-fluoro-pyrimidin-4-yloxy}-benzenesulfonamide | C | 480.5 | A (1.41) | — |
| 5-Fluoro-2-{1-[5-fluoro-6-(4-methoxy-phenoxy)-2-trifluoromethyl-pyrimidin-4-yl]-piperidin-4-yloxy}-pyrimidin-4-ylamine | C | 499.1 | A (1.95) | — |
| 2-[4-(4-Amino-5-fluoro-pyrimidin-2-yloxy)-piperidin-1-yl]-6-(4-methoxy-phenoxy)-benzonitrile | C | 436.0 | S (2.59) | 35 |
| 2-[4-(4-Amino-5-fluoro-pyrimidin-2-yloxy)-piperidin-1-yl]-6-(2-methoxy-phenoxy)-benzonitrile | C | 436.0 | S (2.56) | — |
| 5-Fluoro-2-(1-{6-[2-(2-methoxy-phenyl)-ethoxy]-pyrimidin-4-yl}-piperidin-4-yloxy)-pyrimidin-4-ylamine | C | 441.0 | L (3.07) | — |
| 2-{1-[6-(2-Bromo-4-methoxy-phenoxy)-5-fluoro-pyrimidin-4-yl]-piperidin-4-yloxy}-5-fluoro-pyrimidin-4-ylamine | C | 508.8 and 510.8 | S (2.55) | — |
| 5-Fluoro-2-{1-[6-(1-methyl-5-trifluoromethyl-1H-pyrazol-3-yloxy)-pyrimidin-4-yl]-piperidin-4-yloxy}-pyrimidin-4-ylamine | C | 455.0 | L (2.78) | — |
| 2-{6-[4-(4-Amino-5-fluoro-pyrimidin-2-yloxy)-piperidin-1-yl]-pyrimidin-4-yloxy}-benzamide | C | 426.1 | V (1.90) | — |
| 5-Fluoro-2-{1-[5-fluoro-6-(2-fluoro-4-methoxy-phenoxy)-pyrimidin-4-yl]-piperidin-4-yloxy}-pyrimidin-4-ylamine | C | 449.5 | A (1.86) | — |
| 1-{6-[4-(4-Amino-5-fluoro-pyrimidin-2-yloxy)-piperidin-1-yl]-5-fluoro-pyrimidin-4-yl}-piperidine-4-carboxylic acid amide | C | 435.5 | A (1.17) | — |
| 6-[4-(4-Amino-5-fluoro-pyrimidin-2-yloxy)-piperidin-1-yl]-5-chloro-4-(4-methoxy-phenoxy)-1H-pyrimidin-2-one | C | 463.5 | A (2.00) | — |
| 5-Fluoro-2-{1-[5-fluoro-6-(4-methoxy-piperidin-1-yl)-pyrimidin-4-yl]-piperidin-4-yloxy}-pyrimidin-4-ylamine | C | 422.5 | A (1.58) | — |

TABLE 2-continued

| Compound | Mthd | M + 1 | HPLC | NMR |
|---|---|---|---|---|
| 1-{6-[4-(4-Amino-5-fluoro-pyrimidin-2-yloxy)-piperidin-1-yl]-5-fluoro-pyrimidin-4-yl}-piperidine-4-carbonitrile | C | 417.5 | A (1.53) | — |
| 2-(1-(6-(4-methoxyphenoxy)pyrimidin-4-yl)piperidin-4-yloxy)pyrimidin-4-amine | C | 395.0 | A (1.11) | 36 |
| 3-{6-[4-(4-Amino-pyrimidin-2-yloxy)-piperidin-1-yl]-pyrimidin-4-yloxy}-4-methoxy-benzonitrile | C | 420.1 | A (1.09) | 37 |
| 5-Fluoro-2-{1-[3-(4-methoxy-phenoxy)-2-nitro-phenyl]-piperidin-4-yloxy}-pyrimidin-4-ylamine | C | 455.9 | S (2.68) | 38 |
| 5-Fluoro-2-{1-[5-fluoro-6-(6-trifluoromethyl-pyrimidin-4-yloxy)-pyrimidin-4-yl]-piperidin-4-yloxy}-pyrimidin-4-ylamine | C | 470.9 | L (2.65) | — |
| 5-Fluoro-2-{1-[5-fluoro-6-(4-fluoro-piperidin-1-yl)-pyrimidin-4-yl]-piperidin-4-yloxy}-pyrimidin-4-ylamine | C | 410.5 | A (1.68) | — |
| 2-{1-[6-(4,4-Difluoro-piperidin-1-yl)-5-fluoro-pyrimidin-4-yl]-piperidin-4-yloxy}-5-fluoro-pyrimidin-4-ylamine | C | 428.5 | A (1.79) | — |
| 5-{6-[4-(4-Amino-5-fluoro-pyrimidin-2-yloxy)-piperidin-1-yl]-5-fluoro-pyrimidin-4-yloxy}-3,4-dihydro-1H-quinolin-2-one | C | 469.9 | L (2.50) | — |
| 6-{6-[4-(4-Amino-5-fluoro-pyrimidin-2-yloxy)-piperidin-1-yl]-5-fluoro-pyrimidin-4-yloxy}-3,4-dihydro-1H-quinolin-2-one | C | 470.0 | L (2.43) | — |
| 5-Fluoro-2-{1-[6-(4-imidazol-1-yl-phenoxy)-pyrimidin-4-yl]-piperidin-4-yloxy}-pyrimidin-4-ylamine | C | 449.0 | V (1.83) | — |
| 5-Fluoro-2-{1-[6-(4-[1,2,4]triazol-1-yl-phenoxy)-pyrimidin-4-yl]-piperidin-4-yloxy}-pyrimidin-4-ylamine | C | 450.0 | V (1.79) | 39 |
| 5-Fluoro-2-{1-[5-fluoro-6-(2-fluoro-6-methoxy-phenoxy)-pyrimidin-4-yl]-piperidin-4-yloxy}-pyrimidin-4-ylamine | C | 448.9 | S (2.42) | — |
| 2-{1-[6-(2-Chloro-5-methoxy-phenoxy)-5-fluoro-pyrimidin-4-yl]-piperidin-4-yloxy}-5-fluoro-pyrimidin-4-ylamine | C | 465.1 | Y (2.61) | 40 |
| 5-Fluoro-2-{1-[6-(2,2,2-trifluoro-ethoxy)-pyrimidin-4-yl]-piperidin-4-yloxy}-pyrimidin-4-ylamine | C | 389.1 | W (2.02) | 41 |
| 2-[1-(6-Ethoxy-pyrimidin-4-yl)-piperidin-4-yloxy]-5-fluoro-pyrimidin-4-ylamine | C | 335.1 | W (1.49) | — |
| 3-{6-[4-(4-Amino-5-fluoro-pyrimidin-2-yloxy)-piperidin-1-yl]-5-fluoro-pyrimidin-4-yloxy}-2-methoxy-benzonitrile | C | 456.1 | W (2.14) | — |
| 2-[4-(4-Amino-5-fluoro-pyrimidin-2-yloxy)-3,4,5,6-tetrahydro-2H-[1,2']bipyridinyl-3'-yloxy]-benzonitrile | C | 407.0 | S (2.31) | 42 |
| 2-{1-[6-(2,6-Dimethoxy-phenoxy)-5-fluoro-pyrimidin-4-yl]-piperidin-4-yloxy}-5-fluoro-pyrimidin-4-ylamine | C | 461.0 | S (2.34) | — |
| 5-Fluoro-2-{1-[5-fluoro-6-(2-methoxy-6-methyl-phenoxy)-pyrimidin-4-yl]-piperidin-4-yloxy}-pyrimidin-4-ylamine | C | 445.0 | S (2.45) | — |
| 5-Fluoro-2-{1-[5-fluoro-6-(2-methoxy-5-methyl-phenoxy)-pyrimidin-4-yl]-piperidin-4-yloxy}-pyrimidin-4-ylamine | C | 445.0 | S (2.48) | — |
| 2-(2-{6-[4-(4-Amino-5-fluoro-pyrimidin-2-yloxy)-piperidin-1-yl]-pyrimidin-4-yloxy}-phenoxy)-ethanol | C | 443.0 | V (1.81) | 43 |
| 3-{6-[4-(4-Amino-5-fluoro-pyrimidin-2-yloxy)-piperidin-1-yl]-5-fluoro-pyrimidin-4-yloxy}-5-hydroxy-benzonitrile | C | 441.9 | S (2.23) | — |
| 2-{1-[6-(2,4-Difluoro-phenoxy)-5-fluoro-pyrimidin-4-yl]-piperidin-4-yloxy}-5-fluoro-pyrimidin-4-ylamine | C | 437.0 | S (2.55) | — |
| 3,5-Bis-{6-[4-(4-amino-5-fluoro-pyrimidin-2-yloxy)-piperidin-1-yl]-5-fluoro-pyrimidin-4-yloxy}-benzonitrile | C | 747.9 | S (2.28) | — |
| 2-[2'-(4-Ethoxy-phenoxy)-3,4,5,6-tetrahydro-2H-[1,4']bipyridinyl-4-yloxy]-5-fluoro-pyrimidin-4-ylamine | C | 426.5 | B (1.74) | — |
| 6-[4-(4-Amino-5-fluoro-pyrimidin-2-yloxy)-piperidin-1-yl]-pyrimidine-4,5-dicarbonitrile | C | 341.0 | L (2.50) | — |
| 5-Fluoro-2-{1-[5-fluoro-6-(pyren-1-yloxy)-pyrimidin-4-yl]-piperidin-4-yloxy}-pyrimidin-4-ylamine | C | 525.2 | A (2.14) | 44 |

TABLE 2-continued

| Compound | Mthd | M + 1 | HPLC | NMR |
|---|---|---|---|---|
| 2-{1-[6-(3,5-Dimethyl-phenoxy)-5-fluoro-pyrimidin-4-yl]-piperidin-4-yloxy}-5-fluoro-pyrimidin-4-ylamine | C | 429.0 | S (2.61) | — |
| 2-{1-[6-(3,5-Dimethoxy-phenoxy)-5-fluoro-pyrimidin-4-yl]-piperidin-4-yloxy}-5-fluoro-pyrimidin-4-ylamine | C | 461.0 | S (2.19) | — |
| 2-{1-[6-(3,5-Difluoro-phenoxy)-5-fluoro-pyrimidin-4-yl]-piperidin-4-yloxy}-5-fluoro-pyrimidin-4-ylamine | C | 437.0 | S (2.27) | — |
| 5-Fluoro-2-[1-(5-fluoro-6-isopropoxy-pyrimidin-4-yl)-piperidin-4-yloxy]-pyrimidin-4-ylamine | C | 367.2 | A (2.18) | — |
| 3-{6-[4-(4-Amino-pyrimidin-2-yloxy)-piperidin-1-yl]-5-fluoro-pyrimidin-4-yloxy}-4-methoxy-benzonitrile | C | 438.0 | S (2.20) | 45 |
| 2-{6-[4-(4-Amino-pyrimidin-2-yloxy)-piperidin-1-yl]-5-fluoro-pyrimidin-4-yloxy}-benzonitrile | C | 408.2 | L (2.66) | 46 |
| 2-{1-[6-(2-Chloro-4-methoxy-phenoxy)-5-nitro-pyrimidin-4-yl]-piperidin-4-yloxy}-5-fluoro-pyrimidin-4-ylamine | C | 491.9 | S (2.59) | — |
| 2-{1-[5-Fluoro-6-(2-fluoro-phenoxy)-pyrimidin-4-yl]-piperidin-4-yloxy}-pyrimidin-4-ylamine | C | 401.0 | L (2.85) | — |
| 2-{6-[4-(4-Amino-5-fluoro-pyrimidin-2-yloxy)-piperidin-1-yl]-5-nitro-pyrimidin-4-yloxy}-benzonitrile | C | 453.0 | S (2.41) | — |
| 3-{6-[4-(4-Amino-5-fluoro-pyrimidin-2-yloxy)-piperidin-1-yl]-5-nitro-pyrimidin-4-yloxy}-benzonitrile | C | 453.0 | S (2.45) | — |
| 2-{6-[4-(4-Amino-5-fluoro-pyrimidin-2-yloxy)-piperidin-1-yl]-5-nitro-pyrimidin-4-yloxy}-5-methoxy-benzonitrile | C | 483.0 | S (2.49) | — |
| 5-Fluoro-2-{1-[6-(3-methoxy-phenoxy)-5-nitro-pyrimidin-4-yl]-piperidin-4-yloxy}-pyrimidin-4-ylamine | C | 458.0 | S (2.49) | — |
| 4-{6-[4-(4-Amino-5-fluoro-pyrimidin-2-yloxy)-piperidin-1-yl]-5-nitro-pyrimidin-4-yloxy}-3-methoxy-benzonitrile | C | 483.0 | S (2.47) | — |
| 5-Fluoro-2-{1-[6-(2-methoxy-phenoxy)-5-nitro-pyrimidin-4-yl]-piperidin-4-yloxy}-pyrimidin-4-ylamine | C | 458.0 | S (2.45) | — |
| 2-(1-{6-[4-(2-Amino-ethyl)-2-methoxy-phenoxy]-5-fluoro-pyrimidin-4-yl}-piperidin-4-yloxy)-5-fluoro-pyrimidin-4-ylamine | C | 474.3 | R (1.85) | 47 |
| 2-(1-{6-[4-(2-Benzylamino-ethyl)-2-methoxy-phenoxy]-5-fluoro-pyrimidin-4-yl}-piperidin-4-yloxy)-5-fluoro-pyrimidin-4-ylamine | C | 564.3 | R (2.47) | — |
| 2-(1-{6-[4-(2-Dibenzylamino-ethyl)-2-methoxy-phenoxy]-5-fluoro-pyrimidin-4-yl}-piperidin-4-yloxy)-5-fluoro-pyrimidin-4-ylamine | C | 654.3 | R (4.29) | — |
| 2-(1-{6-[4-(2-Dimethylamino-ethyl)-2-methoxy-phenoxy]-5-fluoro-pyrimidin-4-yl}-piperidin-4-yloxy)-5-fluoro-pyrimidin-4-ylamine | C | 502.3 | R (1.72) | — |
| 2-(1-{6-[4-(2-Diethylamino-ethyl)-2-methoxy-phenoxy]-5-fluoro-pyrimidin-4-yl}-piperidin-4-yloxy)-5-fluoro-pyrimidin-4-ylamine | C | 530.1 | A (1.48) | 48 |
| 2-(1-{6-[4-(2-Diethylamino-ethyl)-2-methoxy-phenoxy]-5-fluoro-pyrimidin-4-yl}-piperidin-4-yloxy)-pyrimidin-4-ylamine | C | 512.2 | R (1.70) | 49 |
| 2-{1-[6-(4-Dimethylaminomethyl-phenoxy)-5-fluoro-pyrimidin-4-yl]-piperidin-4-yloxy}-5-fluoro-pyrimidin-4-ylamine | C | 458.4 | H (1.48) | — |
| 2-{1-[6-(2-Dimethylaminomethyl-phenoxy)-5-fluoro-pyrimidin-4-yl]-piperidin-4-yloxy}-5-fluoro-pyrimidin-4-ylamine | C | 458.4 | G (1.77) | — |
| 2-{1-[6-(4-Bromo-3-dimethylaminomethyl-phenoxy)-5-fluoro-pyrimidin-4-yl]-piperidin-4-yloxy}-5-fluoro-pyrimidin-4-ylamine | C | 538.2 | G (1.99) | — |
| 5-Fluoro-2-(1-{5-fluoro-6-[2-methoxy-4-(1H-tetrazol-5-yl)-phenoxy]-pyrimidin-4-yl}-piperidin-4-yloxy)-pyrimidin-4-ylamine | C | 499.3 | G (2.56) | — |
| 2-{1-[6-(4-Butoxy-phenoxy)-5-fluoro-pyrimidin-4-yl]-piperidin-4-yloxy}-5-fluoro-pyrimidin-4-ylamine | C | 473.1 | V (2.86) | 50 |
| 5-Fluoro-2-{1-[5-fluoro-6-(4-hexyloxy-phenoxy)-pyrimidin-4-yl]-piperidin-4-yloxy}-pyrimidin-4-ylamine | C | 501.1 | V (3.13) | — |
| 3-{6-[3-(4-Amino-5-fluoro-pyrimidin-2-yloxy)-8-aza-bicyclo[3.2.1]oct-8-yl]-pyrimidin-4-yloxy}-4-methoxy-benzonitrile | C | 464.1 | V (2.20) | — |

TABLE 2-continued

| Compound | Mthd | M + 1 | HPLC | NMR |
|---|---|---|---|---|
| 2-(1-{6-[4-(2-Diethylamino-ethyl)-phenoxy]-5-fluoro-pyrimidin-4-yl}-piperidin-4-yloxy)-5-fluoro-pyrimidin-4-ylamine | C | 500.4 | A (0.92) | 51 |
| 5-Fluoro-2-{1-[5-fluoro-6-(4-methyl-piperazin-1-yl)-pyrimidin-4-yl]-piperidin-4-yloxy}-pyrimidin-4-ylamine | C | 407.4 | I (1.44) | — |
| N-{6-[4-(4-Amino-5-fluoro-pyrimidin-2-yloxy)-piperidin-1-yl]-5-fluoro-pyrimidin-4-yl}-N,N',N'-trimethyl-ethane-1,2-diamine | C | 409.4 | I (1.40) | — |
| N-{6-[4-(4-Amino-5-fluoro-pyrimidin-2-yloxy)-piperidin-1-yl]-5-fluoro-pyrimidin-4-yl}-N,N',N'-trimethyl-propane-1,3-diamine | C | 423.4 | I (1.30) | — |
| 2-(4-{6-[4-(4-Amino-5-fluoro-pyrimidin-2-yloxy)-piperidin-1-yl]-5-fluoro-pyrimidin-4-yloxy}-phenoxy)-N,N-dimethyl-acetamide | C | 502.1 | L (2.51) | — |
| 5-Fluoro-2-{1-[5-fluoro-6-(1-methyl-piperidin-4-yloxy)-pyrimidin-4-yl]-piperidin-4-yloxy}-pyrimidin-4-ylamine | C | 422.4 | G (1.51) | 52 |
| 3-{2-[4-(4-Amino-5-fluoro-pyrimidin-2-yloxy)-piperidin-1-yl]-pyrimidin-4-yloxy}-4-methoxy-benzonitrile | C | 438.3 | L (2.81) | 53 |
| 3-{4-[4-(4-Amino-5-fluoro-pyrimidin-2-yloxy)-piperidin-1-yl]-pyrimidin-2-yloxy}-4-methoxy-benzonitrile | C | 438.3 | L (2.44) | — |
| 2-{6-[3-(4-Amino-5-fluoro-pyrimidin-2-yloxy)-8-aza-bicyclo[3.2.1]oct-8-yl]-5-fluoro-pyrimidin-4-yloxy}-benzonitrile | C | 452.0 | V (2.37) | — |
| 4-{6-[4-(4-Amino-5-fluoro-pyrimidin-2-yloxy)-piperidin-1-yl]-5-nitro-pyrimidin-4-yloxy}-benzonitrile | C | 453.0 | S (2.44) | — |
| 4-[4-(4-Amino-5-fluoro-pyrimidin-2-yloxy)-piperidin-1-yl]-6-(4-methoxy-phenoxy)-pyrimidine-5-carbonitrile | CC | 437.9 | X (2.25) | — |
| 2-(1-(2,3-dichlorophenylsulfonyl)piperidin-4-yloxy)-5-fluoropyrimidin-4-amine | D | 420.9 | A (1.94) | — |
| 5-fluoro-2-(1-(naphthalen-1-ylsulfonyl)piperidin-4-yloxy)pyrimidin-4-amine | D | 403.0 | A (1.93) | — |
| 5-fluoro-2-(1-(naphthalen-2-ylsulfonyl)piperidin-4-yloxy)pyrimidin-4-amine | D | 403.3 | A (1.95) | — |
| 5-fluoro-2-(1-(5-methylbenzo[c][1,2,5]thiadiazol-4-ylsulfonyl)piperidin-4-yloxy)pyrimidin-4-amine | D | 424.9 | A (1.74) | — |
| 5-fluoro-2-(1-(5,5,8,8-tetramethyl-5,6,7,8-tetrahydronaphthalen-2-ylsulfonyl)piperidin-4-yloxy)pyrimidin-4-amine | D | 463.0 | A (1.84) | — |
| 5-fluoro-2-(1-(2-fluorophenylsulfonyl)piperidin-4-yloxy)pyrimidin-4-amine | D | 371.0 | A (1.47) | — |
| 2-(1-(7-chlorobenzo[c][1,2,5]oxadiazol-4-ylsulfonyl)piperidin-4-yloxy)-5-fluoropyrimidin-4-amine | D | 428.9 | A (1.41) | — |
| 5-fluoro-2-(1-(isoquinolin-5-ylsulfonyl)piperidin-4-yloxy)pyrimidin-4-amine | D | 404.0 | A (1.58) | — |
| 5-fluoro-2-(1-(4-methylnaphthalen-1-ylsulfonyl)piperidin-4-yloxy)pyrimidin-4-amine | D | 417.0 | A (2.02) | — |
| 5-fluoro-2-(1-(4-fluoronaphthalen-1-ylsulfonyl)piperidin-4-yloxy)pyrimidin-4-amine | D | 421.0 | A (2.02) | — |
| 2-(1-(2,3-dihydrobenzo[b][1,4]dioxin-6-ylsulfonyl)piperidin-4-yloxy)-5-fluoropyrimidin-4-amine | D | 411.0 | A (1.74) | — |
| 2-(1-(5-(dimethylamino)naphthalen-1-ylsulfonyl)piperidin-4-yloxy)-5-fluoropyrimidin-4-amine | D | 446.0 | A (2.03) | — |
| 5-fluoro-2-(1-(2-methoxy-4-methylphenylsulfonyl)piperidin-4-yloxy)pyrimidin-4-amine | D | 397.0 | A (1.70) | — |
| 2-(1-(5-chloro-2-methoxyphenylsulfonyl)piperidin-4-yloxy)-5-fluoropyrimidin-4-amine | D | 416.9 | A (1.79) | — |
| 2-(1-(2,5-dimethoxyphenylsulfonyl)piperidin-4-yloxy)-5-fluoropyrimidin-4-amine | D | 413.0 | A (1.63) | — |
| 5-fluoro-2-(1-(2-(4-methoxyphenoxy)phenylsulfonyl)piperidin-4-yloxy)pyrimidin-4-amine | E | 474.9 | A (1.99) | — |
| [4-(4-Amino-5-fluoro-pyrimidin-2-yloxy)-piperidin-1-yl]-[2-(4-methoxy-phenoxy)-phenyl]-methanone | E | 439.2 | A (1.73) | 54 |

TABLE 2-continued

| Compound | Mthd | M + 1 | HPLC | NMR |
|---|---|---|---|---|
| [4-(4-Amino-5-fluoro-pyrimidin-2-yloxy)-piperidin-1-yl]-[2-(4-fluoro-phenoxy)-phenyl]-methanone | E | 427.2 | A (1.76) | — |
| 6-[4-(4-Amino-5-fluoro-pyrimidin-2-yloxy)-piperidin-1-yl]-pyrimidine-4-carboxylic acid isopropyl ester | G | 377.0 | L (2.20) | — |
| 6-[4-(4-Amino-5-fluoro-pyrimidin-2-yloxy)-piperidin-1-yl]-pyrimidine-4-carboxylic acid amide | G | 334.0 | L (1.68) | — |
| 6-[4-(4-Amino-5-fluoro-pyrimidin-2-yloxy)-piperidin-1-yl]-pyrimidine-4-carboxylic acid (2-methoxy-phenyl)-amide | G | 440.0 | L (3.13) | — |
| {6-[4-(4-Amino-5-fluoro-pyrimidin-2-yloxy)-piperidin-1-yl]-pyrimidin-4-yl}-(2,3-dihydro-indol-1-yl)-methanone | G | 436.0 | L (2.55) | 55 |
| 6-[4-(4-Amino-5-fluoro-pyrimidin-2-yloxy)-piperidin-1-yl]-pyrimidine-4-carboxylic acid methyl-phenyl-amide | G | 424.0 | L (2.16) | — |
| {6-[4-(4-Amino-5-fluoro-pyrimidin-2-yloxy)-piperidin-1-yl]-pyrimidin-4-yl}-(3,4-dihydro-2H-quinolin-1-yl)-methanone | G | 450.0 | L (2.44) | — |
| {6-[4-(4-Amino-5-fluoro-pyrimidin-2-yloxy)-piperidin-1-yl]-pyrimidin-4-yl}-(5-chloro-2,3-dihydro-indol-1-yl)-methanone | G | 469.9 | L (2.89) | — |
| {6-[4-(4-Amino-5-fluoro-pyrimidin-2-yloxy)-piperidin-1-yl]-pyrimidin-4-yl}-(2-methyl-2,3-dihydro-indol-1-yl)-methanone | G | 450.0 | L (2.67) | — |
| {6-[4-(4-Amino-5-fluoro-pyrimidin-2-yloxy)-piperidin-1-yl]-pyrimidin-4-yl}-(5-methoxy-2,3-dihydro-indol-1-yl)-methanone | G | 466.0 | L (3.82) | — |
| 6-[4-(4-Amino-5-fluoro-pyrimidin-2-yloxy)-piperidin-1-yl]-pyrimidine-4-carboxylic acid (4-methoxy-phenyl)-methyl-amide | G | 454.0 | L (2.27) | — |
| {6-[4-(4-Amino-5-fluoro-pyrimidin-2-yloxy)-piperidin-1-yl]-pyrimidin-4-yl}-(5-fluoro-2,3-dihydro-indol-1-yl)-methanone | G | 454.0 | L (2.78) | — |
| {2-[4-(4-Amino-5-fluoro-pyrimidin-2-yloxy)-piperidin-1-yl]-thiazol-4-yl}-(2,3-dihydro-indol-1-yl)-methanone | G | 441.0 | L (3.05) | — |
| {2-[4-(4-Amino-5-fluoro-pyrimidin-2-yloxy)-piperidin-1-yl]-thiazol-5-yl}-(2,3-dihydro-indol-1-yl)-methanone | G | 440.9 | L (2.76) | — |
| {2-[4-(4-Amino-5-fluoro-pyrimidin-2-yloxy)-piperidin-1-yl]-oxazol-4-yl}-(2,3-dihydro-indol-1-yl)-methanone | G | 425.1 | L (2.70) | 56 |
| 6-[4-(4-Amino-5-fluoro-pyrimidin-2-yloxy)-piperidin-1-yl]-5-fluoro-pyrimidine-4-carboxylic acid isopropyl ester | G | 395.1 | L (2.48) | — |
| {6-[4-(4-Amino-5-fluoro-pyrimidin-2-yloxy)-piperidin-1-yl]-5-fluoro-pyrimidin-4-yl}-(2,3-dihydro-indol-1-yl)-methanone | G | 454.0 | L (2.64) | — |
| {6-[4-(4-Amino-5-fluoro-pyrimidin-2-yloxy)-piperidin-1-yl]-pyrimidin-4-yl}-(4-methyl-piperazin-1-yl)-methanone | G | 417.1 | L (1.63) | 57 |
| {6-[4-(4-Amino-5-fluoro-pyrimidin-2-yloxy)-piperidin-1-yl]-pyrimidin-4-yl}-(4-dimethylamino-piperidin-1-yl)-methanone | G | 445.1 | L (1.47) | — |
| [4-(4-Amino-5-fluoro-pyrimidin-2-yloxy)-piperidin-1-yl]-biphenyl-4-yl-methanone | H | 393.1 | K (1.90) | — |
| [4-(4-Amino-5-fluoro-pyrimidin-2-yloxy)-piperidin-1-yl]-naphthalen-1-yl-methanone | H | 367.1 | A (1.67) | 58 |
| 1-[4-(4-Amino-5-fluoro-pyrimidin-2-yloxy)-piperidin-1-yl]-2-(4-chloro-phenoxy)-ethanone | H | 381.0 and 383.0 | V (1.59) | 59 |
| [4-(4-Amino-5-fluoro-pyrimidin-2-yloxy)-piperidin-1-yl]-[2-(5-phenyl-thiophen-2-yl)-thiazol-4-yl]-methanone | H | 481.9 | V (2.24) | — |
| [4-(4-Amino-5-fluoro-pyrimidin-2-yloxy)-piperidin-1-yl]-(3,4-dichloro-phenyl)-methanone | H | 385 and 387.0 | V (1.60) | — |
| [4-(4-Amino-5-fluoro-pyrimidin-2-yloxy)-piperidin-1-yl]-(4-chloro-phenyl)-methanone | H | 351.1 and 353.1 | V (1.51) | — |
| 1-[4-(4-Amino-5-fluoro-pyrimidin-2-yloxy)-piperidin-1-yl]-2-phenoxy-ethanone | H | 347.0 | V (1.53) | — |
| 2-[4-(4-Amino-5-fluoro-pyrimidin-2-yloxy)-piperidin-1-yl]-N-(4-methoxy-phenyl)-acetamide | I | 376.0 | L (1.83) | 60 |

TABLE 2-continued

| Compound | Mthd | M + 1 | HPLC | NMR |
|---|---|---|---|---|
| 2-[4-(4-Amino-5-fluoro-pyrimidin-2-yloxy)-piperidin-1-yl]-1-(2,3-dihydro-indol-1-yl)-ethanone | I | 372.1 | L (1.88) | 61 |
| 2-[4-(4-Amino-5-fluoro-pyrimidin-2-yloxy)-piperidin-1-yl]-N-(2-cyano-phenyl)-acetamide | I | 371.4 | L (2.57) | — |
| 2-[4-(4-Amino-5-fluoro-pyrimidin-2-yloxy)-piperidin-1-yl]-N-naphthalen-2-yl-acetamide | I | 396.5 | L (2.39) | — |
| 2-[4-(4-Amino-5-fluoro-pyrimidin-2-yloxy)-piperidin-1-yl]-N-benzothiazol-5-yl-acetamide | I | 403.5 | L (2.17) | — |
| 2-[4-(4-Amino-5-fluoro-pyrimidin-2-yloxy)-piperidin-1-yl]-N-naphthalen-1-yl-acetamide | I | 396.0 | L (2.55) | — |
| 2-[4-(4-Amino-5-fluoro-pyrimidin-2-yloxy)-piperidin-1-yl]-N-benzothiazol-2-yl-acetamide | I | 403.0 | L (2.53) | — |
| 2-[4-(4-Amino-5-fluoro-pyrimidin-2-yloxy)-piperidin-1-yl]-N-(4-chloro-phenyl)-acetamide | I | 380.1 | L (2.61) | — |
| 2-[4-(4-Amino-5-fluoro-pyrimidin-2-yloxy)-piperidin-1-yl]-N-(4-cyano-phenyl)-acetamide | I | 371.0 | L (2.31) | — |
| 2-[4-(4-Amino-5-fluoro-pyrimidin-2-yloxy)-piperidin-1-yl]-N-(3-cyano-phenyl)-acetamide | I | 371.0 | L (2.28) | — |
| 2-[4-(4-Amino-5-fluoro-pyrimidin-2-yloxy)-piperidin-1-yl]-N-(2-fluoro-phenyl)-acetamide | I | 364.0 | L (2.46) | — |
| 2-[4-(4-Amino-5-fluoro-pyrimidin-2-yloxy)-piperidin-1-yl]-N-(2,4-dichloro-6-cyano-phenyl)-acetamide | I | 440.9 | L (2.63) | — |
| 2-[4-(4-Amino-5-fluoro-pyrimidin-2-yloxy)-piperidin-1-yl]-N-(2-phenoxy-phenyl)-acetamide | I | 438.0 | L (3.16) | — |
| 2-[4-(4-Amino-5-fluoro-pyrimidin-2-yloxy)-piperidin-1-yl]-N-(3-phenoxy-phenyl)-acetamide | I | 438.0 | L (3.06) | 62 |
| 2-[4-(4-Amino-5-fluoro-pyrimidin-2-yloxy)-piperidin-1-yl]-N-[4-(4-methoxy-phenoxy)-phenyl]-acetamide | I | 468.0 | L (2.85) | — |
| 2-[4-(4-Amino-5-fluoro-pyrimidin-2-yloxy)-piperidin-1-yl]-N-phenyl-acetamide | I | 346.1 | L (2.24) | — |
| 2-[4-(4-Amino-5-fluoro-pyrimidin-2-yloxy)-piperidin-1-yl]-N-(2,3-dichloro-phenyl)-acetamide | I | 415.9 | L (3.14) | — |
| 1-[4-(4-Amino-5-fluoro-pyrimidin-2-yloxy)-piperidin-1-yl]-2-(naphthalen-2-ylamino)-ethanone | I | 396.2 | L (2.78) | — |
| 1-[4-(4-Amino-5-fluoro-pyrimidin-2-yloxy)-piperidin-1-yl]-2-[(benzo[b]thiophen-2-ylmethyl)-amino]-ethanone | I | 416.1 | L (2.48) | 63 |
| 1-[4-(4-Amino-5-fluoro-pyrimidin-2-yloxy)-piperidin-1-yl]-2-(2,3-dichloro-phenylamino)-ethanone | I | 414.1 | L (2.98) | 64 |
| 2-[4-(4-Amino-5-fluoro-pyrimidin-2-yloxy)-piperidin-1-yl]-N-benzo[b]thiophen-5-yl-acetamide | I | 402.2 | L (2.61) | — |
| 2-[4-(4-Amino-5-fluoro-pyrimidin-2-yloxy)-piperidin-1-yl]-N-benzyl-acetamide | I | 360.2 | L (2.15) | 65 |
| 5-Fluoro-2-{1-[3-(4-fluoro-phenoxy)-propyl]-piperidin-4-yloxy}-pyrimidin-4-ylamine | J | 365.4 | L (2.48) | 66 |
| 5-Fluoro-2-{1-[3-(4-methoxy-phenoxy)-propyl]-piperidin-4-yloxy}-pyrimidin-4-ylamine | J | 377.0 | L (2.51) | — |
| {6-[4-(4-Amino-5-fluoro-pyrimidin-2-yloxy)-piperidin-1-yl]-pyrimidin-4-yl}-(4-methoxy-phenyl)-methanone | K | 425.0 | Y (2.04) | — |
| 2-{6-[4-(4-Amino-5-fluoro-pyrimidin-2-yloxy)-piperidin-1-yl]-pyrimidine-4-carbonyl}-benzamide | K | 438.1 | R (1.61) | 67 |
| 3-(6-(4-(4-amino-5-fluoropyrimidin-2-yloxy)piperidin-1-yl)-5-fluoropyrimidine-4-carbonyl)benzonitrile | K | 437.9 | R (2.58) | — |
| {6-[4-(4-Amino-5-fluoro-pyrimidin-2-yloxy)-piperidin-1-yl]-5-fluoro-pyrimidin-4-yl}-(4-methoxy-phenyl)-methanone | K | 442.9 | R (2.57) | 68 |
| {6-[4-(4-Amino-5-fluoro-pyrimidin-2-yloxy)-piperidin-1-yl]-pyrimidin-4-yl}-(2-fluoro-4-methoxy-phenyl)-methanone | K | 442.9 | R (2.39) | — |
| {6-[4-(4-Amino-5-fluoro-pyrimidin-2-yloxy)-piperidin-1-yl]-5-fluoro-pyrimidin-4-yl}-(2-methoxy-phenyl)-methanone | K | 443.0 | R (2.49) | — |
| 2-(1-{6-[Difluoro-(4-methoxy-phenyl)-methyl]-pyrimidin-4-yl}-piperidin-4-yloxy)-5-fluoro-pyrimidin-4-ylamine | L | 447.0 | R (2.65) | — |

TABLE 2-continued

| Compound | Mthd | M + 1 | HPLC | NMR |
|---|---|---|---|---|
| 2-(1-{6-[Difluoro-(2-fluoro-4-methoxy-phenyl)-methyl]-pyrimidin-4-yl}-piperidin-4-yloxy)-5-fluoro-pyrimidin-4-ylamine | L | 465.0 | R (2.76) | 69 |
| 5-Fluoro-2-(1-{6-[fluoro-(2-fluoro-4-methoxy-phenyl)-methyl]-pyrimidin-4-yl}-piperidin-4-yloxy)-pyrimidin-4-ylamine | L | 447.5 | R (2.59) | 70 |
| {6-[4-(4-Amino-5-fluoro-pyrimidin-2-yloxy)-piperidin-1-yl]-pyrimidin-4-yl}-(4-methoxy-phenyl)-methanol | M | 427.0 | R (1.88) | 71 |
| {6-[4-(4-Amino-5-fluoro-pyrimidin-2-yloxy)-piperidin-1-yl]-pyrimidin-4-yl}-(2-fluoro-4-methoxy-phenyl)-methanol | M | 445.5 | R (2.01) | 72 |
| {6-[4-(4-Amino-5-fluoro-pyrimidin-2-yloxy)-[1,4']bipiperidinyl-1'-yl]-pyrimidin-4-yl}-(4-methoxy-phenyl)-methanone oxime | N | 440.0 | R (2.03) | 73 |
| {6-[4-(4-Amino-5-fluoro-pyrimidin-2-yloxy)-piperidin-1-yl]-pyrimidin-4-yl}-(4-methoxy-phenyl)-methanone O-methyl-oxime | N | 454.0 | R (2.49) | 74 |
| 2-(2-{6-[4-(4-Amino-5-fluoro-pyrimidin-2-yloxy)-piperidin-1-yl]-pyrimidin-4-yloxy}-phenyl)-propan-2-ol | O | 441.0 | V (1.90) | — |
| 5-Fluoro-2-(1-{6-[2-(1-methyl-1H-pyrazol-4-yl)-phenoxy]-pyrimidin-4-yl}-piperidin-4-yloxy)-pyrimidin-4-ylamine | P | 463.1 | V (1.72) | — |
| 5-Fluoro-2-{1-[6-(2-pyridin-3-yl-phenoxy)-pyrimidin-4-yl]-piperidin-4-yloxy}-pyrimidin-4-ylamine | P | 460.1 | O (1.74) | 75 |
| 2-{1-[6-(Biphenyl-3-yloxy)-pyrimidin-4-yl]-piperidin-4-yloxy}-5-fluoro-pyrimidin-4-ylamine | P | 459.0 | S (2.59) | 76 |
| 3'-{6-[4-(4-Amino-5-fluoro-pyrimidin-2-yloxy)-piperidin-1-yl]-pyrimidin-4-yloxy}-biphenyl-4-carbonitrile | P | 483.9 | S (2.50) | — |
| 5-Fluoro-2-{1-[6-(2'-methoxy-biphenyl-3-yloxy)-pyrimidin-4-yl]-piperidin-4-yloxy}-pyrimidin-4-ylamine | P | 488.9 | S (2.58) | — |
| 5-Fluoro-2-{1-[6-(4'-methoxy-biphenyl-3-yloxy)-pyrimidin-4-yl]-piperidin-4-yloxy}-pyrimidin-4-ylamine | P | 488.9 | S (2.56) | — |
| 5-Fluoro-2-{1-[6-(3-pyridin-4-yl-phenoxy)-pyrimidin-4-yl]-piperidin-4-yloxy}-pyrimidin-4-ylamine | P | 460.0 | S (2.14) | — |
| 5-Fluoro-2-{1-[6-(3-pyridin-3-yl-phenoxy)-pyrimidin-4-yl]-piperidin-4-yloxy}-pyrimidin-4-ylamine | P | 460.0 | S (2.16) | — |
| 5-Fluoro-2-{1-[6-(2-pyridin-4-yl-phenoxy)-pyrimidin-4-yl]-piperidin-4-yloxy}-pyrimidin-4-ylamine | P | 460.0 | V (1.95) | — |
| 2-{1-[6-([3,4']Bipyridinyl-5-yloxy)-pyrimidin-4-yl]-piperidin-4-yloxy}-5-fluoro-pyrimidin-4-ylamine | P | 460.9 | S (1.90) | — |
| 2-{1-[6-([3,3']Bipyridinyl-5-yloxy)-pyrimidin-4-yl]-piperidin-4-yloxy}-5-fluoro-pyrimidin-4-ylamine | P | 460.9 | S (1.90) | — |
| 5-Fluoro-2-{1-[6-(2-pyrimidin-5-yl-phenoxy)-pyrimidin-4-yl]-piperidin-4-yloxy}-pyrimidin-4-ylamine | P | 395.0 | A (1.11) | — |
| 5-Fluoro-2-[1-(10-methylene-10H-9-oxa-1,3-diaza-anthracen-4-yl)-piperidin-4-yloxy]-pyrimidin-4-ylamine | P | 407.0 | A (1.49) | 77 |
| 5-Fluoro-2-(1-{6-[3-(1-methyl-1H-pyrazol-4-yl)-phenoxy]-pyrimidin-4-yl}-piperidin-4-yloxy)-pyrimidin-4-ylamine | P | 463.0 | S (2.09) | — |
| 5-Fluoro-2-(1-{6-[3-(1H-pyrazol-4-yl)-phenoxy]-pyrimidin-4-yl}-piperidin-4-yloxy)-pyrimidin-4-ylamine | P | 449.0 | S (1.97) | — |
| 5-Fluoro-2-{1-[6-(3-furan-2-yl-phenoxy)-pyrimidin-4-yl]-piperidin-4-yloxy}-pyrimidin-4-ylamine | P | 449.0 | S (2.45) | — |
| 5-Fluoro-2-{1-[6-(3-furan-3-yl-phenoxy)-pyrimidin-4-yl]-piperidin-4-yloxy}-pyrimidin-4-ylamine | P | 449.0 | S (2.42) | — |
| 2-{1-[6-(3-Cyclopropyl-phenoxy)-pyrimidin-4-yl]-piperidin-4-yloxy}-5-fluoro-pyrimidin-4-ylamine | P | 423.0 | S (2.43) | 78 |
| 2-{1-[6-(4-Cyclopropyl-phenoxy)-pyrimidin-4-yl]-piperidin-4-yloxy}-5-fluoro-pyrimidin-4-ylamine | P | 423.0 | S (2.45) | — |

TABLE 2-continued

| Compound | Mthd | M + 1 | HPLC | NMR |
|---|---|---|---|---|
| 2-{1-[6-(2-Cyclopropyl-phenoxy)-pyrimidin-4-yl]-piperidin-4-yloxy}-5-fluoro-pyrimidin-4-ylamine | P | 423.0 | S (2.38) | — |
| 2-[1-(5-Cyclopropyl-6-phenoxy-pyrimidin-4-yl)-piperidin-4-yloxy]-5-fluoro-pyrimidin-4-ylamine | P | 423.0 | S (2.45) | — |
| 2-{1-[5-Cyclopropyl-6-(2-cyclopropyl-phenoxy)-pyrimidin-4-yl]-piperidin-4-yloxy}-5-fluoro-pyrimidin-4-ylamine | P | 463.0 | S (2.64) | — |
| 5-Fluoro-2-(1-{5-fluoro-6-[2-(1-methyl-1H-pyrazol-4-yl)-phenoxy]-pyrimidin-4-yl}-piperidin-4-yloxy)-pyrimidin-4-ylamine | P | 480.9 | V (2.16) | — |
| 5-fluoro-2-(1-(4'-methoxybiphenyl-2-ylsulfonyl)piperidin-4-yloxy)pyrimidin-4-amine | P | 459.1 | A (2.02) | — |
| 5-Fluoro-2-[1-(5-oxa-2,4-diaza-dibenzo[a,d]cyclohepten-1-yl)-piperidin-4-yloxy]-pyrimidin-4-ylamine | Q | 407.0 | A (1.63) | 79 |
| 2-(1-(5-amino-6-(2-chloro-4-methoxyphenoxy)pyrimidin-4-yl)piperidin-4-yloxy)-5-fluoropyrimidin-4-amine | R | 462.0 | S (2.26) | 80 |
| 2-{1-[2-Amino-3-(4-methoxy-phenoxy)-phenyl]-piperidin-4-yloxy}-5-fluoro-pyrimidin-4-ylamine | R | 426.0 | S (2.60) | — |
| 2-(1-(5-amino-6-(4-methoxyphenoxy)pyrimidin-4-yl)piperidin-4-yloxy)-5-fluoropyrimidin-4-amine | R | 428.0 | S (2.11) | — |
| 2-(1-(5-amino-6-(3-methoxyphenoxy)pyrimidin-4-yl)piperidin-4-yloxy)-5-fluoropyrimidin-4-amine | R | 428.0 | S (2.14) | — |
| 4-{5-Amino-6-[4-(4-amino-5-fluoro-pyrimidin-2-yloxy)-piperidin-1-yl]-pyrimidin-4-yloxy}-3-methoxy-benzonitrile | R | 453.0 | S (2.09) | — |
| 2-{5-Amino-6-[4-(4-amino-5-fluoro-pyrimidin-2-yloxy)-piperidin-1-yl]-pyrimidin-4-yloxy}-5-methoxy-benzonitrile | R | 453.0 | S (2.15) | — |
| 3-{5-Amino-6-[4-(4-amino-5-fluoro-pyrimidin-2-yloxy)-piperidin-1-yl]-pyrimidin-4-yloxy}-benzonitrile | R | 423.0 | S (2.08) | — |
| 2-(1-(5-amino-6-(2-methoxyphenoxy)pyrimidin-4-yl)piperidin-4-yloxy)-5-fluoropyrimidin-4-amine | R | 428.0 | S (2.08) | — |
| 4-{5-Amino-6-[4-(4-amino-5-fluoro-pyrimidin-2-yloxy)-piperidin-1-yl]-pyrimidin-4-yloxy}-benzonitrile | R | 423.0 | S (2.06) | — |
| 2-{5-[4-(4-Amino-5-fluoro-pyrimidin-2-yloxy)-piperidin-1-yl]-tetrazol-2-ylmethyl}-benzonitrile | S | 396.2 | A (1.27) | — |
| 2-[1-(2-Benzyl-2H-tetrazol-5-yl)-piperidin-4-yloxy]-5-fluoro-pyrimidin-4-ylamine | S | 371.0 | Y (2.24) | — |
| 5-Fluoro-2-{1-[2-(4-nitro-benzyl)-2H-tetrazol-5-yl]-piperidin-4-yloxy}-pyrimidin-4-ylamine | S | 416.0 | Y (2.26) | — |
| 5-Fluoro-2-{1-[2-(4-methoxy-benzyl)-2H-tetrazol-5-yl]-piperidin-4-yloxy}-pyrimidin-4-ylamine | S | 401.0 | Y (2.25) | — |
| 2-(1-{6-[4-(2-Dimethylamino-ethoxy)-phenoxy]-5-fluoro-pyrimidin-4-yl}-piperidin-4-yloxy)-5-fluoro-pyrimidin-4-ylamine | T | 488.1 | L (2.34) | — |
| 2-(4-{6-[4-(4-Amino-5-fluoro-pyrimidin-2-yloxy)-piperidin-1-yl]-5-fluoro-pyrimidin-4-yloxy}-phenoxy)-ethanol | T | 461.0 | L (2.46) | 81 |
| 2-[1-(6-Biphenyl-4-yl-pyrimidin-4-yl)-piperidin-4-yloxy]-5-fluoro-pyrimidin-4-ylamine | U | 443.5 | B (1.49) | — |
| 2-[1-(6-Benzo[b]thiophen-2-yl-pyrimidin-4-yl)-piperidin-4-yloxy]-5-fluoro-pyrimidin-4-ylamine | U | 423.1 | M (1.66) | 82 |
| 5-Fluoro-2-{1-[6-(4'-methoxy-2'-methyl-biphenyl-4-yl)-pyrimidin-4-yl]-piperidin-4-yloxy}-pyrimidin-4-ylamine | U | 487.6 | B (1.21) | — |
| 1-(4'-{6-[4-(4-Amino-5-fluoro-pyrimidin-2-yloxy)-piperidin-1-yl]-pyrimidin-4-yl}-biphenyl-4-yl)-ethanol | U | 487.6 | B (1.21) | — |
| 2-[1-(6-Benzo[b]thiophen-2-yl-5-fluoro-pyrimidin-4-yl)-piperidin-4-yloxy]-5-fluoro-pyrimidin-4-ylamine | U | 441.1 | L (3.50) | — |
| [4-(4-Amino-5-fluoro-pyrimidin-2-yloxy)-piperidin-1-yl]-(4-benzo[b]thiophen-2-yl-pyridin-2-yl)-methanone | V | 450.1 | A (1.83) | — |
| [4-(4-Amino-5-fluoro-pyrimidin-2-yloxy)-piperidin-1-yl]-(5-benzo[b]thiophen-2-yl-2-fluoro-phenyl)-methanone | V | 466.9 | V (2.42) | — |

TABLE 2-continued

| Compound | Mthd | M + 1 | HPLC | NMR |
|---|---|---|---|---|
| [4-(4-Amino-5-fluoro-pyrimidin-2-yloxy)-piperidin-1-yl]-(5-benzo[b]thiophen-2-yl-2,4-dimethoxy-phenyl)-methanone | V | 508.9 | V (2.36) | — |
| [4-(4-Amino-5-fluoro-pyrimidin-2-yloxy)-piperidin-1-yl]-[2-(5-methyl-benzo[b]thiophen-2-yl)-thiazol-4-yl]-methanone | V | 470.0 | N (2.29) | — |
| [4-(4-Amino-5-fluoro-pyrimidin-2-yloxy)-piperidin-1-yl]-[2-(4-chloro-2-methyl-phenyl)-thiazol-4-yl]-methanone | V | 447.9 | N (2.22) | 83 |
| [4-(4-Amino-5-fluoro-pyrimidin-2-yloxy)-piperidin-1-yl]-(2-benzo[b]thiophen-2-yl-thiazol-4-yl)-methanone | V | 455.9 | N (2.18) | — |
| [4-(4-Amino-5-fluoro-pyrimidin-2-yloxy)-piperidin-1-yl]-(4-benzo[b]thiophen-2-yl-3-methoxy-thiophen-2-yl)-methanone | V | 484.9 | N (2.39) | — |
| N-{6-[4-(4-Amino-5-fluoro-pyrimidin-2-yloxy)-piperidin-1-yl]-pyrimidin-4-yl}-2-methoxy-benzamide | W | 440.0 | L (2.67) | 84 |
| 3-[4-(4-Amino-5-fluoro-pyrimidin-2-yloxy)-piperidin-1-ylmethyl]-benzonitrile | X | 328.1 | V (1.75) | — |
| 5-Fluoro-2-[1-(4-imidazol-1-yl-benzyl)-piperidin-4-yloxy]-pyrimidin-4-ylamine | X | 369.0 | V (1.45) | — |
| 5-Fluoro-2-{1-[5-fluoro-6-(2-methoxy-5-morpholin-4-ylmethyl-phenoxy)-pyrimidin-4-yl]-piperidin-4-yloxy}-pyrimidin-4-ylamine | X | 530.1 | F (1.08) | — |
| 5-Fluoro-2-(1-{5-fluoro-6-[2-methoxy-5-(4-methyl-piperazin-1-ylmethyl)-phenoxy]-pyrimidin-4-yl}-piperidin-4-yloxy)-pyrimidin-4-ylamine | X | 543.1 | G (1.84) | — |
| 2-{1-[6-(5-Dimethylaminomethyl-2-methoxy-phenoxy)-5-fluoro-pyrimidin-4-yl]-piperidin-4-yloxy}-5-fluoro-pyrimidin-4-ylamine | X | 488.1 | F (1.05) | — |
| 2-{1-[6-(5-Diethylaminomethyl-2-methoxy-phenoxy)-5-fluoro-pyrimidin-4-yl]-piperidin-4-yloxy}-5-fluoro-pyrimidin-4-ylamine | X | 516.1 | F (1.31) | — |
| 5-Fluoro-2-{1-[5-fluoro-6-(2-methoxy-4-morpholin-4-ylmethyl-phenoxy)-pyrimidin-4-yl]-piperidin-4-yloxy}-pyrimidin-4-ylamine | X | 530.3 | G (1.84) | — |
| 2-{1-[6-(4-Cyclopropylaminomethyl-2-methoxy-phenoxy)-5-fluoro-pyrimidin-4-yl]-piperidin-4-yloxy}-5-fluoro-pyrimidin-4-ylamine | X | 500.2 | G (1.95) | — |
| 2-{1-[6-(4-Dimethylaminomethyl-2-methoxy-phenoxy)-5-fluoro-pyrimidin-4-yl]-piperidin-4-yloxy}-5-fluoro-pyrimidin-4-ylamine | X | 488.3 | G (1.82) | — |
| 5-Fluoro-2-(1-{5-fluoro-6-[2-methoxy-4-(4-methyl-piperazin-1-ylmethyl)-phenoxy]-pyrimidin-4-yl}-piperidin-4-yloxy)-pyrimidin-4-ylamine | X | 543.3 | G (1.91) | — |
| 2-{1-[6-(4-Dimethylaminomethyl-3-methoxy-phenoxy)-5-fluoro-pyrimidin-4-yl]-piperidin-4-yloxy}-5-fluoro-pyrimidin-4-ylamine | X | 488.1 | S (2.16) | 85 |
| 5-Fluoro-2-{1-[5-fluoro-6-(3-methoxy-4-morpholin-4-ylmethyl-phenoxy)-pyrimidin-4-yl]-piperidin-4-yloxy}-pyrimidin-4-ylamine | X | 530.0 | S (2.23) | — |
| 2-{1-[6-(4-Cyclopropylaminomethyl-3-methoxy-phenoxy)-5-fluoro-pyrimidin-4-yl]-piperidin-4-yloxy}-5-fluoro-pyrimidin-4-ylamine | X | 498.0 | S (2.29) | — |
| 3-{6-[4-(4-Amino-5-fluoro-pyrimidin-2-yloxy)-piperidin-1-yl]-5-fluoro-pyrimidin-4-yloxy}-5-methoxy-benzonitrile | Y | 456.0 | S (2.18) | — |
| 5-Fluoro-2-{(S)-1-[2-methyl-9-(tetrahydro-furan-2-ylmethyl)-9H-purin-6-yl]-pyrrolidin-3-yloxy}-pyrimidin-4-ylamine | D | 379.0 | CC (1.16) | — |
| 2-[(R)-1-(Biphenyl-4-sulfonyl)-pyrrolidin-3-yloxy]-5-fluoro-pyrimidin-4-ylamine | D | 415.1 | BB (1.63) | — |
| [(S)-3-(4-Amino-5-fluoro-pyrimidin-2-yloxy)-pyrrolidin-1-yl]-acetic acid phenyl ester | C | 333.2 | L (2.02) | — |
| [(S)-3-(4-Amino-5-fluoro-pyrimidin-2-yloxy)-pyrrolidin-1-yl]-(4-benzo[b]thiophen-2-yl-pyridin-2-yl)-methanone | D | 436.0 | S (1.79) | 86 |
| 2-[(S)-1-(5-Ethyl-pyrimidin-2-yl)-pyrrolidin-3-yloxy]-5-fluoro-pyrimidin-4-ylamine | C | 305.1 | BB (1.48) | — |
| 5-Fluoro-2-((S)-1-quinoxalin-2-yl-pyrrolidin-3-yloxy)-pyrimidin-4-ylamine | C | 327.1 | BB (1.68) | — |
| 2-[(S)-1-(4-Chloro-phthalazin-1-yl)-pyrrolidin-3-yloxy]-5-fluoro-pyrimidin-4-ylamine | C | 361.1 | BB (1.55) | — |

TABLE 2-continued

| Compound | Mthd | M + 1 | HPLC | NMR |
|---|---|---|---|---|
| 2-{(S)-1-[9-(3,4-Dimethoxy-benzyl)-2-methyl-9H-purin-6-yl]-pyrrolidin-3-yloxy}-5-fluoro-pyrimidin-4-ylamine | C | 481.2 | BB (2.05) | — |
| 1-[(S)-3-(4-Amino-5-fluoro-pyrimidin-2-yloxy)-pyrrolidin-1-yl]-2-benzyloxy-ethanone | D | 347.1 | DD (0.46) | — |
| 1-[(S)-3-(4-Amino-5-fluoro-pyrimidin-2-yloxy)-pyrrolidin-1-yl]-3-phenyl-propan-1-one | D | 331.1 | DD (0.48) | — |
| [(S)-3-(4-Amino-5-fluoro-pyrimidin-2-yloxy)-pyrrolidin-1-yl]-[2-(2,3-dichloro-phenyl)-thiazol-4-yl]-methanone | D | 454.0 | DD (0.5) | — |
| [(S)-3-(4-Amino-5-fluoro-pyrimidin-2-yloxy)-pyrrolidin-1-yl]-(5-bromo-2,3-dihydro-benzofuran-7-yl)-methanone | D | 423.0 | DD (0.53) | — |
| [(S)-3-(4-Amino-5-fluoro-pyrimidin-2-yloxy)-pyrrolidin-1-yl]-(2-phenyl-thiazol-4-yl)-methanone | D | 386.1 | DD (0.61) | — |
| [(S)-3-(4-Amino-5-fluoro-pyrimidin-2-yloxy)-pyrrolidin-1-yl]-[2-(2,3-dihydro-benzofuran-5-yl)-thiazol-4-yl]-methanone | D | 428.1 | DD (0.71) | — |
| (S)-3-(4-Amino-5-fluoro-pyrimidin-2-yloxy)-pyrrolidine-1-carboxylic acid (4-phenoxy-phenyl)-amide | D | 410.2 | DD (0.77) | — |
| (S)-3-(4-Amino-5-fluoro-pyrimidin-2-yloxy)-pyrrolidine-1-carboxylic acid naphthalen-2-ylamide | D | 368.1 | DD (0.68) | — |
| (S)-3-(4-Amino-5-fluoro-pyrimidin-2-yloxy)-pyrrolidine-1-carboxylic acid biphenyl-4-ylamide | D | 394.2 | DD (0.78) | — |
| (S)-3-(4-Amino-5-fluoro-pyrimidin-2-yloxy)-pyrrolidine-1-carboxylic acid phenethyl-amide | D | 346.2 | DD (0.56) | — |
| (S)-3-(4-Amino-5-fluoro-pyrimidin-2-yloxy)-pyrrolidine-1-carboxylic acid cyclohexylamide | D | 324.2 | DD (0.55) | — |
| (S)-3-(4-Amino-5-fluoro-pyrimidin-2-yloxy)-pyrrolidine-1-carboxylic acid (4-dimethylamino-phenyl)-amide | D | 361.2 | DD (0.51) | — |
| 5-Fluoro-2-((S)-1-phenylmethanesulfonyl-pyrrolidin-3-yloxy)-pyrimidin-4-ylamine | C | 353.1 | DD (0.60) | — |
| 5-Fluoro-2-[(S)-1-(3-trifluoromethyl-benzenesulfonyl)-pyrrolidin-3-yloxy]-pyrimidin-4-ylamine | D | 407.1 | DD (0.77) | — |
| 2-[(S)-1-(2,3-Dichloro-benzenesulfonyl)-pyrrolidin-3-yloxy]-5-fluoro-pyrimidin-4-ylamine | D | 407.0 | DD (0.78) | — |
| 5-Fluoro-2-[(S)-1-(5-fluoro-2-methyl-benzenesulfonyl)-pyrrolidin-3-yloxy]-pyrimidin-4-ylamine | D | 371.1 | DD (0.72) | — |
| 5-Fluoro-2-[(S)-1-(toluene-3-sulfonyl)-pyrrolidin-3-yloxy]-pyrimidin-4-ylamine | D | 353.1 | DD (0.66) | — |
| 5-Fluoro-2-[(S)-1-(4-isopropyl-benzenesulfonyl)-pyrrolidin-3-yloxy]-pyrimidin-4-ylamine | D | 381.1 | DD (0.84) | — |
| 2-[(S)-3-(4-Amino-5-fluoro-pyrimidin-2-yloxy)-pyrrolidine-1-sulfonyl]-benzonitrile | D | 364.1 | DD (0.57) | — |
| 5-Fluoro-2-[(S)-1-(4-fluoro-benzenesulfonyl)-pyrrolidin-3-yloxy]-pyrimidin-4-ylamine | D | 357.1 | DD (0.62) | — |
| 5-Fluoro-2-[(S)-1-(naphthalene-1-sulfonyl)-pyrrolidin-3-yloxy]-pyrimidin-4-ylamine | D | 389.1 | DD (0.76) | — |
| 5-Fluoro-2-[(S)-1-((E)-2-phenyl-ethenesulfonyl)-pyrrolidin-3-yloxy]-pyrimidin-4-ylamine | D | 365.1 | DD (0.69) | — |
| 5-Fluoro-2-[(S)-1-(4-phenoxy-benzenesulfonyl)-pyrrolidin-3-yloxy]-pyrimidin-4-ylamine | D | 431.1 | DD (0.89) | — |
| 5-Fluoro-2-((S)-1-naphthalen-2-ylmethyl-pyrrolidin-3-yloxy)-pyrimidin-4-ylamine | X | 339.2 | DD (0.48) | — |
| 2-[(S)-1-((1R,5S)-6,6-Dimethyl-bicyclo[3.1.1]hept-2-en-2-ylmethyl)-pyrrolidin-3-yloxy]-5-fluoro-pyrimidin-4-ylamine | X | 333.2 | DD (0.53) | — |
| 5-Fluoro-2-((S)-1-pyridin-4-ylmethyl-pyrrolidin-3-yloxy)-pyrimidin-4-ylamine | X | 290.1 | DD (0.18) | — |
| 2-[(S)-1-(4-Dimethylamino-benzyl)-pyrrolidin-3-yloxy]-5-fluoro-pyrimidin-4-ylamine | X | 332.2 | DD (0.26) | — |
| 5-Fluoro-2-[(S)-1-(4-methoxy-benzyl)-pyrrolidin-3-yloxy]-pyrimidin-4-ylamine | X | 319.1 | DD (0.37) | — |
| 5-Fluoro-2-[(S)-1-(4-trifluoromethoxy-benzyl)-pyrrolidin-3-yloxy]-pyrimidin-4-ylamine | X | 373.1 | DD (0.51) | — |
| 2-((S)-1-Biphenyl-4-ylmethyl-pyrrolidin-3-yloxy)-5-fluoro-pyrimidin-4-ylamine | X | 365.2 | DD (0.57) | — |

TABLE 2-continued

| Compound | Mthd | M + 1 | HPLC | NMR |
|---|---|---|---|---|
| 2-((S)-1-Benzofuran-2-ylmethyl-pyrrolidin-3-yloxy)-5-fluoro-pyrimidin-4-ylamine | X | 329.1 | DD (0.42) | — |
| 5-Fluoro-2-[(S)-1-(3-phenoxy-benzyl)-pyrrolidin-3-yloxy]-pyrimidin-4-ylamine | X | 381.2 | DD (0.57) | — |
| 2-[(S)-1-(2,3-Dihydro-benzo[1,4]dioxin-6-ylmethyl)-pyrrolidin-3-yloxy]-5-fluoro-pyrimidin-4-ylamine | X | 347.1 | DD (0.37) | — |
| 5-Fluoro-2-[(S)-1-(3-phenyl-butyl)-pyrrolidin-3-yloxy]-pyrimidin-4-ylamine | X | 331.2 | DD (0.49) | — |
| 1-{4'-[(S)-3-(4-Amino-5-fluoro-pyrimidin-2-yloxy)-pyrrolidin-1-ylmethyl]-biphenyl-3-yl}-ethanone | X | 407.2 | DD (0.52) | — |
| 2-[(S)-1-(4-Benzyloxy-3-methoxy-benzyl)-pyrrolidin-3-yloxy]-5-fluoro-pyrimidin-4-ylamine | X | 425.2 | DD (0.58) | — |
| 5-Fluoro-2-[(S)-1-(2,3,4-trimethoxy-benzyl)-pyrrolidin-3-yloxy]-pyrimidin-4-ylamine | X | 379.2 | DD (0.41) | — |
| 2-[(S)-1-(4'-Chloro-biphenyl-3-ylmethyl)-pyrrolidin-3-yloxy]-5-fluoro-pyrimidin-4-ylamine | X | 399.1 | DD (0.64) | — |
| 2-[(S)-1-(3',4'-Dimethyl-biphenyl-2-ylmethyl)-pyrrolidin-3-yloxy]-5-fluoro-pyrimidin-4-ylamine | X | 393.2 | DD (0.64) | — |
| 2-[(S)-1-(3-Cyclopentyloxy-4-methoxy-benzyl)-pyrrolidin-3-yloxy]-5-fluoro-pyrimidin-4-ylamine | X | 403.2 | DD (0.52) | — |
| (S)-3-(4-Amino-5-fluoro-pyrimidin-2-yloxy)-pyrrolidine-1-carboxylic acid (3-benzo[b]thiophen-2-yl-phenyl)-amide | D | 449.8 | L (3.14) | — |
| 4-Amino-5-fluoro-1-{1-[6-(4-methoxy-phenoxy)-pyrimidin-4-yl]-azepan-4-yl}-1H-pyrimidin-2-one | C | 427.5 | A (1.63) | — |

$^1$H NMR data for certain compounds listed above are provided in Table 3:

TABLE 3

1 (300 MHz, DMSO-d6) δ ppm: 8.43 (s, 1H) 7.88 (s, 1H) 7.75-7.70 (m, 4H) 7.27 (d, J = 9.2 Hz, 1H) 5.20-5.12 (m, 1H) 4.02-3.92 (m, 2H) 3.75 (s, 3H) 3.60-3.49 (m, 2H) 2.06-1.95 (m, 2H) 1.74-1.61 (m, 2H)

2 (400 MHz, MeOD-d4) δ ppm: 1.73-1.76 (m, 2H) 1.98-2.06 (m, 2H) 3.54-3.67 (m, 2H) 3.92 (s, 2H) 3.97-4.03 (m, 2H) 5.13-5.19 (m, 1H) 6.69 (s, 1H) 7.20-7.32 (m, 5H) 7.82 (d, J = 3.32 Hz, 1H) 8.37 (d, J = 0.98 Hz, 1H)

3 (300 MHz MeOD-d4) δ ppm: 1.15 (t, 6H, 3H), 1.67 (m, 2H), 1.91 (m, 2H), 2.58 (q, 9.0 Hz, 8.0 Hz, 2H), 3.44 (m, 2H), 3.82 (m, 2H), 5.05 (m, 1H), 5.94 (s, 1H), 6.93 (m, 2H), 1.17 (m, 2H), 7.72 (d, 6.0 Hz, 1H, 8.06 (s, 1H)

4 (400 MHz MeOD-d4) δ ppm: 1.76 (m, 2H), 2.02 (m, 2H), 3.53 (m, 2H), 3.91 (m, 2H), 5.15 (m, 1H), 6.99 (m, 1H), 7.11 (m, 2H), 7.25 (m, 1H) 7.82 (d, 3.6 Hz, 1H), 8.10 (d, 0.8 Hz, 1H)

5 (400 MHz MeOD-d4) δ ppm: 1.77 (m, 2H), 2.04 (m, 2H), 3.56 (m, 2H), 3.82 (s, 3H), 3.95 (m, 2H), 5.16 (m, 1H), 6.099 d, 0.8 Hz, 1H), 6.93 (d, 8.8 Hz, 1H), 7.07 (d, 2.8 hz, 1H), 7.14 (d, 8.4 Hz, 1H), 7.82 (d, 3.2 Hz, 1H), 8.12 (d, 0.8 Hz, 1H)

6 (400 MHz, MeOD-d4) δ ppm: 1.69-1.78 (m, 2H) 1.99 (br. s., 2H) 3.38-3.45 (m, 2H) 3.79 (s, 3H) 3.83 (s, 2H) 5.09-5.15 (m, 1H) 5.82 (d, J = 0.98 Hz, 1H) 6.89-6.93 (m, 2H) 7.24-7.28 (m, 2H) 7.81 (d, J = 3.32 Hz, 1H) 8.05 (d, J = 0.78 Hz, 1H)

7 (400 MHz, MeOD-d4) δ ppm: 1.64 (m, 2H), 1.91 (m, 2H), 3.32 (m, 2H), 3.72 (m, 2H), 3.77 (s, 3H), 3.79 (s, 3H), 5.06 (m, 1H), 5.06 (s, 1H), 6.91 (m, 4H), 7.02 (m, 4H), 7.79 (d, 3.6 Hz, 1H)

8 (400 MHz, MeOD-d4) δ ppm: 1.62-1.72 (m, J = 8.43, 8.43, 4.49, 4.25 Hz, 2H) 1.91-2.00 (m, 2H) 3.25-3.33 (m, 2H) 3.35 (s, 3H) 3.71-3.79 (m, 2H) 3.82 (s, 3H) 5.04-5.11 (m, 1H) 5.45 (s, 1H) 7.01 (d, J = 8.99 Hz, 2H) 7.17 (d, J = 8.79 Hz, 2H) 7.79 (d, J = 3.32 Hz, 1H) 8.08 (s, 1H)

9 (400 MHz, MeOD-d4) δ ppm: 1.74-1.83 (m, 2H) 2.01-2.08 (m, 2H) 3.56-3.64 (m, 2H) 3.95-4.03 (m, 2H) 5.14-5.20 (m, J = 7.35, 7.35, 3.57, 3.42 Hz, 1H) 6.29 (s, 1H) 7.42-7.47 (m, J = 9.67, 4.05, 3.76, 2.83 Hz, 1H) 7.53-7.55 (m, 1H) 7.59 (ddd, J = 3.57, 1.71, 1.56 Hz, 2H) 7.82 (d, J = 3.32 Hz, 1H) 8.17 (d, J = 0.78 Hz, 6H)

10 (400 MHz, DMSO-d6) δ ppm: 8.18 (s, 1H) 7.97-7.91 (m, 2H) 7.89 (d, J = 8.0 Hz, 2H) 7.34 (s, 1H) 7.25 (s, 2H) 7.17 (d, J = 8.0 Hz, 2H) 6.42 (s, 1H) 5.08-5.00 (m, 1H) 4.04-3.87 (m, 2H) 3.50-3.40 (m, 2H) 2.01-1.91 (m, 2H) 1.65-1.54 (m, 2H)

TABLE 3-continued 11  (300 MHz, CDCl₃) δ ppm: 1.44 (t, J = 6.96 Hz, 3H) 1.73-2.16 (m, 4H)
    3.51-3.99 (m, 4H) 4.05 (q, J = 6.87 Hz, 2H) 5.09 (br. s., 2H) 5.12-5.23 (m, 1H)
    5.91 (s, 1H) 6.99 (dd, 2H) 7.92 (d, J = 2.67 Hz, 1H) 8.35 (s, 1H)
12  (400 MHz, MeOD-d4) δ ppm: 1.64-1.81 (m, 2H) 1.91-2.05 (m, 2H)
    3.51-3.60 (m, 1H) 3.76-3.83 (m, 4H) 3.84-3.92 (m, 1H) 4.10-4.19 (m, 1H)
    5.09-5.17 (m, 1H) 6.92-6.98 (m, 2H) 7.05-7.11 (m, 2H) 7.81 (d, J = 3.52 Hz, 1H)
    8.32 (s, 1H)
13  (400 MHz, MeOH) δ ppm: 7.80 (d, J = 3.5 Hz, 2H) 7.22 (ddd, J = 1.5, 7.4, 7.4 Hz,
    1H) 7.11-7.06 (m, 2H) 6.97 (ddd, J = 1.5, 7.6, 7.6 Hz, 1H) 5.27 (s, 1H)
    5.13-5.07 (m, 1H) 3.88-3.81 (m, 2H) 3.78 (s, 3H) 3.41-3.33 (m, 2H) 2.01-1.97 (m,
    2H) 1.73-1.64 (m, 2H)
14  (400 MHz, MeOH) δ ppm: 7.80 (d, J = 3.5 Hz, 1H) 7.20 (ddd, J = 8.2, 7.4, 1.8 Hz,
    1H) 7.10-7.06 (m, 2H) 6.96 (ddd, J = 1.5, 7.6, 7.6 Hz, 1H) 5.17 (s, 1H)
    5.12-5.06 (m, 1H) 3.92-3.83 (m, 2H) 3.77 (s, 3H) 3.39-3.31 (m, 2H) 2.02-1.94 (m,
    2H) 1.73-1.63 (m, 2H)
15  (400 MHz, MeOD-d4) δ ppm: 1.41 (s, 6H) 1.71-1.79 (m, 2H) 1.98-2.05 (m,
    2H) 3.08 (s, 2H) 3.49-3.57 (m, 2H) 3.88-3.96 (m, 2H) 5.14 (tt, J = 7.42,
    3.71 Hz, 1H) 5.99 (s, 1H) 6.82-6.92 (m, 2H) 7.07 (dd, J = 7.23, 1.17 Hz, 1H)
    7.81 (d, J = 3.52 Hz, 1H) 8.13 (d, J = 0.78 Hz, 1H)
16  (300 MHz, CDCl₃) δ ppm: 1.83 (ddd, J = 13.49, 6.82, 3.91 Hz, 2H) 1.96 (dd,
    J = 8.20, 4.20 Hz, 2H) 3.55 (ddd, J = 13.21, 3.67, 3.53 Hz, 2H) 3.88 (ddd,
    J = 13.02, 3.96, 3.62 Hz, 2H) 5.11 (td, J = 7.01, 3.72 Hz, 1H) 5.17 (br. s., 2H)
    6.02 (s, 1H) 7.48 (t, J = 2.19 Hz, 1H) 7.82 (d, J = 2.48 Hz, 1H) 8.20 (s, 1H)
    8.32 (dd, J = 15.74, 2.00 Hz, 2H)
17  (300 MHz, MeOH) δ ppm: 1.67-1.81 (m, 2H) 1.90-2.08 (m, 2H)
    2.96-3.04 (m, 4H) 3.46-3.61 (m, 6H) 3.75-3.88 (m, 1H) 3.88-3.98 (m, 1H) 5.15 (tt,
    J = 7.41, 3.55 Hz, 1H) 5.95 (s, 1H) 7.07-7.15 (m, 3H) 7.21-7.31 (m, 1H)
    7.82 (d, J = 3.43 Hz, 1H) 8.17 (d, J = 0.57 Hz, 1H)
18  (300 MHz, CDCl₃) δ ppm: 1.75-1.88 (m, 2H) 1.92-2.03 (m, 2H)
    3.47-3.58 (m, 2H) 3.81-3.93 (m, 2H) 4.97 (br. s., 2H) 5.10 (dt, J = 7.15, 3.48 Hz, 1H)
    5.95 (s, 1H) 6.78-6.90 (m, 3H) 7.23-7.33 (m, 1H) 7.84 (d, J = 2.67 Hz, 1H)
    8.25 (s, 1H)
19  (400 MHz, CDCl₃) δ ppm: 1.80-2.03 (m, 4H) 3.65-3.75 (m, 1H) 3.79 (s, 3H)
    3.83-3.94 (m, 2H) 4.03-4.11 (m, 1H) 5.14 (d, J = 3.32 Hz, 3H)
    6.93-7.00 (m, 2H) 7.12 (dd, J = 7.82, 1.56 Hz, 1H) 7.19-7.24 (m, 1H) 7.90 (d, J = 2.54 Hz,
    1H)
20  (400 MHz, MeOD-d4) δ ppm: 1.94 (br. s., 2H) 2.15 (br. s., 2H) 3.59 (br. s., 2H)
    3.98 (br. s., 2H) 5.18 (br. S., 1H) 7.12-7.25 (m, 2H) 7.40 (td, J = 7.72, 1.56 Hz,
    1H) 7.65 (dd, J = 7.82, 1.17 Hz, 1H) 7.78 (s, 1H) 7.83 (d, J = 3.52 Hz, 1H)
21  (400 MHz, CDCl₃) δ ppm: 1.79 (s, 2H) 1.93 (s, 2H) 3.49 (s, 2H) 3.74 (s, 3H)
    3.74-3.84 (m, 2H) 4.96 (s, 2H) 5.07 (s, 1H) 5.64 (d, J = 3.13 Hz, 2H)
    6.76-6.88 (m, 2H) 6.97 (s, 2H) 7.82 (d, J = 2.54 Hz, 2H)
22  (400 MHz, CDCl₃) δ ppm: 8.22 (s, 1H) 7.82 (d, J = 2.7 Hz, 1H) 7.26 (d, J = 9.5 Hz,
    1H) 6.70-6.67 (m, 2H) 5.99 (s, 1H) 5.17 (s, 2H) 5.13-5.05 (m, 1H)
    3.92-3.89 (m, 2H) 3.71 (s, 3H) 3.56-3.47 (m, 2H) 2.03-1.93 (m, 2H) 1.86-1.76 (m,
    2H)
23  (400 MHz, CDCl₃) δ ppm: 8.19 (s, 1H) 7.85 (d, J = 2.5 Hz, 1H) 7.49 (dd, J = 2.0,
    8.5 Hz, 1H) 7.35 (d, J = 1.95 Hz, 1H) 6.97 (d, J = 8.6 Hz, 1H) 6.05 (s, 1H)
    5.16-5.09 (m, 1H) 5.06 (s, 2H) 3.94-3.85 (m, 2H) 3.78 (s, 3H) 3.63-3.53 (m, 2H)
    2.04-1.95 (m, 2H) 1.90-1.81 (m, 2H)
24  (300 MHz, CDCl₃) δ ppm: 1.94 (s, 2H) 2.02-2.18 (m, 2H) 3.19-3.38 (m, 2H)
    3.57-3.75 (m, 2H) 3.82 (s, 3H) 5.05 (br. s., 2H) 5.14 (s, 1H) 6.23 (d,
    J = 2.29 Hz, 1H) 6.46 (dd, J = 6.10, 2.29 Hz, 1H) 6.99 (dd, 4H) 7.90 (d, J = 6.10 Hz,
    1H) 7.92 (d, J = 2.67 Hz, 1H)
25  (400 MHz, MeOD-d4) δ ppm: 1.92-2.01 (m, 2H) 2.14-2.23 (m, 2H)
    3.82 (br. s., 2H) 4.06 (br. s., 2H) 5.43-5.49 (m, 1H) 7.13 (d, J = 0.78 Hz, 1H)
    7.23-7.35 (m, 3H) 7.58 (d, J = 8.01 Hz, 1H) 8.19 (d, J = 5.08 Hz, 1H) 8.62 (s, 1H)
26  (300 MHz, MeOH) δ ppm: 2.13 (dd, J = 6.77, 3.53 Hz, 1H) 2.34 (dd, J = 13.54,
    4.01 Hz, 1H) 3.33 (t, J = 2.48 Hz, 1H) 3.88-4.03 (m, 5H) 4.04-4.18 (m, 1H)
    5.55 (d, J = 3.24 Hz, 1H) 6.24 (br. s., 3H) 7.37 (d, J = 8.77 Hz, 1H) 7.67 (d,
    J = 1.91 Hz, 1H) 7.75 (dd, J = 8.58, 1.91 Hz, 1H) 8.16 (s, 1H) 8.23 (d, J = 4.77 Hz,
    1H)
27  (400 MHz, MeOD-d4) δ ppm: 1.93-2.05 (m, 2H) 2.11-2.25 (m, 2H)
    3.80-3.93 (m, 2H) 3.98-4.09 (m, 2H) 5.46 (s, 3H) 6.48 (s, 1H) 7.61 (t, J = 7.82 Hz,
    1H) 7.72-7.82 (m, 2H) 7.86 (s, 1H) 8.18 (d, J = 4.88 Hz, 1H) 8.38 (s, 1H)
28  (300 MHz, CDCl₃) δ ppm: 1.86-1.98 (m, 2H) 2.03-2.14 (m, 2H)
    3.58-3.69 (m, 2H) 3.93-4.03 (m, 2H) 5.07 (br. s., 2H) 5.16-5.24 (m, J = 7.06, 7.06,
    3.81, 3.62 Hz, 1H) 6.18 (s, 1H) 7.31 (d, J = 0.76 Hz, 1H) 7.43 (td, J = 7.63, 1.14 Hz,
    1H) 7.63 (td, J = 7.82, 1.72 Hz, 1H) 7.93 (d, J = 2.67 Hz, 1H) 8.16 (dd,
    J = 7.92, 1.62 Hz, 1H) 8.23 (s, 1H) 8.43 (s, 1H)
29  (400 MHz, DMSO-d6) δ ppm: 7.98 (s, 1H) 7.92 (d, J = 3.3 Hz, 1H)
    7.27-7.23 (m, 6H) 5.09-5.02 (m, 1H) 4.06-3.97 (m, 2H) 3.61-3.51 (m, 2H) 2.08-1.98 (m,
    2H) 1.73-1.62 (m, 2H)
30  (400 MHz, CDCl₃) δ ppm: 1.93 (s, 2H) 2.09-2.14 (m, 2H) 2.16 (s, 3H)
    2.35 (s, 3H) 3.21 (s, 2H) 3.60-3.77 (m, 2H) 3.81 (s, 3H) 5.02 (s, 2H)
    5.04-5.16 (m, 1H) 6.95 (dd, 4H) 7.91 (d, J = 2.74 Hz, 1H)
31  (400 MHz, MeOD-d4) δ ppm: 1.75-1.83 (m, 2H) 2.01-2.08 (m, 2H) 2.20 (s,
    3H) 3.58 (s, 3H) 3.59-3.65 (m, 2H) 3.99 (br. s., 2H) 5.15-5.20 (m, 1H)
    5.82 (s, 1H) 6.34 (d, J = 0.78 Hz, 1H) 7.82 (d, J = 3.52 Hz, 1H) 8.19 (d, J = 0.78 Hz,
    1H)

TABLE 3-continued 32 (400 MHz, MeOD-d4) δ ppm: 1.66-1.80 (m, 3H) 1.85-1.99 (m, 5H)
2.20-2.30 (m, 2H) 3.22 (ddd, J = 9.57, 8.01, 5.86 Hz, 1H) 3.34-3.45 (m, 2H)
3.75-3.88 (m, 2H) 5.08-5.14 (m, 1H) 5.20 (dd, J = 5.86, 3.13 Hz, 1H) 5.84 (s, 1H)
7.15-7.20 (m, 1H) 7.27 (s, 2H) 7.28 (d, J = 0.78 Hz, 2H) 7.81 (d, J = 3.32 Hz, 1H)
8.10 (s, 1H)

33 (400 MHz, MeOD-d4) δ ppm: 1.73-1.82 (m, 2H) 2.00-2.08 (m, 2H)
3.55-3.62 (m, 2H) 3.94-4.02 (m, 2H) 5.14-5.20 (m, 1H) 6.22 (s, 1H)
7.08-7.12 (m, 1H) 7.30 (dd, J = 6.25, 2.74 Hz, 2H) 7.82 (d, J = 3.52 Hz, 1H) 8.16 (d,
J = 0.78 Hz, 1H)

34 (300 MHz, CDCl$_3$) δ ppm: 1.82-1.99 (m, 2H) 2.00-2.15 (m, 2H) 3.22 (t,
J = 8.39 Hz, 2H) 3.48-3.95 (m, 2H) 3.95-4.08 (m, 4H) 5.16 (tt, J = 7.30, 3.67 Hz,
1H) 5.77 (s, 1H) 6.91 (t, J = 7.34 Hz, 1H) 7.17-7.24 (m, 2H) 7.92 (d,
J = 2.29 Hz, 1H) 8.28 (d, J = 8.20 Hz, 1H) 8.40 (s, 1H)

35 (300 MHz, CDCl$_3$) δ ppm: 2.05-2.27 (m, 4H) 3.21-3.33 (m, 1H)
3.44-3.56 (m, 2H) 3.84 (s, 3H) 5.07 (br. s., 1H) 5.17 (ddd, J = 6.29, 3.05, 2.86 Hz, 1H)
6.30 (d, J = 8.39 Hz, 1H) 6.66 (d, J = 8.01 Hz, 1H) 6.89-6.98 (m, 2H)
7.02-7.10 (m, 2H) 7.93 (d, J = 2.67 Hz, 1H)

36 (400 MHz, MeOD-d4) δ ppm: 1.79 (dd, J = 13.09, 3.71 Hz, 2H) 1.95-2.05 (m,
2H) 3.52 (d, J = 8.40 Hz, 2H) 3.80 (s, 3H) 3.85 (br. s., 2H) 5.19 (br. s., 1H)
5.84 (s, 1H) 6.11 (d, J = 5.86 Hz, 1H) 6.90-6.97 (m, 2H) 6.99-7.06 (m, 2H)
7.82 (d, J = 6.06 Hz, 1H) 8.17 (s, 1H)

37 (400 MHz, CDCl$_3$) δ ppm: 1.90 (td, J = 6.59, 3.81 Hz, 2H) 2.00-2.09 (m, 2H)
3.62 (d, J = 4.49 Hz, 2H) 3.83 (br. s., 3H) 3.93 (br. s., 2H) 5.11 (br. s., 2H)
5.27 (br. s., 1H) 6.09 (s, 1H) 6.11 (d, J = 5.86 Hz, 1H) 7.02 (d, J = 8.60 Hz, 1H)
7.40 (d, J = 1.95 Hz, 1H) 7.53 (dd, J = 8.50, 2.05 Hz, 1H) 8.00 (d, J = 5.67 Hz, 1H)
8.22 (s, 1H)

38 (300 MHz, CDCl$_3$) δ ppm: 1.93-2.04 (m, 2H) 2.04-2.15 (m, 2H)
2.96-3.09 (m, 2H) 3.22-3.36 (m, 2H) 3.82 (s, 3H) 5.08 (br. s., 3H) 6.54 (d, J = 8.20 Hz,
1H) 6.86-6.97 (m, 3H) 7.03 (d, J = 8.77 Hz, 2H) 7.20-7.34 (m, 2H) 7.92 (br.
s., 1H)

39 (300 MHz, MeOH) δ ppm: 1.67-1.82 (m, 2H) 1.87-2.01 (m, 2H)
3.40-3.54 (m, 2H) 3.74-3.86 (m, 2H) 5.12-5.23 (m, 1H) 5.92 (s, 1H) 7.15 (d, J = 8.77 Hz,
2H) 7.63 (d, J = 8.77 Hz, 2H) 7.76-7.84 (m, 1H) 7.97 (s, 1H) 8.11 (s, 1H)
8.61 (br. s., 1H)

40 (400 MHz, DMSO-d6) δ ppm: 7.96 (d, J = 1.0 Hz, 1H) 7.62 (d, J = 3.3 Hz, 1H)
7.45 (d, J = 9.0 Hz, 1H) 7.25, (s, 2H) 6.99 (d, J = 2.9 Hz, 1H) 6.89 (dd, J = 2.9, 9.0 Hz,
1H) 5.10-5.02 (m, 1H) 3.74 (s, 3H) 3.62-3.54 (m, 2H) 2.09-1.99 (m, 2H)
1.73-1.63 (m, 2H)

41 (400 MHz, DMSO-d6) δ ppm: 8.20 (s, 1H) 7.91 (d, J = 3.3 Hz, 1H) 7.24 (s, 2H)
6.08, (s, 1H) 5.04-4.97 (m, 1H) 4.25 (q, J = 7.0 Hz, 2H) 3.95-3.87 (m, 2H)
3.41-3.33 (m, 2H) 1.97-1.88 (m, 2H) 1.60-1.50 (m, 2H) 1.25 (t, J = 7.0 Hz, 3H)

42 (300 MHz, CDCl$_3$) δ ppm: 1.39-1.66 (m, 2H) 1.84-1.98 (m, 2H)
3.03-3.18 (m, 2H) 3.70-3.84 (m, 2H) 4.85 (ddd, J = 8.54, 4.48, 4.34 Hz, 1H) 4.93 (br. s.,
2H) 6.46 (d, J = 8.58 Hz, 1H) 6.80 (dd, J = 7.72, 4.86 Hz, 1H) 7.03 (t, J = 7.63 Hz,
1H) 7.22-7.38 (m, 2H) 7.56 (d, J = 7.63 Hz, 1H) 7.79 (d, J = 2.48 Hz, 1H)
8.09 (d, J = 3.24 Hz, 1H)

43 (300 MHz, MeOH) δ ppm: 1.71-1.85 (m, 2H) 1.97-2.10 (m, 2H)
3.48-3.61 (m, 2H) 3.70 (t, J = 4.86 Hz, 2H) 3.89-4.00 (m, 2H) 4.05 (t, J = 4.96 Hz, 2H)
5.17 (tt, J = 7.32, 3.46 Hz, 1H) 6.06 (s, 1H) 6.99-7.07 (m, 1H) 7.12-7.20 (m,
2H) 7.20-7.29 (m, 1H) 7.84 (d, J = 3.24 Hz, 1H) 8.14 (s, 1H)

44 (400 MHz, DMSO-d6) δ ppm: 1.74 (d, J = 8.79 Hz, 2H) 2.06 (br. s., 2H)
3.64 (t, J = 9.57 Hz, 2H) 4.09 (d, J = 6.64 Hz, 2H) 5.09 (br. s., 1H) 7.27 (br. s., 2H)
7.87 (d, J = 0.78 Hz, 1H) 7.91-7.96 (m, 2H) 8.05-8.14 (m, 2H) 8.20 (d,
J = 9.38 Hz, 3H) 8.34 (d, J = 8.60 Hz, 3H)

45 (300 MHz, DMSO-d6) δ ppm: 1.63-1.76 (m, 2H) 1.99-2.11 (m, 2H)
3.52-3.65 (m, 2H) 3.82 (s, 3H) 3.99-4.15 (m, 2H) 5.10-5.19 (m, 1H) 6.07 (d,
J = 5.72 Hz, 1H) 6.84 (br. s., 2H) 7.34 (d, J = 9.16 Hz, 1H) 7.76-7.82 (m,
J = 4.53, 2.31, 2.31, 2.10 Hz, 2H) 7.86 (d, J = 5.72 Hz, 1H) 7.94 (d, J = 0.76 Hz, 1H)

46 (300 MHz, DMSO-d6) δ ppm: 1.73 (td, J = 8.20, 4.01 Hz, 2H) 2.06 (ddd,
J = 9.35, 6.58, 3.15 Hz, 2H) 3.66 (dd, J = 8.96, 3.05 Hz, 1H) 4.07 (td, J = 6.72,
2.57 Hz, 2H) 5.16 (dt, J = 7.58, 3.74 Hz, 1H) 6.07 (d, J = 5.72 Hz, 1H) 6.84 (br.
s., 2H) 7.44-7.53 (m, 2H) 7.80 (dd, J = 16.02, 1.53 Hz, 1H) 7.86 (d, J = 5.72 Hz,
1H) 7.96 (dd, J = 7.63, 1.34 Hz, 1H) 8.03 (s, 1H)

47 (300 MHz, MeOH) δ ppm: 1.77-1.89 (m, 2H) 2.06-2.16 (m, 2H)
2.96-3.03 (m, 2H) 3.19-3.25 (m, 2H) 3.62-3.73 (m, 2H) 3.78 (s, 3H) 4.07-4.17 (m, 2H)
5.12-5.21 (m, 1H) 6.91 (dd, J = 8.11, 1.81 Hz, 1H) 7.05 (d, J = 1.72 Hz, 1H)
7.10 (d, J = 8.01 Hz, 1H) 7.82-7.84 (m, 2H)

48 (300 MHz, MeOH) δ ppm: 1.35 (t, J = 7.25 Hz, 6H) 1.79-1.91 (m, 2H)
2.08-2.18 (m, 2H) 3.03-3.12 (m, 4H) 3.26 (q, J = 7.25 Hz, 4H) 3.64-3.73 (m, 2H)
3.80 (s, 3H) 4.08-4.20 (m, 2H) 5.12-5.26 (m, 1H) 6.95 (dd, J = 8.11, 1.62 Hz,
1H) 7.07-7.13 (m, 2H) 7.81-7.88 (m, 2H)

49 (300 MHz, MeOH) δ ppm: 1.31 (t, J = 7.25 Hz, 6H) 1.76-1.87 (m, 2H)
2.06-2.19 (m, 2H) 2.98-3.07 (m, 2H) 3.12-3.28 (m, 6H) 3.64-3.77 (m, 2H)
3.80 (s, 3H) 4.08-4.23 (m, 2H) 5.22-5.33 (m, 1H) 6.16 (d, J = 5.91 Hz, 1H)
6.94 (dd, J = 8.01, 1.91 Hz, 1H) 7.07 (d, J = 1.91 Hz, 1H) 7.10 (d, J = 8.01 Hz, 1H)
7.83 (s, 1H) 7.87 (d, J = 5.91 Hz, 1H)

TABLE 3-continued 50 (300 MHz, CDCl₃) δ ppm: 0.98 (t, J = 7.34 Hz, 3H) 1.43-1.55 (m, 3H)
1.71-1.82 (m, 2H) 1.86-1.98 (m, 2H) 2.05-2.17 (m, 2H) 3.65-3.77 (m, 2H)
3.96 (t, J = 6.48 Hz, 2H) 4.05-4.17 (m, 2H) 5.06 (br. s., 2H) 5.17 (tt, J = 7.32, 3.55 Hz,
1H) 6.89-6.95 (m, 2H) 7.03-7.11 (m, 2H) 7.92 (d, J = 2.48 Hz, 1H)
8.01 (s, 1H)
51 (400 MHz, MeOD) δ ppm: 1.34 (t, J = 7.28 Hz, 6H) 1.84 (td, J = 8.53, 4.02 Hz, 2H)
1.95 (s, 3H) 2.08 (br. s., 2H) 3.01-3.11 (m, 2H) 3.26 (q, J = 7.36 Hz, 4H)
3.29-3.35 (m, 2H) 3.63-3.73 (m, 2H) 4.12 (ddd, J = 13.24, 7.34, 3.26 Hz, 2H)
5.17 (br. s., 1H) 7.13 (d, J = 8.53 Hz, 2H) 7.37 (d, J = 8.53 Hz, 2H) 7.83 (d,
J = 3.26 Hz, 1H) 7.91 (s, 1H)
52 (400 MHz, DMSO-d6) δ ppm: 1.43-1.55 (m, 1H) 1.86 (br. s., 2H)
3.38-3.43 (m, 2H) 3.81 (s, 3H) 3.89 (br. s., 2H) 4.94-5.02 (m, J = 7.94, 7.94, 3.95, 3.76 Hz,
1H) 6.21 (d, J = 5.52 Hz, 1H) 7.27 (br. s., 1H) 7.33 (d, J = 8.53 Hz, 1H)
7.73-7.82 (m, 2H) 7.92 (d, J = 3.51 Hz, 1H) 8.24 (d, J = 5.52 Hz, 1H)
53 (400 MHz, DMSO-d6) δ ppm: 1.52-1.64 (m, J = 12.33, 8.20, 8.20, 3.89 Hz, 2H)
1.89-2.00 (m, 2H) 3.35-3.45 (m, 1H) 3.79 (s, 3H) 3.85 (br. s., 2H)
5.03 (ddd, J = 7.72, 4.14, 3.95 Hz, 1H) 6.61 (d, J = 6.27 Hz, 1H) 7.23 (s, 2H) 7.28 (d,
J = 8.53 Hz, 1H) 7.66 (d, J = 2.01 Hz, 1H) 7.71 (dd, J = 8.53, 2.01 Hz, 1H)
7.93 (t, 1H)
54 (400 MHz, CDCl₃) δ ppm: 1.78-1.88 (m, 2H) 1.90-2.00 (m, 2H)
3.53-3.93 (m, 7H) 4.95-5.10 (m, 3H) 6.68 (d, J = 7.82 Hz, 2H) 6.77-6.84 (m, 2H)
6.87-6.92 (m, 2H) 6.99-7.06 (m, 1H) 7.17-7.21 (m, 1H) 7.28 (d, J = 6.45 Hz, 1H)
7.82 (d, J = 2.34 Hz, 1H)
55 (400 MHz, MeOD-d4) δ ppm: 1.77-1.86 (m, 2H) 2.02-2.10 (m, 2H) 3.16 (t,
J = 8.21 Hz, 2H) 3.71 (br. s., 2H) 4.04 (br. s., 2H) 4.12 (t, 2H) 5.16-5.23 (m,
1H) 7.01-7.13 (m, 2H) 7.20-7.30 (m, 2H) 7.82 (d, J = 3.32 Hz, 1H) 8.16 (d,
J = 8.01 Hz, 1H) 8.53 (s, 1H)
56 (400 MHz, MeOD-d4) δ ppm: 1.80-1.89 (m, 2H) 2.04-2.12 (m, 2H) 3.20 (t,
2H) 3.47-3.54 (m, 2H) 3.80-3.87 (m, 2H) 4.45-4.49 (m, 2H) 4.93 (m, 1H)
5.10-5.16 (m, 1H) 7.04-7.09 (m, 1H) 7.16-7.21 (m, 1H) 7.26 (d, J = 7.62 Hz,
1H) 7.82 (d, J = 3.52 Hz, 1H) 7.95 (s, 1H)
57 (400 MHz, MeOD) δ ppm: 1.78-1.86 (m, 2H) 2.03-2.10 (m, 2H) 2.41 (s, 3H)
2.57 (t, 2H) 2.65 (t, 2H) 3.51 (t, 2H) 3.70 (br. s., 2H) 3.79 (t, 2H)
4.03 (br. s., 2H) 5.20 (dd, J = 10.79, 3.51 Hz, 1H) 6.94 (s, 1H) 7.84 (d, J = 3.51 Hz, 1H)
8.49 (s, 1H)
58 (400 MHz, CDCl₃) δ ppm: 1.16 (none, 1H) 1.63-1.72 (m, 1H)
1.75-1.84 (m, 1H) 1.98-2.05 (m, 1H) 2.11-2.19 (m, 1H) 3.10-3.18 (m, J = 13.60, 3.60,
3.60, 3.42 Hz, 1H) 3.41-3.49 (m, 1H) 3.83-3.95 (m, 1H) 4.12-4.24 (m, 1H)
5.11-5.17 (m, 1H) 5.21-5.28 (m, 2H) 7.40-7.53 (m, 4H) 7.80-7.88 (m,
4H)
59 (300 MHz, MeOH) δ ppm: 1.69-1.88 (m, 2H) 1.93-2.10 (m, 1H)
1.93-2.10 (m, 1H) 3.46-3.62 (m, 2H) 3.73-3.89 (m, 1H) 3.73-3.89 (m, 1H) 4.83 (s, 2H)
5.10-5.18 (m, 1H) 6.96 (d, J = 8.96 Hz, 2H) 7.27 (d, J = 8.96 Hz, 2H)
7.82 (d, J = 3.24 Hz, 1H)
60 (300 MHz, MeOH) δ ppm: 1.87-1.98 (m, 2H) 2.06-2.15 (m, 2H) 2.58 (t,
J = 8.30 Hz, 2H) 2.87-2.95 (m, 2H) 3.23 (s, 2H) 3.79 (s, 3H) 4.96-5.02 (m,
1H) 6.91 (d, J = 8.77 Hz, 2H) 7.48 (d, J = 8.77 Hz, 2H) 7.83 (d, J = 3.43 Hz, 1H)
61 (300 MHz, MeOH) δ ppm: 1.88 (td, J = 8.15, 4.29 Hz, 2H) 2.08 (td, J = 7.77,
3.34 Hz, 2H) 2.55 (t, J = 9.16 Hz, 2H) 2.86-2.96 (m, 2H) 3.22 (t, J = 8.39 Hz, 2H)
3.38 (s, 2H) 4.20 (t, J = 8.39 Hz, 2H) 4.96 (d, J = 4.01 Hz, 1H) 7.05 (t, 1H)
7.17 (t, J = 7.82 Hz, 1H) 7.25 (d, J = 7.44 Hz, 1H) 7.82 (d, J = 3.24 Hz, 1H)
8.15 (d, J = 8.01 Hz, 1H)
62 (300 MHz, MeOH) δ ppm: 1.81-1.98 (m, 2H) 2.02-2.15 (m, 2H) 2.52 (t, 1H)
2.79-2.92 (m, 2H) 3.18 (s, 2H) 4.96-5.04 (m, 1H) 6.71-6.79 (m, 1H)
7.00 (d, 1H) 7.13 (t, J = 7.34 Hz, 1H) 7.27-7.44 (m, 5H) 7.82 (d, J = 3.43 Hz, 1H)
63 (300 MHz, MeOH) δ ppm: 1.83-2.01 (m, 2H) 2.03-2.20 (m, 2H) 3.47 (ddd,
J = 11.21, 7.10, 6.87 Hz, 1H) 3.66 (ddd, J = 17.36, 3.72, 3.53 Hz, 2H) 3.86 (ddd,
J = 17.40, 3.86, 3.72 Hz, 1H) 4.24 (s, 2H) 4.62 (s, 2H) 5.42 (dt, J = 7.01, 3.46 Hz,
1H) 7.40-7.48 (m, 2H) 7.63 (s, 1H) 7.85-7.97 (m, 2H) 8.22 (d, J = 4.96 Hz,
1H)
64 (300 MHz, MeOH) δ ppm: 1.79-2.03 (m, 2H) 2.04-2.27 (m, 2H)
3.52-3.75 (m, 1H) 3.75-3.96 (m, 2H) 4.12 (s, 2H) 5.35-5.48 (m, 1H) 6.66 (dd,
J = 8.30, 1.24 Hz, 1H) 6.82 (dd, J = 8.01, 1.14 Hz, 1H) 7.13 (t, J = 8.20 Hz, 1H)
8.19 (dd, J = 4.67, 2.96 Hz, 1H)
65 (300 MHz, DMSO-d6) δ ppm: 1.71 (br. s., 2H) 1.92 (br. s., 2H) 2.33 (br. s., 2H)
2.69 (br. s., 2H) 2.99 (br. s., 2H) 3.08-3.20 (m, J = 7.32, 7.32, 7.20, 4.48 Hz,
1H) 3.56-3.69 (m, J = 13.04, 6.46, 6.34, 4.29 Hz, 1H) 4.30 (d, J = 6.29 Hz,
2H) 4.79 (td, J = 7.49, 3.72 Hz, 1H) 7.17-7.36 (m, 7H) 7.91 (d, J = 3.24 Hz, 1H)
8.32 (br. s., 1H)
66 (400 MHz, MeOD) δ ppm: 1.78-1.91 (m, 2H) 1.96-2.10 (m, 2H) 2.41 (t,
J = 7.20 Hz, 2H) 2.59 (t, 1H) 2.83 (br. s., 2H) 4.01 (t, J = 6.06 Hz, 2H) 4.95 (dt,
J = 7.52, 3.69 Hz, 1H) 6.90 (dd, 1H) 7.00 (t, J = 8.72 Hz, 2H) 7.82 (d, J = 3.28 Hz,
1H)
67 (400 MHz, MeOD-d4) δ ppm: 1.76-1.86 (m, 2H) 2.02-2.11 (m, 2H)
3.63-3.72 (m, 2H) 4.01-4.10 (m, 2H) 5.16-5.22 (m, 1H) 7.31 (d, J = 0.98 Hz, 1H)
7.43 (d, J = 7.23 Hz, 1H) 7.51-7.61 (m, J = 14.92, 7.43, 7.43, 7.43, 1.07 Hz, 2H)
7.76 (dd, J = 7.42, 0.78 Hz, 1H) 7.83 (d, J = 3.52 Hz, 1H) 8.31 (d, J = 1.17 Hz, 1H)
68 (400 MHz, MeOD-d4) δ ppm: 1.73-1.83 (m, 2H) 1.98-2.07 (m, 2H)
3.68-3.77 (m, 2H) 3.81 (s, 3H) 4.01-4.09 (m, 2H) 5.07-5.14 (m, 1H)
6.94-7.00 (m, 2H) 7.74 (d, J = 3.52 Hz, 1H) 7.76-7.81 (m, 2H) 8.26 (d, J = 2.93 Hz, 1H)

TABLE 3-continued 69 (400 MHz, MeOD-d4) δ ppm: 1.78-1.89 (m, 2H) 2.02-2.12 (m, 2H)
3.67-3.78 (m, 2H) 3.83 (s, 3H) 3.99-4.11 (m, 2H) 5.17-5.24 (m, 1H) 6.74 (dd,
J = 13.09, 2.34 Hz, 1H) 6.85 (dd, J = 8.89, 2.25 Hz, 1H) 7.14 (s, 1H) 7.58 (t,
J = 8.79 Hz, 1H) 7.83 (d, J = 3.52 Hz, 1H) 8.42 (s, 1H)

70 (400 MHz, MeOD-d4) δ ppm: 1.77-1.87 (m, 2H) 2.04-2.11 (m, 2H)
3.65-3.75 (m, 2H) 3.80 (s, 3H) 4.01-4.11 (m, 2H) 5.16-5.23 (m, 1H) 6.47 (d,
J = 46.70 Hz, 1H) 6.74 (t, J = 2.34 Hz, 1H) 6.76 (s, 1H) 7.03 (s, 1H)
7.16-7.22 (m, 1H) 7.83 (d, J = 3.52 Hz, 1H) 8.36 (s, 1H)

71 (400 MHz, MeOD-d4) δ ppm: 1.75-1.85 (m, 2H) 2.02-2.10 (m, 2H)
3.61-3.70 (m, 2H) 3.76 (s, 3H) 3.99-4.08 (m, 2H) 5.18 (d, J = 3.13 Hz, 1H)
5.49 (s, 1H) 6.85-6.89 (m, 2H) 7.05 (s, 1H) 7.27-7.32 (m, 2H) 7.83 (d, J = 3.32 Hz,
1H) 8.32 (d, J = 0.98 Hz, 1H)

72 (400 MHz, MeOD-d4) δ ppm: 1.76-1.85 (m, 2H) 2.03-2.10 (m, 2H)
3.62-3.70 (m, 2H) 3.77 (s, 3H) 4.00-4.08 (m, 2H) 5.16-5.22 (m, 1H) 5.79 (s, 1H)
6.66-6.72 (m, 2H) 7.07 (s, 1H) 7.17 (t, J = 8.60 Hz, 1H) 7.83 (d, J = 3.52 Hz,
1H) 8.32 (d, J = 0.98 Hz, 1H)

73 (400 MHz, DMSO-d6) δ ppm: 1.57-1.66 (m, 4H) 1.94-2.02 (m, 4H)
3.45-3.54 (m, 4H) 3.76 (s, 6H) 3.93-4.02 (m, 4H) 5.02-5.08 (m, 2H)
6.91-6.95 (m, 4H) 7.07 (d, J = 1.17 Hz, 2H) 7.25 (br. s., 4H) 7.32-7.36 (m, 4H) 7.92 (d,
J = 3.32 Hz, 2H) 8.41 (d, J = 0.98 Hz, 2H) 11.68 (s, 2H)

74 (400 MHz, MeOD-d4) δ ppm: 1.76-1.86 (m, 6H) 2.03-2.10 (m, 6H)
3.62-3.72 (m, 6H) 3.80 (s, 6H) 3.83 (s, 3H) 3.90 (s, 6H) 3.99 (s, 3H)
3.99-4.09 (m, 6H) 5.15-5.21 (m, 3H) 6.79 (d, 3H) 6.88-6.97 (m, 6H) 7.37-7.45 (m,
6H) 7.82 (d, 3H) 8.40 (d, 1H) 8.51 (d, 2H)

75 (300 MHz, MeOH) δ ppm: 1.68-1.80 (m, 2H) 1.90-2.06 (m, 2H)
3.08-3.12 (m, 1H) 3.28-3.42 (m, 2H) 3.44-3.58 (m, 2H) 5.12-5.19 (m, 1H)
6.05-6.08 (m, 1H) 7.23-7.28 (m, 1H) 7.41-7.48 (m, 2H) 7.50-7.58 (m, 2H)
7.84 (d, J = 3.43 Hz, 1H) 7.96 (ddd, J = 8.01, 1.91, 1.72 Hz, 1H) 8.06 (s, 1H)
8.46 (dd, J = 4.96, 1.53 Hz, 1H) 8.62-8.66 (m, 1H)

76 (300 MHz, CDCl3) δ ppm: 1.75-2.03 (m, 4H) 3.54 (d, J = 8.01 Hz, 1H)
3.73 (s, 3H) 3.77-3.90 (m, 1H) 3.85 (dd, J = 9.54, 4.20 Hz, 1H) 5.00 (br. s., 2H)
5.07 (dd, J = 6.68, 3.43 Hz, 1H) 5.90 (s, 1H) 6.87-7.05 (m, 3H)
7.20-7.39 (m, 5H) 7.82 (d, J = 2.48 Hz, 1H) 8.28 (s, 1H)

77 (400 MHz, MeOD-d4) δ ppm: 1.83 (br. s., 2H) 2.05 (d, J = 4.10 Hz, 2H)
3.48 (ddd, J = 13.33, 8.25, 3.42 Hz, 2H) 3.81 (br. s., 2H) 5.13 (br. s., 1H) 5.49 (s, 1H)
5.69 (s, 1H) 7.18 (dd, J = 8.11, 1.07 Hz, 1H) 7.23 (td, J = 7.57, 1.27 Hz, 1H)
7.33-7.40 (m, 1H) 7.68 (dd, J = 7.91, 1.47 Hz, 1H) 7.81 (d, J = 3.52 Hz, 1H)
8.24 (s, 1H)

78 (300 MHz, CDCl3) δ ppm: 0.56-0.70 (m, 2H) 0.89 (d, J = 6.87 Hz, 2H)
1.45-1.59 (m, 1H) 1.73-1.87 (m, 3H) 1.87-2.02 (m, 2H) 3.39-3.55 (m, 2H)
3.78-3.92 (m, 2H) 4.98 (br. s., 2H) 5.03-5.14 (m, 1H) 5.87 (s, 1H) 6.73 (s, 1H)
6.78-6.91 (m, 2H) 7.82 (d, J = 1.91 Hz, 1H) 8.24 (s, 1H)

79 (400 MHz, MeOD-d4) δ ppm: 1.76-1.89 (m, 2H) 1.99-2.13 (m, J = 16.61,
3.81, 3.66, 3.66 Hz, 2H) 3.48 (br. s., 2H) 3.87 (d, J = 9.77 Hz, 2H) 5.14 (br. s., 1H)
6.40 (d, J = 11.14 Hz, 1H) 6.88 (d, J = 11.14 Hz, 1H) 7.14-7.30 (m, 3H)
7.31-7.41 (m, 1H) 7.81 (d, J = 3.52 Hz, 1H) 8.26 (s, 1H)

80 (300 MHz, MeOH) δ ppm: 1.78-1.94 (m, 2H) 2.03-2.14 (m, 2H)
2.97-3.15 (m, 2H) 3.54-3.65 (m, 2H) 3.73 (s, 3H) 4.91-5.05 (m, 1H) 6.85 (d, J = 2.86 Hz,
1H) 6.98 (d, J = 3.05 Hz, 1H) 7.08 (d, J = 8.96 Hz, 1H) 7.66 (s, 1H) 7.73 (d,
J = 3.24 Hz, 1H 81 (400 MHz, MeOD) δ ppm: 1.69-1.78 (m, 2H) 1.97-2.05 (m, 2H) 2.47 (s, 6H)
2.96 (t, J = 5.27 Hz, 2H) 3.55-3.62 (m, 2H) 3.98-4.05 (m, 2H) 4.10 (t,
J = 5.27 Hz, 2H) 5.08 (tt, J = 7.53, 3.76 Hz, 1H) 6.90-7.00 (m, 4H) 7.73 (d,
J = 3.26 Hz, 1H) 7.79 (s, 1H)

82 (400 MHz, DMSO-d6) δ ppm: 1.44-1.75 (m, 2H) 1.83-2.11 (m, 2H)
3.58 (s, 2H) 4.08 (s, 2H) 5.08 (s, 1H) 7.26 (s, 2H) 7.40 (s, 2H) 7.54 (s, 1H)
7.87 (s, 1H) 7.93 (d, J = 3.32 Hz, 1H) 7.99 (s, 1H) 8.40 (s, 1H) 8.50 (d, J = 1.17 Hz,
1H)

83 (400 MHz, MeOD-d4) δ ppm: 1.89 (br. s., 2H) 2.09 (br. s., 2H) 2.59 (s, 3H)
3.78 (br. s., 2H) 4.04 (br. s., 2H) 5.17-5.23 (m, 1H) 7.34 (dd, J = 8.40, 1.76 Hz,
1H) 7.41 (d, J = 1.95 Hz, 1H) 7.73 (d, J = 8.21 Hz, 1H) 7.82 (d, J = 3.32 Hz,
1H) 8.10 (s, 1H)

84 (400 MHz, MeOD-d4) δ ppm: 1.77-1.86 (m, 2H) 2.04-2.12 (m, 2H)
3.61-3.68 (m, 2H) 4.00-4.08 (m, 2H) 4.11 (s, 3H) 4.61 (br. s., 1H) 5.16-5.22 (m,
1H) 7.14 (dd, J = 15.04, 0.98 Hz, 1H) 7.24 (d, J = 8.40 Hz, 1H) 7.60 (dd, J = 8.40,
7.23 Hz, 1H) 7.74 (d, J = 0.98 Hz, 1H) 7.83 (d, J = 3.32 Hz, 1H) 8.11 (dd,
J = 7.82, 1.76 Hz, 1H) 8.28 (d, J = 0.98 Hz, 1H)

85 (400 MHz, MeOD) δ ppm: 1.70-1.79 (m, 2H) 2.02 (ddd, J = 13.05, 3.76, 3.51 Hz,
2H) 2.36 (s, 6H) 3.61 (ddd, J = 13.68, 4.14, 4.02 Hz, 2H) 3.68 (s, 2H)
3.75 (s, 3H) 4.03 (ddd, J = 13.36, 7.34, 3.39 Hz, 2H) 5.09 (tt, J = 7.43, 3.73 Hz, 1H)
6.65 (dd, J = 8.28, 2.26 Hz, 1H) 6.77 (d, J = 2.01 Hz, 1H) 7.23 (d, J = 8.28 Hz, 1H)
7.73 (d, J = 3.26 Hz, 1H) 7.83 (s, 1H)

86 (300 MHz, MeOH) δ ppm: 2.12-2.27 (m, 2H) 3.69-3.92 (m, 3H)
5.35-5.47 (m, 1H) 7.33 (td, J = 3.81, 1.53 Hz, 1H) 7.68-7.87 (m, 2H) 7.68-7.87 (m,
J = 18.48, 3.22, 3.08, 3.08 Hz, 2H) 8.01 (d, J = 1.91 Hz, 1H) 7.95-8.09 (m, 1H)
8.55 (dd, J = 8.39, 5.15 Hz, 1H)

6.32. Cloning, Expression and Purification of Recombinant Deoxycytidine Kinase A full-length cDNA of deoxycytidine kinase was obtained by RT-PCR using known primers with human lymph node RNA (Clontech, Mountain View, Calif.) as template. This full length ORF was cloned into pCR4Blunt-Topo (Invitrogen, Carlsbad, Calif.). Protein expression and purification was adapted from the procedure described by Sabini et al., *Nature Structure Biology* 10, 513-519 (2003).

Here, the full length ORF of deoxycytidine kinase was subcloned into pET28(a+) (Novagen, San Diego, Calif.) using endonucleases (Nde1 and Xho1). The plasmid was transformed into a bacterial strain BL21 (DE3). A single colony was picked and grown in LB broth containing Kanamycin 50 µg/ml and 2% glucose. Cells were grown at 37° C. until $OD_{600}$ was 0.6. Then, 0.1 mM IPTG was added and the culture incubated at 30° C. for 16 hours. Cells were harvested by centrifugation and resuspended in 50 ml of 50 mM Tris, pH 8.0 containing 1 mg/ml of Lysozyme, 10% glycerol and 10 mM $MgCl_2$, 50 µg/ml of DNase 1 and 1 tablet of Roche protein inhibitor cocktail and incubated on ice for 30 minutes. Cells were then disrupted on ice using a homogenizer. Whole cell lysate were cleared by centrifugation at 20,000 rpm for 20 minutes. The supernatant was loaded onto a Ni-NTA Sepharose column (20 ml of bed volume) preequilibrated with 50 mM Tris, pH 8.0, containing 10 mM $MgCl_2$, 10% glycerol. The column was washed with the same buffer containing 20 mM imidazole until $OD_{280}$ reached the baseline at a flow rate of 2 ml/min. Deoxycytidine kinase was eluted with a gradient of 120 ml 0 to 800 mM imidazole in the same buffer. The protein peak was pooled and dialyzed against 2 liters of 50 mM Tris, pH 7.5 containing 5 mM $MgCl_2$, 1 mM EDTA, 5 mM DTT and 20% glycerol. Protein aliquots were stored at −80° C. Protein was at least 95% pure as estimated by the SDS-PAGE.

6.33. Deoxycytidine Kinase Filter Binding Assay

This filter binding assay is based on the binding of the deoxycytidine kinase reaction product dCMP to the positive charged DE-81 filter disk (Ives, D. H. and Wang S.-M., *Methods Enzymol.* 51:337-345 (1978)). Waterman DE-81 or Millipore DEAE 96 well plates were chosen as the binding media for the assay.

Deoxycytidine kinase at a concentration of 5 to 50 nM was incubated with 1 µM of $^3$H-labeled deoxycytidine (20 Ci/mmol) and 10 µM ATP in 50 µl of 50 mM Tris, pH 7.6, containing 5 mM $MgCl_2$, 0.5 mM DTT, 0.1% pluronic acid and 1 mg/ml BSA for 5 to 40 minutes at room temperature. Ten µl of 10 mM deoxycytidine was added and mixed. Ten to 20 µl of reaction solution (per well) was loaded to a DE-81 96 well plate pre-wetted with 1 mM ammonium formate, pH 3.6. The plate was washed three times with 1 mM ammonium formate, pH 3.6 and dried. The plate bottom was sealed with the plate seal and 100 µl of scintillation fluid was added per well and $^3$H-labeled products were counted by a TOPcount scintillation counter.

6.34. Deoxycytidine Kinase Cell-Based Assay

A simple and sensitive cell based assay was developed based on the known in vivo activation of cytosineb-D-arabinofuranoside (AraC) by deoxycytidine kinase: inhibition of deoxycytidine kinase would reverse the cytotoxicity of AraC.

A human T lymphoblastoid cell line CCRF-CEM (ATCC: CCL119) was seeded in 100 µl of a modified RPMI 1640 medium containing 30 nM AraC at 4,000 cells/well. Different concentration of deoxycytidine kinase inhibitors was added. The cells were grown at 37° C. for 3 days. Then, 100 µl of CellTiter-Glo Luminescent Cell Viability Assay reagent (Promega) was added and incubated at room temperature for 60 minutes. Chemiluminescence was recorded using a Tecan luminescence reader. The luminescence represents total ATP concentrations in the cells, which is proportional to cell number.

6.35. Thymidine and Uridine Kinase Inhibition Assays

Whole cell lysate made from CEM-CLL cells, as described above, were used as enzyme source.

Whole cell lysate were incubated with 1 µM of 3H-labeled thymidine (20 Ci/mmol) and 200 µM ATP in 50 µl of 50 mM Tris, pH 7.6, containing 5 mM $MgCl_2$, 0.5 mM DTT with or without compounds at various concentration for 5 to 40 min at room temperature. Then 10 µl of 10 mM cold thymidine was added and mixed. 10 to 20 µl of reaction solution (per well) was loaded to a DE-81 96 well plate pre-wetted with 1 mM ammonium formate, pH 3.6. The plate was washed three times with 1 mM ammonium formate, pH 3.6, and dried. The plate bottom was sealed with the plate seal and 100 µl of scintillation fluid was added per well, and $^3$H-labled products were counted by a TOPcount scintillation counter.

For the uridine kinase inhibition assay, the procedure was the same except the ATP concentration was increased to 400 µM.

6.36. Calculating $IC_{50}$ Values

The $IC_{50}$ of a compound with regard to a given target is determined by fitting the relevant data, using the Levenburg Marquardt algorithm, to the equation:

$$y = A + ((B-A)/(1+((C/x)^D)))$$

wherein A is the minimum y value; B is the maximum y value; C is the $IC_{50}$; and D is the slope. The calculation of the $IC_{50}$ is performed using XLFit4 software (ID Business Solutions Inc., Bridgewater, N.J. 08807) for Microsoft Excel (the above equation is model 205 of that software).

6.37. Inhibition of Cancer Cell Growth

Cell proliferation evaluated by MTS assay was used to study the synergy of compounds of the invention and 4-hydroperoxycyclophosphamide (4-HC), which is an active form of cyclophosphamide in mouse B cell lymphoma cells (BCL-1). BCL-1 cells were grown in RPMI 1640 growth medium with 10% fetal bovine serum and 0.05 mM 2-mercaptoethanol at 37° C. in an incubator with 5% $CO_2$. When the cells reached confluence, they were trypsinized, washed and counted. 12000 mL-1 cells were seeded in triplicate cultures into one well of 96 well plates and cultured overnight with 200 µl growth medium. On the second day, the compound being tested, 4-HC, or a combinations of the two were added to the cells and continued to incubate for 72 hours. Then, a MTS assay was performed for these treated or control cells described as follows.

First, 100 μl of the culture medium from each well of the 96-well plate was carefully removed. Second, 20 μl of pre-warmed MTS reagent (Promega, cat. G3580) was added into each well (including the "blank" wells with no cells), mixed well, and immediately placed in a incubator at 37° C. Finally, 25 μl of 10% SDS was added in each well to stop the reaction after incubated for one hour, and the absorbance for each well was read at 490 nm using a plate reader.

All the experiments were repeated at least three times with similar pattern of results. The combined effect of the compound begin tested and 4-HC was determined by the combination index methodology described by Chou, T.-C., and Talalay, P., *Adv. Enz. Regul.* 22:27-55 (1984).

Figure 2:
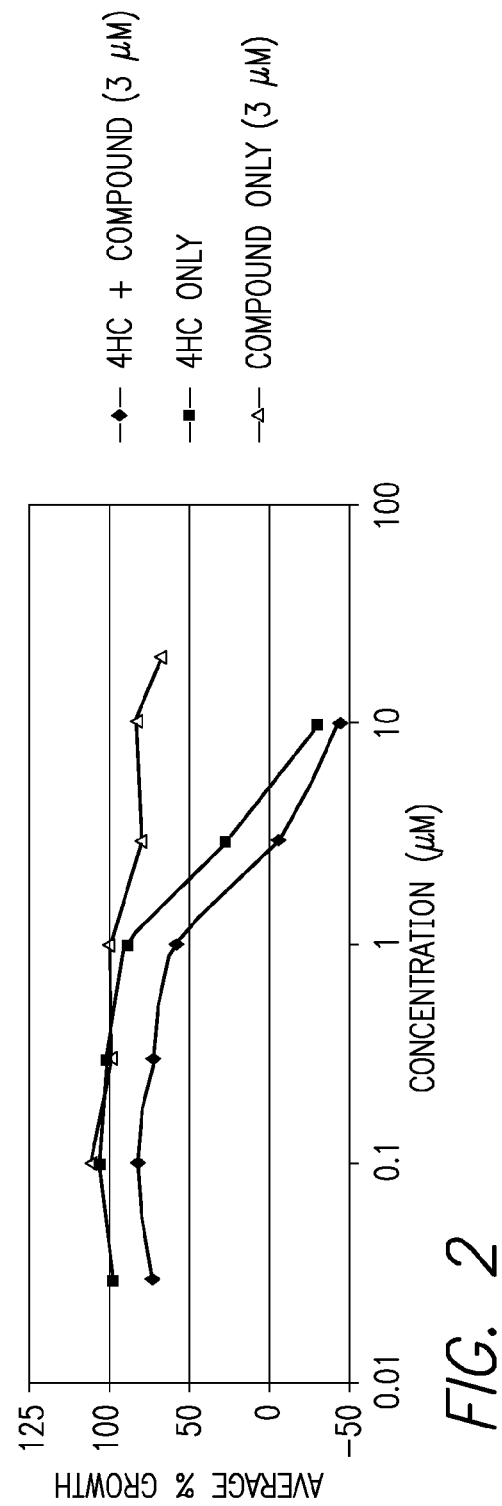
FIG. 2 shows the effect of 3 μM of the compound alone, and in combination with 4-HC, on BCL-1 cell growth.
Figure 3:
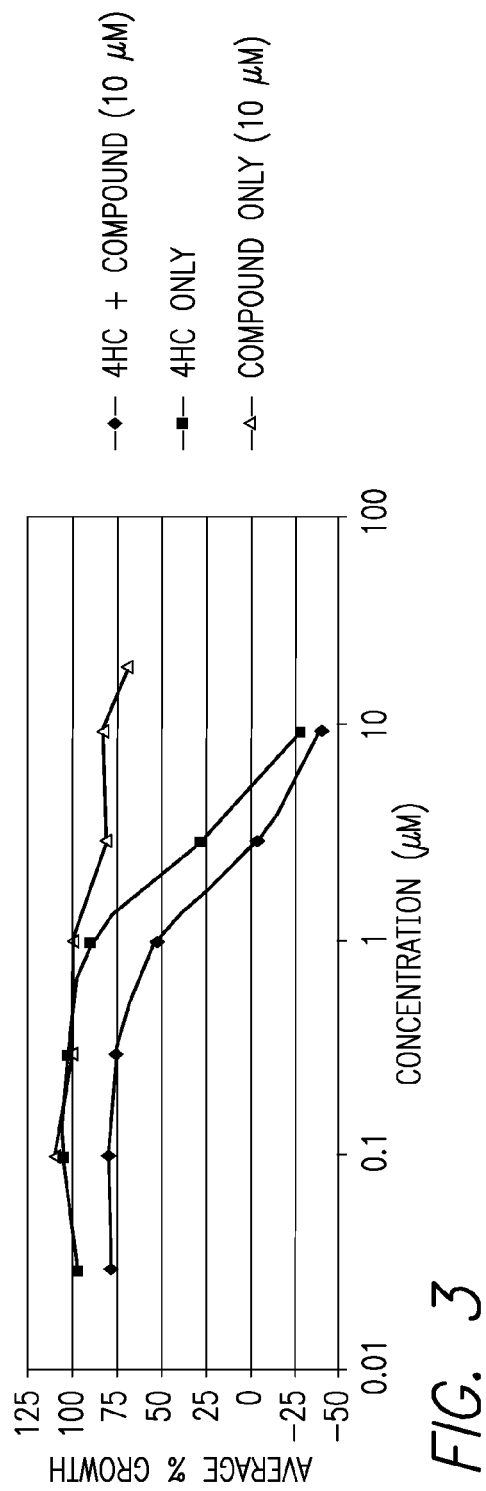
FIG. 3 shows the effect of 10 μM of the compound alone, and in combination with 4-HC, on BCL-1 cell growth.
Figure 4:
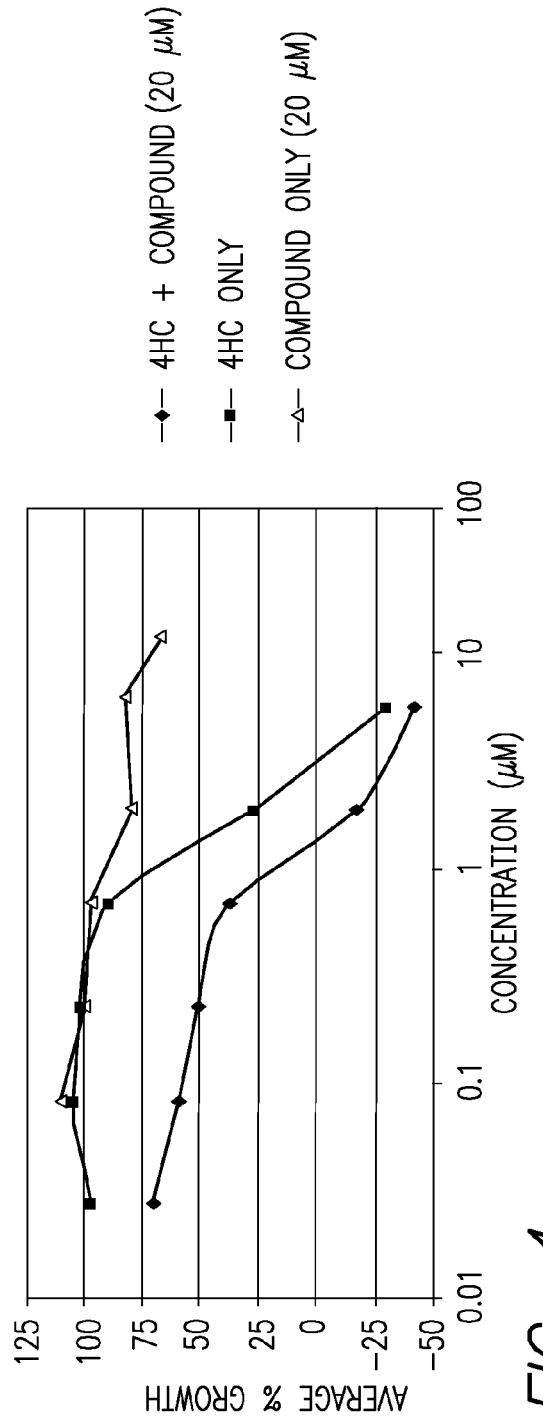
FIG. 4 shows the effect of 20 μM of the compound alone, and in combination with 4-HC, on BCL-1 cell growth.

The effect of different concentrations of a compound of the invention alone and in combination with 4-HC on BCL-1 cell growth is shown in FIGS. 1-4.

All publications (e.g., patents and patent applications) cited above are incorporated herein by reference in their entireties.

What is claimed is:

1. A compound of the formula:

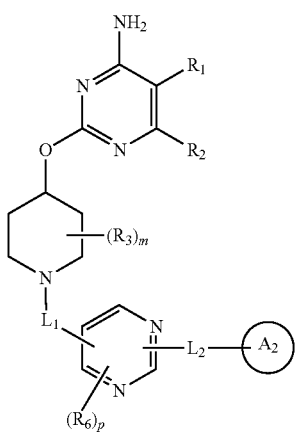

or a pharmaceutically acceptable salt thereof, wherein:
$L_1$ is a bond, —C(O)—, —SO$_2$—, or —C(R$_4$)$_2$—;
$L_2$ is a bond, —O—, —C(O)—, —SO$_2$—, —C(NOH)—, or —C(R$_5$)$_2$—;
$A_2$ is optionally substituted cycloalkyl, aryl or heterocycle;
$R_1$ is hydrogen, halogen, —OH, —NH$_2$, —NO$_2$, —CN, —C(O)OR$_4$, or optionally substituted alkyl;
$R_2$ is hydrogen, halogen, —OH, —NH$_2$, —NO$_2$, —CN, —C(O)OR$_4$, or optionally substituted alkyl;
each $R_3$ is independently =O or optionally substituted lower alkyl;
each $R_4$ is independently hydrogen or lower alkyl;
each $R_5$ is independently hydrogen, fluoro, hydroxyl or lower alkyl, provided that when one of $R_5$ is hydroxyl, the other is neither hydroxyl nor fluoro;
each $R_6$ is halogen, —OH, —NH$_2$, —NO$_2$, —CN, or optionally substituted alkyl;
m is 0-4; and
p is 0-2.

2. The compound of claim 1, which is of the formula:

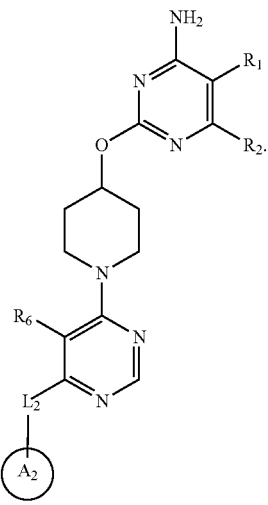

3. A compound of the formula:

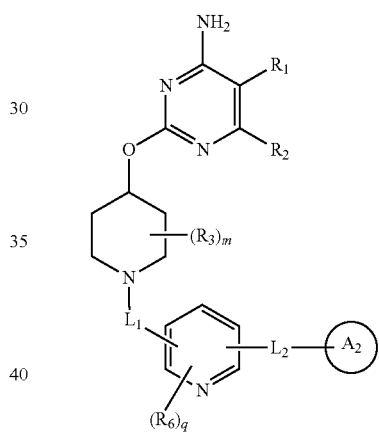

or a pharmaceutically acceptable salt thereof, wherein:
$L_1$ is a bond, —C(O)—, —SO$_2$—, or —C(R$_4$)$_2$—;
$L_2$ is a bond, —O—, —C(O)—, —SO$_2$—, —C(NOH)—, or —C(R$_5$)$_2$—;
$A_2$ is optionally substituted cycloalkyl, aryl or heterocycle;
$R_1$ is hydrogen, halogen, —OH, —NH$_2$, —NO$_2$, —CN, —C(O)OR$_4$, or optionally substituted alkyl;
$R_2$ is hydrogen, halogen, —OH, —NH$_2$, —NO$_2$, —CN, —C(O)OR$_4$, or optionally substituted alkyl;
each $R_3$ is independently =O or optionally substituted lower alkyl;
each $R_4$ is independently hydrogen or lower alkyl;
each $R_5$ is independently hydrogen, fluoro, hydroxyl or lower alkyl, provided that when one of $R_5$ is hydroxyl, the other is neither hydroxyl nor fluoro;
each $R_6$ is halogen, —OH, —NH$_2$, —NO$_2$, —CN, or optionally substituted alkyl;
m is 0-4; and
q is 0-4.

4. The compound of claim 1 or 3, wherein $A_2$ is optionally substituted phenyl, pyridine, quinoline, thiophene, indole, pyrazole, piperidine, morpholine, or pyrrolidine.

5. The compound of claim 1 or 3, wherein $L_2$ is —O—.

6. The compound of claim 1 or 3, wherein $L_2$ is —C(O)— or —C(NOH)—.

7. The compound of claim 1 or 3, wherein $L_2$ is —$C(R_5)_2$—.

8. A compound of the formula:

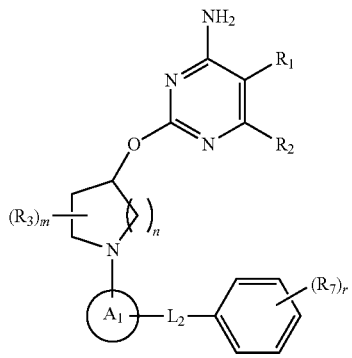

or a pharmaceutically acceptable salt or solvate thereof, wherein:

$L_2$ is a bond, —O—, —C(O)—, —$SO_2$—, —C(NOH)—, or —$C(R_5)_2$—;

$A_1$ is optionally substituted cycloalkyl, aryl or heterocycle;

$R_1$ is hydrogen, halogen, —OH, —$NH_2$, —$NO_2$, —CN, —$C(O)OR_4$, or optionally substituted alkyl;

$R_2$ is hydrogen, halogen, —OH, —$NH_2$, —$NO_2$, —CN, —$C(O)OR_4$, or optionally substituted alkyl;

each $R_3$ is independently =O or optionally substituted lower alkyl;

each $R_4$ is independently hydrogen or lower alkyl;

each $R_5$ is independently hydrogen, fluoro, hydroxyl or lower alkyl, provided that when one of $R_5$ is hydroxyl, the other is neither hydroxyl nor fluoro;

each $R_7$ is halogen, —$OR_8$, —$NH_2$, —$NO_2$, —$C(O)N(R_8)_2$, —CN, or optionally substituted alkyl, aryl or heterocycle;

each $R_8$ is hydrogen or optionally substituted alkyl;

n is 1-3;

m is 0-3 if n is 1, m is 0-4 if n is 2, or m is 0-5 if n is 3; and r is 0-5.

9. The compound of claim 8, wherein $A_1$ is optionally substituted imidazole, pyridine, pyrimidine, purine, triazine, or thiazole.

10. The compound of claim 8, wherein $R_7$ is —$OR_8$, $C(O)N(R_8)_2$, or —CN.

11. The compound of claim 8, wherein $R_7$ is an optionally substituted non-aromatic heterocycle.

12. The compound of claim 11, wherein the heterocycle is hexahydropyrimidine, morpholine, piperidine, pyrrolidine, or 1,2,3,4-tetrahydropyrrolo[1,2-a]pyrimidine.

13. The compound of claim 8, wherein $L_2$ is —O—.

14. The compound of claim 8, wherein $L_2$ is —C(O)— or —C(NOH)—.

15. The compound of claim 8, wherein $L_2$ is —$C(R_5)_2$—.

16. The compound of claim 8, wherein $R_1$ is halogen.

17. The compound of claim 8, wherein $R_2$ is hydrogen.

18. A composition comprising a compound of claim 1, 3, or 8 and a pharmaceutically acceptable excipient or diluent.

* * * * *